US012781392B2

(12) United States Patent
Baek et al.

(10) Patent No.: US 12,781,392 B2
(45) Date of Patent: Nov. 3, 2026

(54) VECTOR LIBRARY FOR YEAST TWO HYBRID SCREENING AND METHOD FOR IDENTIFYING DEUBIQUITINATING ENZYME BINDING TO TARGET PROTEIN USING SAME

(71) Applicant: CHA UNIVERSITY INDUSTRY-ACADEMIC COOPERATION FOUNDATION, Pocheon-si (KR)

(72) Inventors: Kwang-Hyun Baek, Seoul (KR); So-Ra Kim, Gimcheon-si (KR); Seul-Ki Kwon, Seongnam-si (KR); Soo-Yeon Kim, Chuncheon-si (KR); Da-Hye Lee, Seoul (KR)

(73) Assignee: CHA UNIVERSITY INDUSTRY-ACADEMIC COOPERATION FOUNDATION, Pocheon-si (KR)

( * ) Notice: Subject to any disclaimer, the term of this patent is extended or adjusted under 35 U.S.C. 154(b) by 846 days.

(21) Appl. No.: 18/315,532

(22) Filed: May 11, 2023

(65) Prior Publication Data

US 2023/0272555 A1 Aug. 31, 2023

Related U.S. Application Data

(62) Division of application No. 16/636,523, filed as application No. PCT/KR2018/008876 on Aug. 6, 2018, now Pat. No. 11,686,014.

(30) Foreign Application Priority Data

Aug. 8, 2017 (KR) ........................ 10-2017-0100255

(51) Int. Cl.
*C40B 40/08* (2006.01)
*C12N 15/10* (2006.01)

(52) U.S. Cl.
CPC .......... *C40B 40/08* (2013.01); *C12N 15/1055* (2013.01)

(58) Field of Classification Search
None
See application file for complete search history.

(56) References Cited

FOREIGN PATENT DOCUMENTS

KR 10-2003-0002460 A 1/2003

OTHER PUBLICATIONS

Davis et al., "Ubiquitin-Specific Proteases as Druggable Targets", Drug Target Rev., 2015, vol. 2, No. 3, pp. 60-64.
Kwon et al., "Ubiquitin-specific protease 21 regulating the K48-linked polyubiquitination of NANOG", Biochemical and Biophysical Research Communications, 2017, vol. 482, pp. 1443-1448.
Liu et al., "USP21 deubiquitylates Nanog to regulate protein stability and stem cell pluripotency", Signal Transduction and Targeted Therapy, 2016, vol. 1, e16024, 10 pages.

(Continued)

*Primary Examiner* — Christian C Boesen
(74) *Attorney, Agent, or Firm* — Vorys, Sater, Seymour and Pease LLP; Mih Suhn Koh

(57) ABSTRACT

Provided is a vector library for yeast two-hybrid screening of a deubiquitinating enzyme that binds to a target protein and a method for identifying a deubiquitinating enzyme binding to a target protein using the same. Further provided is a method for screening an agent having anti-cancer activity targeting the deubiquitinating enzyme USP1, USP7, USP12, or USP49 identified by the identifying method.

4 Claims, 13 Drawing Sheets

Specification includes a Sequence Listing.

(56) References Cited

OTHER PUBLICATIONS

Quesada et al., "Cloning and enzymatic analysis of 22 novel human ubiquitin-specific proteases", Biochemical and Biophysical Research Communications, 2004, vol. 314, pp. 54-62.
Sowa et al., "Defining the Human Deubiquitinating Enzyme Interaction Landscape", Cell, 2009, vol. 138, pp. 389-403.
Tseng et al., "New Classes of Mind Bomb-Interacting Proteins Identified from Yeast Two-Hybrid Screens", PLoS ONE, 2014, vol. 9, Issue 4, e93394, 12 pages.
Wertz et al., "Regulation of death receptor signaling by the ubiquitin system", Cell Death and Differentiation, 2010, vol. 17, pp. 14-24.
Zhang et al., "The deubiquitinating protein USP24 interacts with DDB2 and regulates DDB2 stability", Cell Cycle, 2012, vol. 11, No. 23, pp. 4378-4384.
Zhang et al., "USP49 deubiquitinates histone H2B and regulates cotranscriptional pre-mRNA splicing", Genes & Development, 2013, vol. 27, pp. 1581-1595.

| DNA binding hybrid | | Activation hybrid | | Colony color |
|---|---|---|---|---|
| 1. Gal4-DBD | USP49 | Gal4-AD | Bax | Blue |
| 2. Gal4-DBD | | Gal4-AD | Bax | No colony |
| 3. Gal4-DBD | Lamin C | Gal4-AD | Bax | No colony |
| 4. Gal4-DBD | USP49 | Gal4-AD | | No colony |
| 5. Gal4-DBD | | Gal4-AD | | No colony |
| 6. Gal4-DBD | p53 | Gal4-AD | SV40T | Blue |

VECTOR LIBRARY FOR YEAST TWO HYBRID SCREENING AND METHOD FOR IDENTIFYING DEUBIQUITINATING ENZYME BINDING TO TARGET PROTEIN USING SAME

REFERENCE TO AN ELECTRONIC SEQUENCE LISTING

The contents of the electronic sequence listing (sequence-listing.xml; Size: 216,555 bytes; and Date of Creation: May 10, 2023) is herein incorporated by reference in its entirety.

TECHNICAL FIELD

The present invention relates to a vector library for yeast two-hybrid screening of a deubiquitinating enzyme that binds to a target protein and a method for identifying a deubiquitinating enzyme binding to a target protein using the same. Also, the present invention relates to a method for screening an agent having anti-cancer activity targeting the deubiquitinating enzyme USP1, USP7, USP12, or USP49 identified by said identifying method.

BACKGROUND ART

Proteins perform a variety of functions in cells and thus the expressions, degradations, and activity maintenances thereof greatly affect cell homeostasis. Ubiquitination is a process in which ubiquitin binds to a target protein, thereby proteasomes recognize the ubiquitin and degrade the target protein. In addition, ubiquitination is also involved in the function and activity of proteins, and thus regulates various signal pathways to determine cell fate. The process reversing this regulation is called as deubiquitination. A deubiquitinating enzyme cleaves ubiquitins bound to a target protein, thereby inhibiting the degradation by proteasomes or reversely-regulating function and activity of protein regulated by ubiquitination. Ubiquitination and deubiquitination play an important role in protein homeostasis and cell fate, and when this system works abnormally, it causes a variety of diseases, including cancer.

Abnormal protein expressions cause the onset of diseases. For example, improper expression or function of proteins may cause inhibition of apoptosis of cells, thereby resulting in excessive proliferation or may cause over-apoptosis of cells, thereby leading to diseases. In this regard, deubiquitinating enzymes are key molecules that can regulate the stability and function of proteins, attracting attention as a therapeutic agent for diseases. Therefore, it is important to identify the interaction of a target protein with deubiquitinating enzymes and their roles in intracellular signal pathway systems. For this purpose, the identification of a deubiquitinating enzyme that binds to a target protein will be a basis for the research thereon. However, since the identification of said interacting proteins requires high costs, there is a need for an efficient and relatively inexpensive screening system thereof.

DISCLOSURE

Technical Problem

The present invention provides a vector library for yeast two-hybrid screening of a deubiquitinating enzyme that binds to a target protein. And also, the present invention provides a method for identifying a deubiquitinating enzyme binding to a target protein, using the vector library.

In addition, it has been found by said identifying method that the deubiquitinating enzyme USP1, USP7, USP12, or USP49 specifically binds to Bax which is known to be involved in apoptosis of cells. Therefore, the present invention provides a method for screening an agent having anti-cancer activity targeting the deubiquitinating enzyme USP1, USP7, USP12, or USP49.

Technical Solution

In accordance with an aspect of the present invention, there is provided a vector library for yeast two-hybrid screening of a deubiquitinating enzyme that binds to a target protein, comprising: a vector obtained by inserting a gene encoding a deubiquitinating enzyme USP1 in an empty vector having a DNA-binding domain; a vector obtained by inserting a gene encoding a deubiquitinating enzyme USP2 in an empty vector having a DNA-binding domain; a vector obtained by inserting a gene encoding a deubiquitinating enzyme USP3 in an empty vector having a DNA-binding domain; a vector obtained by inserting a gene encoding a deubiquitinating enzyme USP4 in an empty vector having a DNA-binding domain; a vector obtained by inserting a gene encoding a deubiquitinating enzyme USP5 in an empty vector having a DNA-binding domain; a vector obtained by inserting a gene encoding a deubiquitinating enzyme USP6 in an empty vector having a DNA-binding domain; a vector obtained by inserting a gene encoding a deubiquitinating enzyme USP7 in an empty vector having a DNA-binding domain; a vector obtained by inserting a gene encoding a deubiquitinating enzyme USP8 in an empty vector having a DNA-binding domain; a vector obtained by inserting a gene encoding a deubiquitinating enzyme USP10 in an empty vector having a DNA-binding domain; a vector obtained by inserting a gene encoding a deubiquitinating enzyme USP11 in an empty vector having a DNA-binding domain; a vector obtained by inserting a gene encoding a deubiquitinating enzyme USP12 in an empty vector having a DNA-binding domain; a vector obtained by inserting a gene encoding a deubiquitinating enzyme USP14 in an empty vector having a DNA-binding domain; a vector obtained by inserting a gene encoding a deubiquitinating enzyme USP15 in an empty vector having a DNA-binding domain; a vector obtained by inserting a gene encoding a deubiquitinating enzyme USP16 in an empty vector having a DNA-binding domain; a vector obtained by inserting a gene encoding a deubiquitinating enzyme USP17 in an empty vector having a DNA-binding domain; a vector obtained by inserting a gene encoding a deubiquitinating enzyme USP18 in an empty vector having a DNA-binding domain; a vector obtained by inserting a gene encoding a deubiquitinating enzyme USP19 in an empty vector having a DNA-binding domain; a vector obtained by inserting a gene encoding a deubiquitinating enzyme USP20 in an empty vector having a DNA-binding domain; a vector obtained by inserting a gene encoding a deubiquitinating enzyme USP21 in an empty vector having a DNA-binding domain; a vector obtained by inserting a gene encoding a deubiquitinating enzyme USP25 in an empty vector having a DNA-binding domain; a vector obtained by inserting a gene encoding a deubiquitinating enzyme USP28 in an empty vector having a DNA-binding domain; a vector obtained by inserting a gene encoding a deubiquitinating enzyme USP30 in an empty vector having a DNA-binding domain; a vector obtained by inserting a gene encoding a deubiquitinating enzyme USP33 in an empty vector having a DNA-binding domain; a vector obtained by inserting a gene encoding a deubiquitinating enzyme USP34 in an empty vector having a DNA-binding domain; a vector obtained by inserting a gene encoding a deubiquitinating enzyme USP35 in an empty vector having a DNA-binding domain; a vector obtained by inserting a gene encoding a deubiquitinating enzyme USP36 in an empty vector having a DNA-binding domain; a vector obtained by inserting a gene encoding a deubiquitinating enzyme USP37 in an empty vector having a DNA-binding domain; a vector obtained by inserting a gene encoding a deubiquitinating enzyme USP38 in an empty vector having a DNA-binding domain; a vector obtained by inserting a gene encoding a deubiquitinating enzyme USP39 in an empty vector having a DNA-binding domain; a vector obtained by inserting a gene encoding a deubiquitinating enzyme USP44 in an empty vector having a DNA-binding domain; a vector obtained by inserting a gene encoding a deubiquitinating enzyme USP46 in an empty vector having a DNA-binding domain; and a vector obtained by inserting a gene encoding a deubiquitinating enzyme USP49 in an empty vector having a DNA-binding domain. In an embodiment, the empty vector having a DNA-binding domain may a pGBT9 vector.

In accordance with another aspect of the present invention, there is provided a method for identifying a deubiquitinating enzyme binding to a target protein, the method comprising: (a) inserting a gene encoding a target protein into an empty vector having a transcription activation domain to prepare a vector; (b) transforming yeasts with each vector of the vector library and the vector prepared in Step (a); and (c) culturing the yeasts obtained in Step (b) in a medium containing X-gal and free of tryptophan and leucine. In an embodiment, the empty vector having a transcription activation domain may a pGAD424 vector.

In accordance with still another aspect of the present invention, there is provided a method for screening an agent having anti-cancer activity, the method comprising: (i) treating with candidate materials a cell overexpressing a deubiquitinating enzyme USP1, USP7, USP12, or USP49 and Bax protein, followed by culturing the cell; and (ii) measuring apoptosis of the cell cultured in Step (i) and selecting a material inducing apoptosis of the cell. In an embodiment, the deubiquitinating enzyme of Step (i) may USP49.

Advantageous Effects

The vector library of the present invention can be used to identify the deubiquitinating enzymes binding to a target protein efficiently and at low cost, and thus can be usefully applied for elucidating various mechanisms thereof in cells. In addition, by applying the vector library of the present invention, it has been found that the deubiquitinating enzymes USP1, USP7, USP12, and USP49 specifically bind to Bax, an apoptosis-associated protein. Therefore, the screening method of the present invention can be usefully applied for screening an agent having anti-cancer activity targeting the deubiquitinating enzymes USP1, USP7, USP12, and USP49.

BEST MODE

Figure 1:
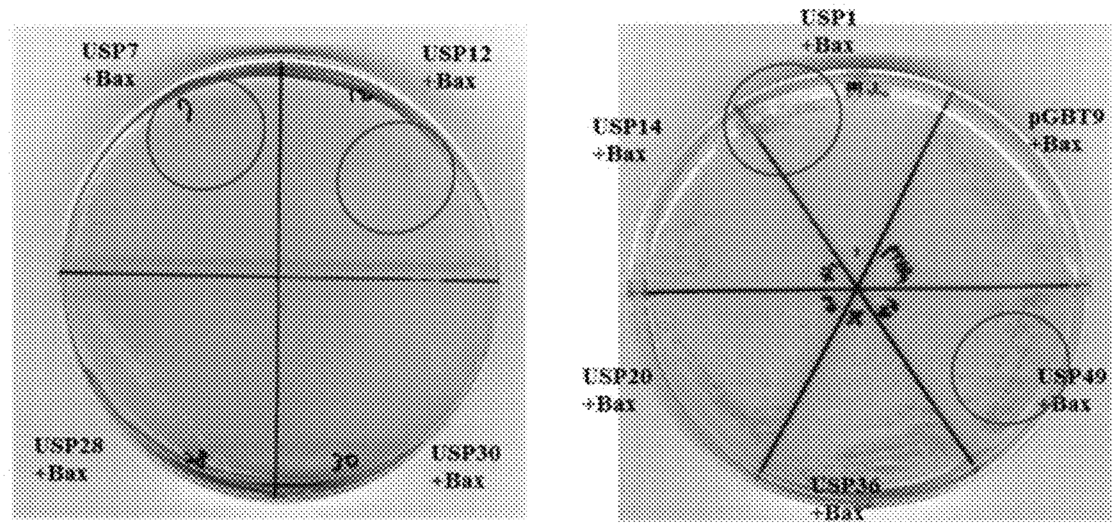
FIG. 1 shows the results obtained by screening deubiquitinating enzymes that bind to Bax protein with the vector library of the present invention.

The present invention provides a vector library for yeast two-hybrid screening of a deubiquitinating enzyme that binds to a target protein. Specifically, the present invention provides a vector library for yeast two-hybrid screening of a deubiquitinating enzyme that binds to a target protein, comprising: a vector obtained by inserting a gene encoding a deubiquitinating enzyme USP1 in an empty vector having a DNA-binding domain; a vector obtained by inserting a gene encoding a deubiquitinating enzyme USP2 in an empty vector having a DNA-binding domain; a vector obtained by inserting a gene encoding a deubiquitinating enzyme USP3 in an empty vector having a DNA-binding domain; a vector obtained by inserting a gene encoding a deubiquitinating enzyme USP4 in an empty vector having a DNA-binding domain; a vector obtained by inserting a gene encoding a deubiquitinating enzyme USP5 in an empty vector having a DNA-binding domain; a vector obtained by inserting a gene encoding a deubiquitinating enzyme USP6 in an empty vector having a DNA-binding domain; a vector obtained by inserting a gene encoding a deubiquitinating enzyme USP7 in an empty vector having a DNA-binding domain; a vector obtained by inserting a gene encoding a deubiquitinating enzyme USP8 in an empty vector having a DNA-binding domain; a vector obtained by inserting a gene encoding a deubiquitinating enzyme USP10 in an empty vector having a DNA-binding domain; a vector obtained by inserting a gene encoding a deubiquitinating enzyme USP11 in an empty vector having a DNA-binding domain; a vector obtained by inserting a gene encoding a deubiquitinating enzyme USP12 in an empty vector having a DNA-binding domain; a vector obtained by inserting a gene encoding a deubiquitinating enzyme USP14 in an empty vector having a DNA-binding domain; a vector obtained by inserting a gene encoding a deubiquitinating enzyme USP15 in an empty vector having a DNA-binding domain; a vector obtained by inserting a gene encoding a deubiquitinating enzyme USP16 in an empty vector having a DNA-binding domain; a vector obtained by inserting a gene encoding a deubiquitinating enzyme USP17 in an empty vector having a DNA-binding domain; a vector obtained by inserting a gene encoding a deubiquitinating enzyme USP18 in an empty vector having a DNA-binding domain; a vector obtained by inserting a gene encoding a deubiquitinating enzyme USP19 in an empty vector having a DNA-binding domain; a vector obtained by inserting a gene encoding a deubiquitinating enzyme USP20 in an empty vector having a DNA-binding domain; a vector obtained by inserting a gene encoding a deubiquitinating enzyme USP21 in an empty vector having a DNA-binding domain; a vector obtained by inserting a gene encoding a deubiquitinating enzyme USP25 in an empty vector having a DNA-binding domain; a vector obtained by inserting a gene encoding a deubiquitinating enzyme USP28 in an empty vector having a DNA-binding domain; a vector obtained by inserting a gene encoding a deubiquitinating enzyme USP30 in an empty vector having a DNA-binding domain; a vector obtained by inserting a gene encoding a deubiquitinating enzyme USP33 in an empty vector having a DNA-binding domain; a vector obtained by inserting a gene encoding a deubiquitinating enzyme USP34 in an empty vector having a DNA-binding domain; a vector obtained by inserting a gene encoding a deubiquitinating enzyme USP35 in an empty vector having a DNA-binding domain; a vector obtained by inserting a gene encoding a deubiquitinating enzyme USP36 in an empty vector having a DNA-binding domain; a vector obtained by inserting a gene encoding a deubiquitinating enzyme USP37 in an empty vector having a DNA-binding domain; a vector obtained by inserting a gene encoding a deubiquitinating enzyme USP38 in an empty vector having a DNA-binding domain; a vector obtained by inserting a gene encoding a deubiquitinating enzyme USP39 in an empty vector having a DNA-binding domain; a vector obtained by inserting a gene encoding a deubiquitinating enzyme USP44 in an empty vector having a DNA-binding domain; a vector obtained by inserting a gene encoding a deubiquitinating enzyme USP46 in an empty vector having a DNA-binding domain; and a vector obtained by inserting a gene encoding a deubiquitinating enzyme USP49 in an empty vector having a DNA-binding domain.

Figure 12:
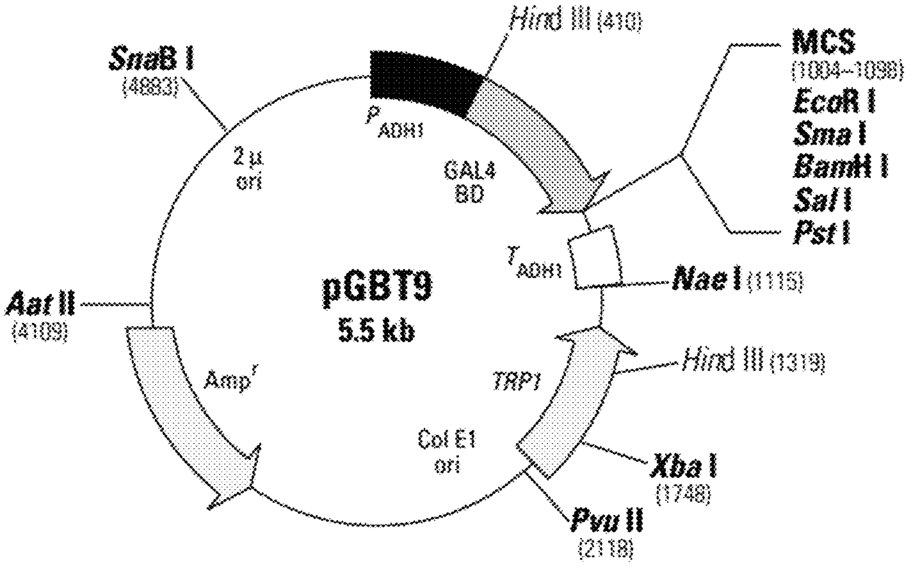
FIG. 12 shows a cleavage map of the pGBT9 vector.

In the vector library of the present invention, as the empty vector having a DNA-binding domain (DNA-BD), any vector capable of providing a DNA-binding domain to yeast may be used without limitation. For example, the empty vector having a DNA-binding domain (DNA-BD) may be the pGBT9 vector having a cleavage map of FIG. 12, but is not limited thereto. Insertion of the gene encoding a deubiquitinating enzyme into an empty vector having a DNA-binding domain may be performed by a conventional method used in the field of biotechnology. For example, said insertion may be carried out by incubating an empty vector having a DNA-binding domain along with the gene encoding a deubiquitinating enzyme, using appropriate restriction enzymes. All of the genes encoding deubiquitinating enzymes are known in GenBank. In addition, the restriction enzymes include e.g., EcoR I, Sma I, BamH I, Sal I, Pst I, but are not limited thereto.

The present invention also provides a method for identifying a deubiquitinating enzyme binding to a target protein, using the vector library. That is, the present invention provides a method for identifying a deubiquitinating enzyme binding to a target protein, the method comprising: (a) inserting a gene encoding a target protein into an empty vector having a transcription activation domain to prepare a vector; (b) transforming yeasts with each vector of the vector library and the vector prepared in Step (a); and (c) culturing the yeasts obtained in Step (b) in a medium containing X-gal and free of tryptophan and leucine.

Figure 13:
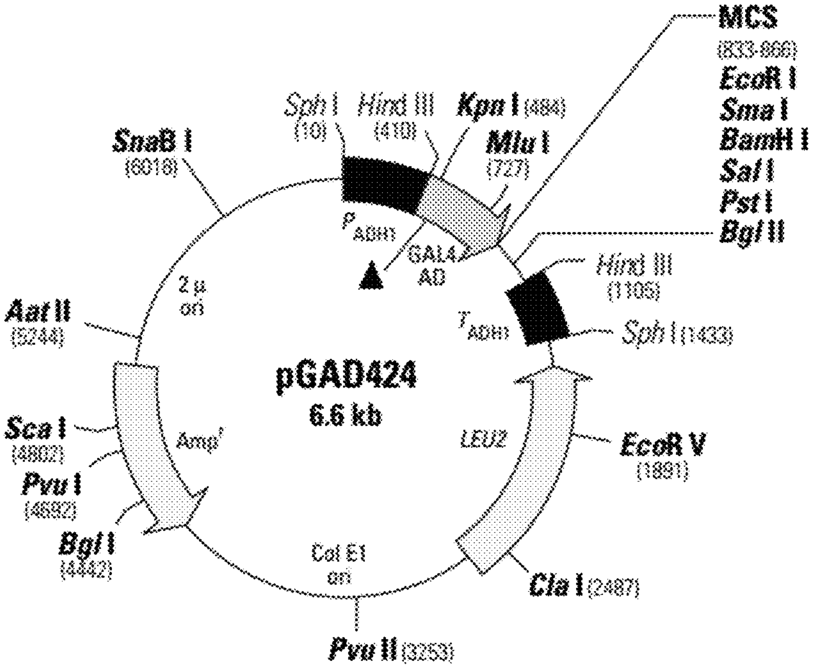
FIG. 13 shows a cleavage map of the pGAD424 vector.

In the method for identifying a deubiquitinating enzyme of the present invention, as the empty vector having a transcription activation domain, any vector capable of providing a transcription activation domain to yeast may be used without limitation. For example, the empty vector having a transcription activation domain may be the pGAD424 vector having a cleavage map of FIG. 13, but is not limited thereto. Insertion of the gene encoding a gene encoding a target protein into an empty vector having a transcription activation domain may be performed by a conventional method used in the field of biotechnology. For example, said insertion may be carried out by incubating an empty vector having a transcription activation domain along with the gene encoding a target protein, using appropriate restriction enzymes. In addition, the restriction enzymes include e.g., EcoR I, Sma I, BamH I, Sal I, Pst I, Bgl II, but are not limited thereto.

It has been found by the identifying method of the present invention that the deubiquitinating enzyme USP1, USP7, USP12, or USP49 specifically binds to Bax which is known to be involved in apoptosis of cells.

Bax belongs to the proapoptotic group of Bcl-2 proteins and is a key molecule in the induction of apoptosis. Bax is present in the cytosol as a monomer in unstressed cells. When the cells undergo stress, Bax is activated by the proapoptotic BH3-proteins. The activated Bax is translocated to the surface of the mitochondria and inserted into the mitochondrial outer membrane (MOM). Bax then undergoes homo-oligomerization, leading to pore formation in the MOM. Then, the proapoptotic molecule cytochrome c is released and apoptosis is induced. If the gene that encodes Bax is mutated, cells may be less susceptible to cell death. The expression level of Bax is related to malignant transformation, tumor progression, and metastasis, thereby low expression of Bax is considered as a negative factor in cancer diseases. Decreased level of Bax degradation is appeared in aggressive human prostate cancer.

Figure 11:
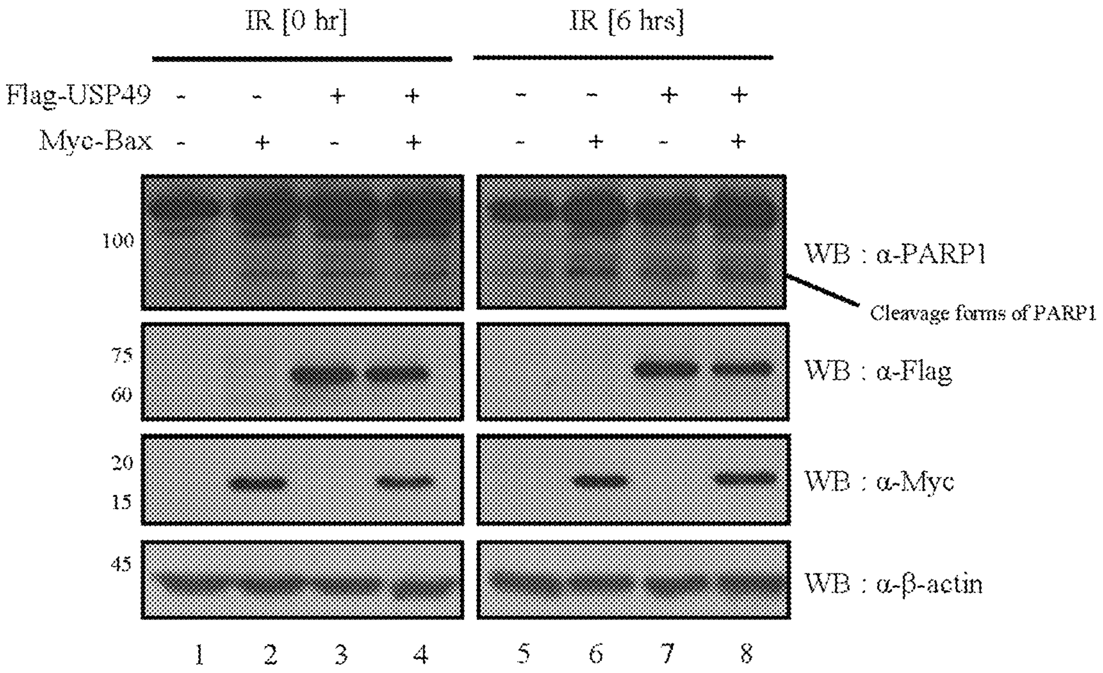
FIG. 11 shows the results obtained by evaluating whether USP49 regulates Bax, through treating the HCT116 cells overexpressed with Flag-USP49 or Myc-Bax with IR irradiation (10 Gy) and then harvesting the cells after 6 hours.

Therefore, the deubiquitinating enzyme USP1, USP7, USP12, or USP49 may function as a novel target for screening an agent having anti-cancer activity. Especially, it has been found by the present invention that, even if Bax-overexpressed cells are allowed to overexpress USP49, Bax can be regulated in a proteasome-independent pathway without apoptosis of the cells, thereby being suitably applicable to a screening method (FIG. 11). Therefore, an agent having anti-cancer activity may be screened by treating with candidate materials cells overexpressing the deubiquitinating enzyme USP1, USP7, USP12, or USP49 and Bax protein; and then measuring apoptosis of the cultured cells. That is, the present invention provides a method for screening an agent having anti-cancer activity, the method comprising: (i) treating with candidate materials a cell overexpressing a deubiquitinating enzyme USP1, USP7, USP12, or USP49 and Bax protein, followed by culturing the cell; and (ii) measuring apoptosis of the cell cultured in Step (i) and selecting a material inducing apoptosis of the cell. In an embodiment, the deubiquitinating enzyme of Step (i) may USP49.

Hereinafter, the present invention will be described more specifically by the following examples. However, the following examples are provided only for illustrations and thus the present invention is not limited to or by them.

Examples

1. Materials and Methods (1) Cell Culture and Transfection 293T cells were grown with Dulbecco's modified Eagle's medium (DMEM, Gibco, Grand Island, NY, USA) containing 10% fetal bovine serum (FBS, Gibco, Grand Island, NY, USA), 1% penicillin-streptomycin (Gibco, Grand Island, NY, USA). HCT116 cells were grown in RPMI 1640 medium (Gibco, Grand Island, NY, USA) supplemented with 10% FBS and 1% penicillin-streptomycin. The cells were grown in a 5% $CO_2$ incubator at 37° C. Transfections were performed with 150 mM NaCl and 10 mM polyethylenimine (PEI, Polysciences, Inc., Warrington, PA, USA).

(2) Antibodies

Monoclonal anti-Bax (2D2) (1:1000, Santa Cruz Biotechnology, Santa Cruz, CA, USA), anti-β-actin (1:1000, Santa Cruz, CA, USA), anti-HA (1:1000, 12CA5, Roche, Basel, Switzerland), anti-Flag (1:1000, Sigma-Aldrich, St. Louis, MO, USA) and anti-PARP1 (1:1000, Santa Cruz, CA, USA) antibodies were used for Western blotting, immunoprecipitation, and immunocytochemical staining. Anti-K48 (1:500, Cell signaling, Danvers, MA, USA) and anti-K63 (1:100, Cell signaling, Danvers, MA, USA) antibodies were used for DUB assay. Easy Blot antibody (1:1000, GeneTex, TX, USA) was used for decreasing the signal of chains of IgG.

(3) Construction of Expression Vectors and Primers

To generate deletion mutants of Bax (1-219), Bax (220-334) and Bax (335-579), we used the forward primers, (5'-GAA TTC GCA TGG ACG GGT-3'), (5'-GAA TTC CGA TGG AGC TGC A-3') and (5'-GAA TTC GCA AAC TGG TGC TC-3'). And also, the reverse primers, (5'-CTC GAG CGG TTA CTG TCC AG-3'), (5'-CTC GAG CCG CTG GCA AAG-3') and (5'-CTC GAG CGT CAG CCC ATC-3') were used.

Point mutation of USP49 (C262S) was generated through the site-directed mutagenesis. The forward primer (5'-CTG GGC AAC ACC AGC TAC ATG-3') and the reverse primer (5'-TGG AGT TCA TGT AGC TGG TGT-3') were used for generating a mutant. After purification of PCR product, Dpn I (Enzynomics, Daejeon, Korea) enzyme was added. The construct was confirmed by sequencing.

To generate deletion mutants of USP49 (1-762), USP49 (763-1131), and USP49 (1132-2067), we used the forward primers (5'-GAA TTC GAT GGA TAG ATG C-3'), (5'-GAA TTC TCT GCG CAA CCT G-3'), and (5'-TCT AGA ACC CTT CGC CAT GC-3'), and the reverse primers (5'-CTC GAG GCC CGT GAC GCC-3'), (5'-CTC GAG CGA CAC TAG GGC-3'), and (5'-TAC GTA TCA ACC CCT TTC C-3').

For the generation of shUSP49, three kinds of shRNAs for USP49 were constructed and inserted into the pSilencer 3.1 H1 neo vector (Ambion, Austin, TX, USA). The target sequences of shUSP49s are: #1 (5'-GTC TTC ACT GTA GCT CAA G-3'), #2 (5'-GGA CTA CGT GCT CAA TGA T-3') and #3 (5'-GGA CTA CGT GCT CAA TGA T-3') (UbiProtein Corp, Seongnam, Republic of Korea).

To perform RT-PCR, we used the forward primer (5'-AGG ACT ACG TGC TCA ATG ATA ACC-3') and the reverse primer (5'-GCA GGA GCA GCC GTG CAC TCT-3') for targeting USP49. The forward primer (5'-ATC CCA TCA CCA TCT TCC-3') and the revers primer (5'-CCA TCA CGC CAC AGT TTC-3') were also used for targeting GAPDH.

(4) Preparation of the Vector Library for Yeast Two-Hybrid Screening

Each full-length cDNAs encoding the deubiquitinating enzymes shown in Table 1 were obtained from GenBank. The pGBT9-deubiquitinating enzyme library for yeast two-hybrid screening was prepared by performing the respective cloning, through incubating the pGBT9 vectors (Clontech, Palo Alto, CA, USA) along with said cDNAs, using appropriate restriction enzymes.

TABLE 1

| Deubiquitinating enzyme | Molecular weight (kDa) |
|---|---|
| USP1 | 90.5 |
| USP2 | 68 |
| USP3 | 59 |
| USP4 | 108 |
| USP5 | 95.8 |
| USP6 | 90 |
| USP7 | 130 |
| USP8 | 123 |
| USP10 | 87 |
| USP11 | 110 |
| USP12 | 60 |
| USP14 | 56 |
| USP15 | 112 |
| USP16 | 47 |
| USP17 | 22 |
| USP18 | 43 |
| USP19 | 145 |
| USP20 | 102 |
| USP21 | 62 |
| USP25 | 126 |
| USP28 | 122 |
| USP30 | 59 |
| USP33 | 107 |
| USP34 | 387 |
| USP35 | 113.4 |
| USP36 | 123 |
| USP37 | 110 |
| USP38 | 117 |
| USP39 | 65 |
| USP44 | 81 |
| USP46 | 42 |
| USP49 | 73 |

(5) Yeast Two-Hybrid Screening (5-1) Transformation of pGBT9-Deubiquitinating Enzyme to Yeast Cells (First Transformation)

Yeast strain (*Saccharomyces cerevisiae* AH109) was streaked on YPD (Clontech, Palo Alto, CA, USA) agar plates and incubated at 30° C. for 3-4 days. The colony was cultured in YPD liquid media (Clontech, Palo Alto, CA, USA) and the cultured yeast cells were centrifuged at 2500 rpm for 2 minutes 30 seconds when $OD_{600}$ value thereof reached 0.8-1.0. After removing the supernatant, the cells were treated with distilled water (3 ml), centrifuged at 2500 rpm for 2 minutes 30 seconds, resuspended with the lithium acetate (LiAc) solution, and then incubated at room temperature for 5 minutes. After centrifuging the cells at 2500 rpm for 5 minutes, the LiAc solution (600 μl) was added for resuspension of the cells. The pGBT9 containing a deubiquitinating enzyme gene (1 μg) and the yeast (100 μl) were then mixed in the LiAc solution, followed by incubating for 15 minutes at 30° C. in a shaking incubator. The polyethylene glycol (PEG) in LiAc solution (600 μl) was added thereto and the mixture was incubated at 30° C. for 30 minutes in a shaking incubator. DMSO (50 μl) was then added, and the cells were heat-shocked at 42° C. for 15 minutes, followed by centrifuging to remove the supernatant. Fresh YPD media (600 μl) was added for resuspension of the cells, which were incubated for 1-2 hours, and centrifuged to precipitate the cells. After removing the supernatant (500 μl), the cells were streaked on -Trp minimal agar plate and then incubated at 30° C. for 3-4 days.

(5-2) Transformation of Bax and Nanog to the First-Transformed Yeast Cells (Second Transformation)

The yeast cells transformed with each deubiquitinating enzyme were cultured in in a -Trp liquid media and the cultured yeast cells were centrifuged at 2500 rpm for 2 minutes 30 seconds when $OD_{600}$ value thereof reached 0.8-1.0. After removing the supernatant, the cells were treated with distilled water (3 ml), centrifuged at 2500 rpm for 2 minutes 30 seconds, resuspended with the LiAc solution, and then incubated at room temperature for 5 minutes. After centrifuging the cells at 2500 rpm for 5 minutes, the LiAc solution (600 μl) was added for resuspension of the cells. The cDNAs encoding target proteins (Bax and Nanog) were inserted into a pGAD424 vector having a transcription activation domain, to prepare pGAD424-Bax and pGAD424-Nanog, respectively. pGAD424-Bax (1 μg) or pGAD424-Nanog (1 μg) and the yeast (100 μl) were then mixed in the LiAc solution, followed by incubating for 15 minutes in a shaking incubator. The PEG in LiAc solution (600 μl) was added thereto and the mixture was incubated for 30 minutes in a shaking incubator. DMSO (50 μl) was then added, and the cells were heat-shocked at 42° C. for 15 minutes, followed by centrifuging to remove the supernatant. -Trp liquid media (600 μl) was added for resuspension of the cells, which were incubated for 1-2 hours, and centrifuged to precipitate the cells. After removing the supernatant (500 μl), the cells were streaked on -Trp/-Leu minimal agar plate containing X-gal (Clontech, Palo Alto, CA, USA) and then incubated at 30° C. for 3-4 days. In this process, the yeast transformed with a deubiquitinating enzyme is transformed with the target protein cDNA; and when the two proteins bind each other, blue colonies appear.

(6) Preparation of Cell Lysates, Western Blotting, and Immunoprecipitation

Cells were washed with phosphate buffered saline (PBS) and lysed in a lysis buffer (Tris-HCl [pH 7.5] 50 mM, NaCl 300 mM, EDTA 1 mM, Glycerol 10%, Triton X-100 1%), CHAPS buffer (150 mM NaCl, 10 mM HEPES at pH 7.4 and 1.0% CHAPS) and NP40 buffer (145.2 mM potassium chloride, 5 mM $MgCl_2$, 1 mM EGTA 10 mM HEPES at pH 7.4 and 0.2% NP40). The samples were incubated for 20 minutes on ice and then insoluble material was pelleted by a 20-minute centrifugation at 13,000 rpm at 4° C. The resulting supernatant was collected.

Western blotting was conducted by loading 20 μg of protein per lane on an 8-12% SDS-PAGE and the proteins were transferred onto polyvinylidene fluoride (PVDF) microporous membranes (Millipore, Billerica, MA, USA). Membranes were blocked in TTBS (20 mM Tris-HCl [pH 7.5], 150 mM NaCl, 0.05% Tween 20) containing 5% skim milk for 20 minutes and incubated with primary antibodies at 4° C. overnight. The blots were then washed in TTBS and incubated in TTBS containing 3% skim milk and secondary antibodies for 1 hour. The membranes were washed again in TTBS and visualized with ECL reagent solution (Young In Frontier, Seoul, Korea).

For immunoprecipitation of proteins, cell lysates were incubated with antibodies at 4° C. overnight and protein A/G PLUS agarose beads (Santa Cruz Biotechnology, Santa Cruz, CA, USA) were added and rotated for 2 hours. The washed samples were boiled in SDS sample buffer and detected by Western blotting.

(7) GST Pull-Down Assay

*E. coli* BL21 cells transformed with pGEX-4T-3 vector or pGEX-4T-3-Bax were grown at 37° C. When cell density ($OD_{600}$ value) reached 0.6, expressions of recombinant proteins were induced by 5 mM IPTG (Promega, Madison, WI, USA) at 31° C. for 4 hours. The cells were lysed and the lysates containing proteins were rotated with Glutathione-Sepharose beads (GST beads) (Pharmacia Biotech, Uppsala, Sweden), so as to induce the binding between the GST beads and GST or GST-Bax. 293T cells overexpressed with Myc-USP12 or Flag-USP49 were lysed and the cell extracts were mixed with GST and GST-Bax tagging GST beads. The mixtures were washed to collect GST and GST-Bax from the lysate. The protein bound to GST and GST-Bax was analyzed by Western blotting and probed with an anti-Myc antibody (1:1000 Sigma-Aldrich, St. Louis, MO, USA) and an anti-Flag antibody (1:1000 Sigma-Aldrich, St. Louis, MO, USA). GST proteins were visualized by Coomassie Brilliant Blue (CBB) staining (Sigma-Aldrich, St. Louis, MO, USA).

(8) Immunocytochemical Staining and Confocal Microscopy

HCT116 cells were seeded on glass coverslips placed on a 12-well plate. The cells were fixed with 4% formaldehyde for 15 minutes and were blocked with PBS containing 2% normal goat serum and 1% triton X-100 for 1 hour at room temperature. The cells were incubated with primary antibodies overnight at 4° C. and then incubated with Alexa-Fluor-488-cojugated goat anti-mouse (1:100, Invitrogen, Carlsbad, CA, USA) and goat anti-rabbit 1:100, Invitrogen, Carlsbad, CA, USA) for 1 hour at room temperature. The samples were visualized with a confocal microscope (TCSSP5 II, Leica, Mannheim, Germany).

(9) Ubiquitination and Deubiquitination Assays

For the ubiquitination assay, HA-ubiquitin, HA-ubiquitin (K48R), and HA-ubiquitin (K63R) were transfected into 293T cells. Cells were harvested and cell lysates were used for immunoprecipitation with an anti-Bax antibody (1:1000, Santa Cruz Biotechnology, Santa Cruz, CA, USA). Deubiquitination assay was performed with HA-Ubiquitin and Flag-Usp49. MG132 was treated for 4 hours before harvest. An anti-Bax antibody (1:1000, Santa Cruz Biotechnology, Santa Cruz, CA, USA) was used to precipitate proteins and the samples were analyzed by Western blotting. Ubiquitination level was detected by an anti-HA antibody (1:1000, 12CA5, Roche, Basel, Switzerland).

2. Results

FIG. 1 shows the results obtained by screening the deubiquitinating enzymes that regulate Bax, an apoptosis-associated protein, with the vector library prepared the present invention. As the results of the screening, the colonies transformed with USP1, USP7, USP12, and USP49 showed blue color.

Figure 2:
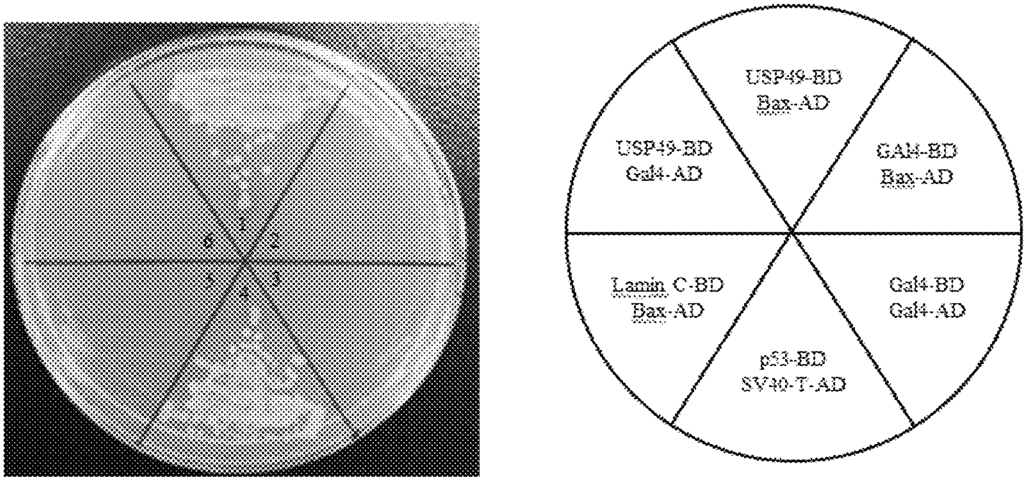
FIG. 2 shows the results obtained by confirming using a negative control and a positive control, after screening deubiquitinating enzymes that bind to Bax protein with the vector library of the present invention.

FIG. 2 shows the results obtained by confirming the results of FIG. 1 using controls. pGBT9 and pGAD424 vectors, i.e., empty vectors without cDNA insertion, were used as negative controls; and p53 and SV40 large T antigens, which were known to interact each other, were used as positive controls. Blue colonies were formed in the yeasts transformed with p53 and SV40 large T antigen and in the yeasts transformed with USP49 and Bax, while the colonies did not grow in the yeast transformed with the negative controls. These results indicate that the two proteins specifically interact.

Figure 3:
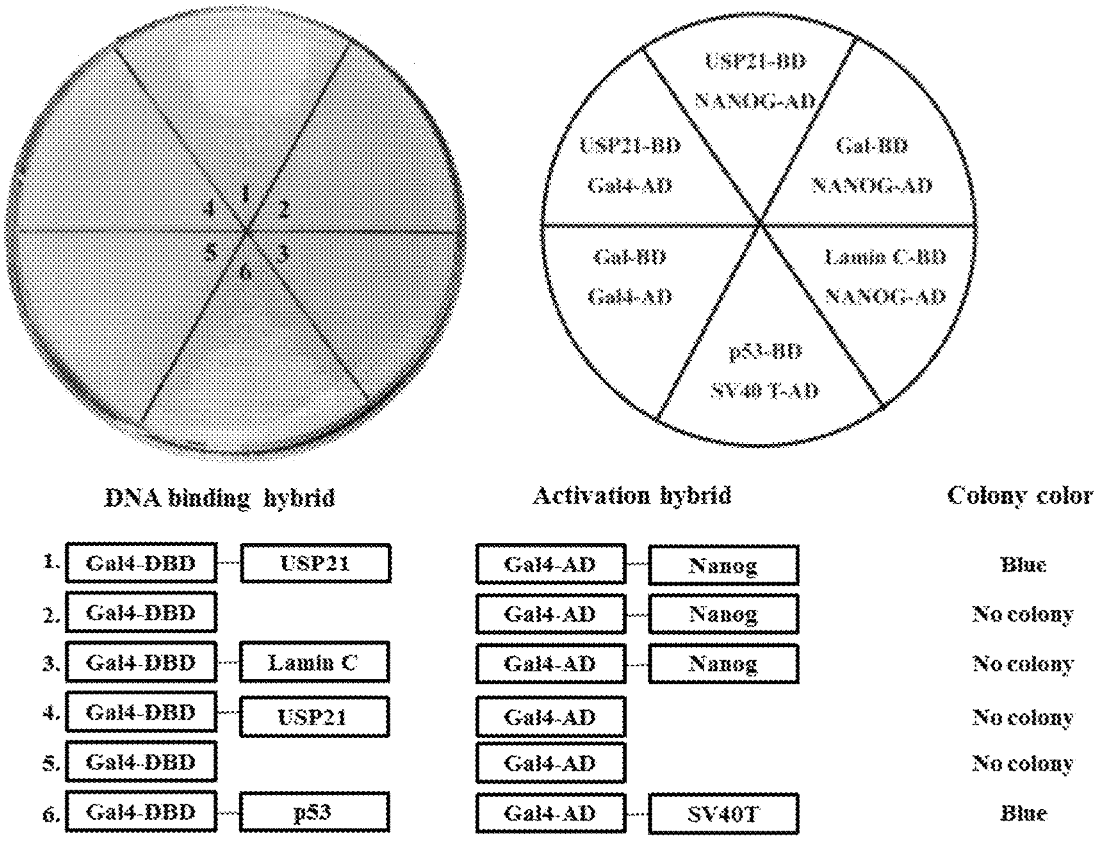
FIG. 3 shows the results obtained by confirming using a negative control and a positive control, after screening deubiquitinating enzymes that bind to NANOG protein with the vector library of the present invention.

FIG. 3 shows the results obtained by screening with the vector library prepared by the present invention. From the results thereof, it can be seen that USP21 and NANOG specifically interact. These results are consistent with the report (Liu et al., USP21 deubiquitylates Nanog to regulate protein stability and stem cell pluripotency, Signal Transduction and Targeted Therapy (2016), 1 e16024).

Figure 4:
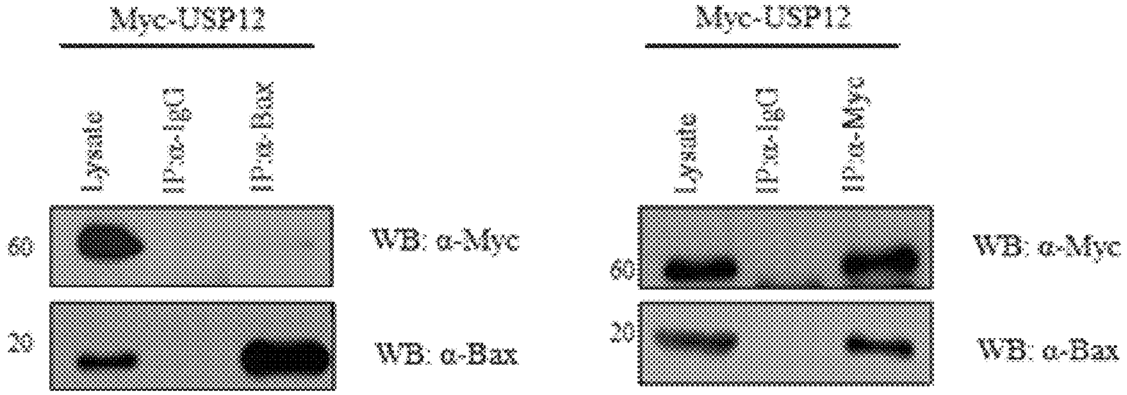
FIG. 4 shows the results obtained by confirming through immunoprecipitation that Bax and USP12 are bound in the cells.
Figure 5:
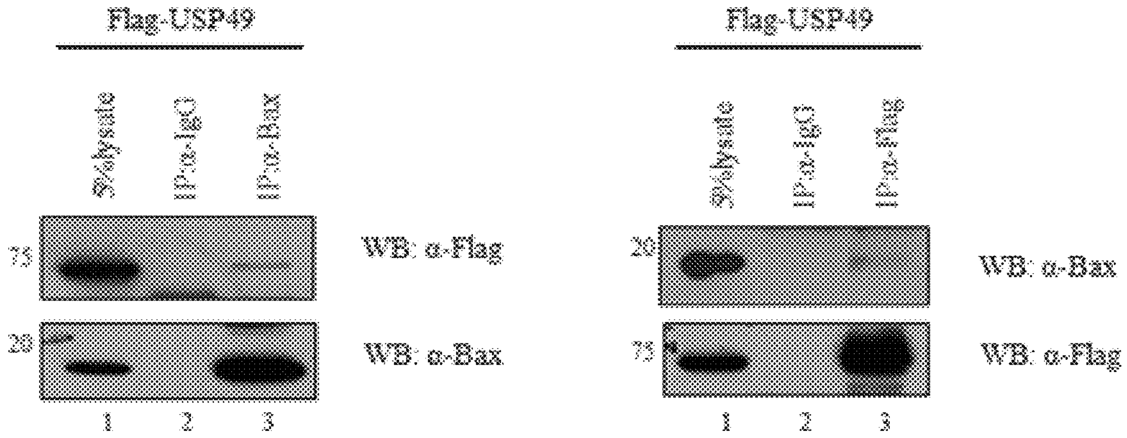
FIG. 5 shows the results obtained by confirming through immunoprecipitation that Bax and USP49 are bound in the cells.

FIG. 4 shows the results obtained by confirming through immunoprecipitation that, among the deubiquitinating enzymes binding to Bax, USP12 binds to Bax in the cells. Myc-USP12 was overexpressed in 293T cells, followed by immunoprecipitation with Myc or Bax antibody. The Bax or Myc-USP12 bound to the immunoprecipitated protein was confirmed by Western blotting. FIG. 5 shows the results obtained by confirming through immunoprecipitation that USP49 and Bax are bound in the cells. Flag-USP49 was overexpressed in 293T cells, followed by immunoprecipitation with Flag or Bax antibody. The Bax or Flag-USP49 bound to the immunoprecipitated protein was confirmed by Western blotting. The results of FIGS. 4 and 5 show that the Bax-binding deubiquitinating enzymes USP12 and USP49 obtained by performing the screening according to the present invention bind to Bax in vivo in cells.

Figure 6:
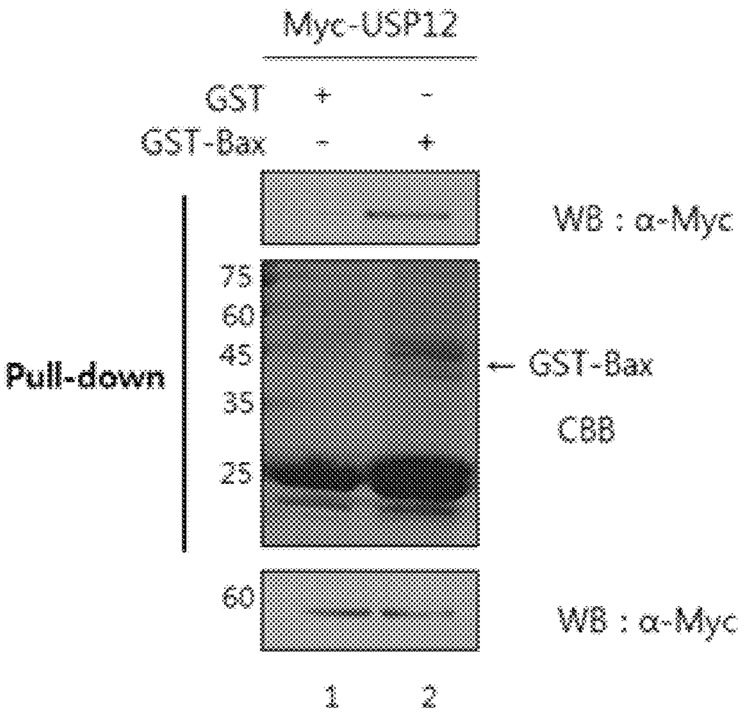
FIG. 6 shows the results obtained by confirming through GST pull-down assay that Bax and USP12 are directly bound.
Figure 7:
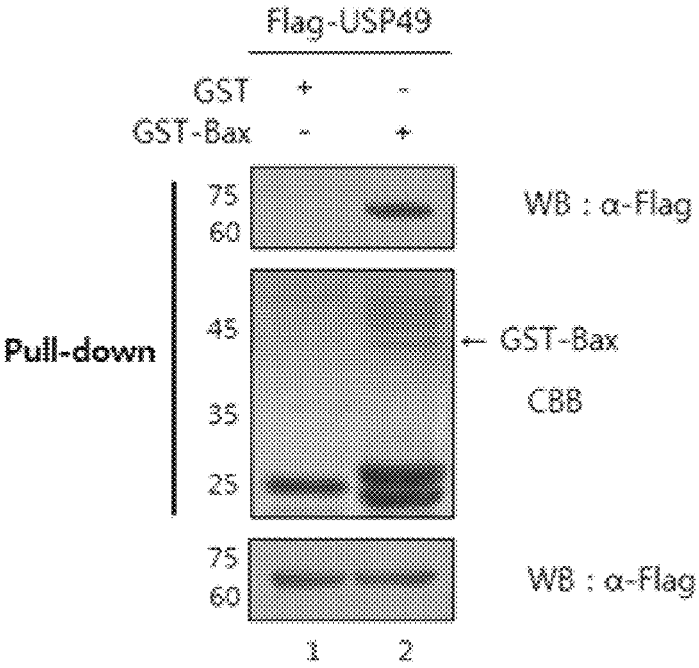
FIG. 7 shows the results obtained by confirming through GST pull-down assay that Bax and USP49 are directly bound.
Figure 8:
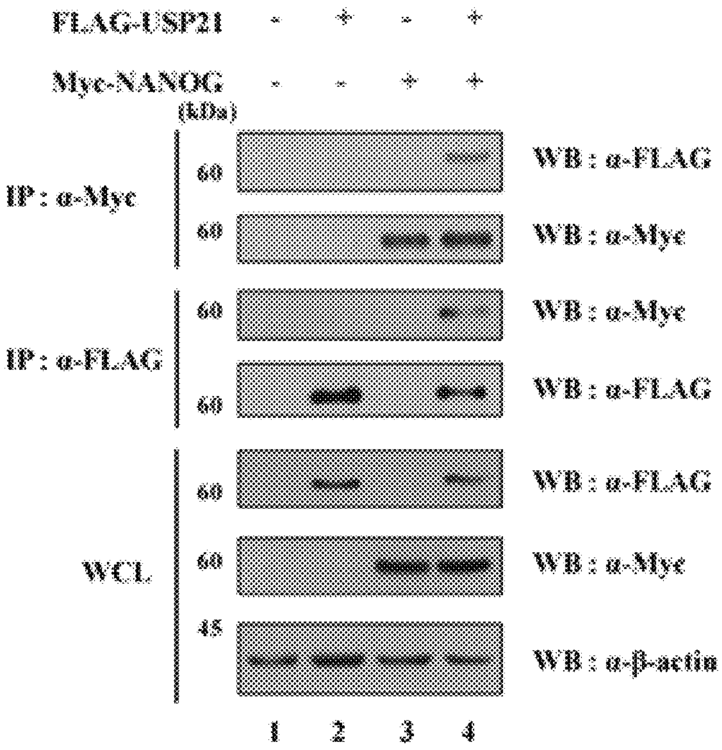
FIG. 8 shows the results obtained by confirming through immunoprecipitation that NANOG and USP21 are bound in the cells.
Figure 9:
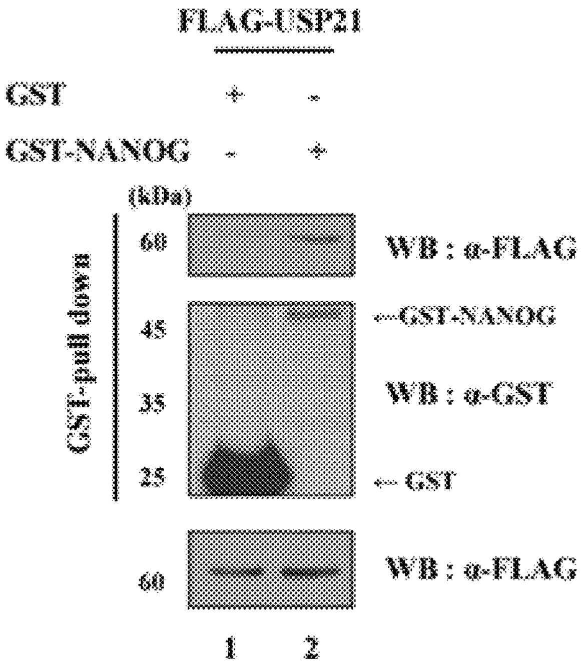
FIG. 9 shows the results obtained by confirming through GST pull-down assay that NANOG and USP21 are directly bound.

FIG. 6 shows the results obtained by confirming through GST pull-down assay that USP12 and Bax are directly bound. The recombinant protein GST-Bax was mixed with the lysate derived from the 293T cells overexpressing Myc-USP12, so as to confirm Myc-USP12 bound to GST-Bax. FIG. 7 shows the result obtained by confirming through GST pull-down assay, as in FIG. 6, that USP49 is directly bound to Bax. FIG. 8 is the results obtained by carrying out immunoprecipitation of the NANOG-binding deubiquitinating enzyme USP21 identified in FIG. 3, which show the interaction of the two proteins. After lysing the 293T cells transfected with Flag-USP21 and NANOG, immunoprecipitation analysis was performed. The analysis revealed that they bind each other. FIG. 9 shows through GST pull-down assay that USP21 and NANOG are directly bound.

Figure 10:
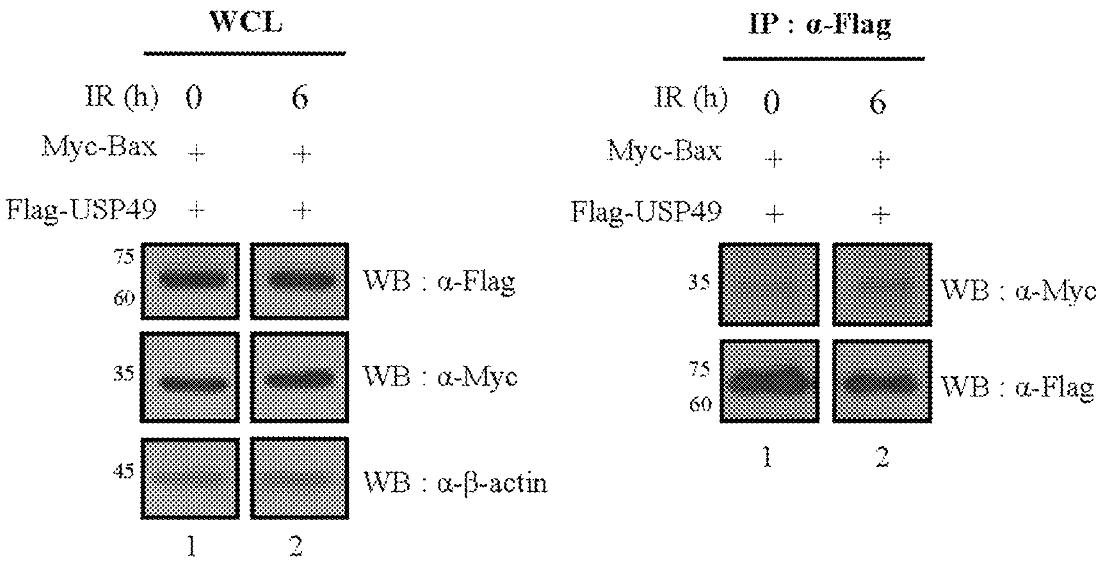
FIG. 10 shows the results obtained by evaluating whether USP49 regulates Bax during IR-induced apoptosis when IR was irradiated after transforming Flag-USP49 and Myc-Bax into HCT116 cells.

FIG. 10 shows the results obtained by evaluating whether USP49 regulates Bax during IR-induced apoptosis when IR was irradiated after transforming Flag-USP49 and Myc-Bax into HCT116 cells. FIG. 11 shows the results obtained by evaluating whether USP49 regulates Bax to promote the apoptosis of cells, through treating the HCT116 cells overexpressed with Flag-USP49 or Myc-Bax with IR irradiation (10 Gy) and then harvesting the cells after 6 hours. When HCT116 cells received IR irradiation, cleavage of PARP1 was increased (lanes 1 and 5 in FIG. 11). Binding affinity of USP49 to Bax in apoptotic cells was increased, indicating that USP49 is involved in IR-induced apoptosis through its interaction with Bax (FIG. 10). Therefore, the present inventors investigated whether USP49 promotes IR-induced apoptosis through deubiquitination of Bax. Overexpression of USP49 in HCT116 cells increased cleavage of PARP1 after IR irradiation (FIG. 11). However, overexpression of USP49 in cells overexpressed with Bax did not further increase the cleavage of PARP1 (FIG. 11). These results suggest that, although USP49 cannot promote IR-induced apoptosis with Bax, USP49 can regulate Bax in a proteasome-independent pathway during IR-induced apoptosis.

3. Discussion

In order to elucidate the causes and solutions of various diseases, various studies are being conducted to establish intracellular signal pathways. The present inventors have focused on deubiquitinating enzymes that regulate the degradation and function of proteins, so as to contribute to the development of effective therapeutics against diseases. It is required to identify deubiquitinating enzymes that interact to regulate cellular mechanisms by regulating certain proteins present in various signal pathways. Therefore, the vector library according to the present invention is expected to be able to provide an efficient help. The present inventors construct a deubiquitinating enzyme screening system by preparing a library capable of expressing each deubiquitinating enzyme in yeast through inserting the genes encoding said deubiquitinating enzyme into the pGBT9 vector having a DNA binding domain. To test this system, cDNA of Bax protein, an apoptosis-associated protein, was used and thus USP1, USP7, USP12, and USP49 are confirmed to be deubiquitinating enzymes binding thereto. Therefore, said system can contribute to the development of therapeutic agents that can effectively induce apoptosis of cancer cells. Among them, it is demonstrated that USP12 and USP49 interact with and bind to the cells in vivo. In addition, the present inventors screened a deubiquitinating enzyme that binds to NANOG protein, and as a result thereof, USP21 was found to be a deubiquitinating enzyme that regulates NANOG. The present inventors also demonstrated that it binds thereto in vivo and in vitro through immunoprecipitation and GST pull-down analysis. In addition, since the results obtained through the screening were consistent with the results of immunoprecipitation and GST-pull down analysis, the screening platform exhibit efficacy. Therefore, the library prepared by the present inventors can efficiently identify the deubiquitinating enzyme binding to the target protein, and can be applied to the development of effective cell therapeutics and anticancer agents through applying the present identifying method.

The invention claimed is:

1. A vector library for yeast two-hybrid screening of a deubiquitinating enzyme that binds to a target protein, comprising:

a vector obtained by inserting a gene encoding a deubiquitinating enzyme USP1 in an empty vector having a DNA-binding domain;

a vector obtained by inserting a gene encoding a deubiquitinating enzyme USP2 in an empty vector having a DNA-binding domain;

a vector obtained by inserting a gene encoding a deubiquitinating enzyme USP3 in an empty vector having a DNA-binding domain;

a vector obtained by inserting a gene encoding a deubiquitinating enzyme USP4 in an empty vector having a DNA-binding domain;

a vector obtained by inserting a gene encoding a deubiquitinating enzyme USP5 in an empty vector having a DNA-binding domain;

a vector obtained by inserting a gene encoding a deubiquitinating enzyme USP6 in an empty vector having a DNA-binding domain;

a vector obtained by inserting a gene encoding a deubiquitinating enzyme USP7 in an empty vector having a DNA-binding domain;

a vector obtained by inserting a gene encoding a deubiquitinating enzyme USP8 in an empty vector having a DNA-binding domain;

a vector obtained by inserting a gene encoding a deubiquitinating enzyme USP10 in an empty vector having a DNA-binding domain;

a vector obtained by inserting a gene encoding a deubiquitinating enzyme USP11 in an empty vector having a DNA-binding domain;

a vector obtained by inserting a gene encoding a deubiquitinating enzyme USP12 in an empty vector having a DNA-binding domain;

a vector obtained by inserting a gene encoding a deubiquitinating enzyme USP14 in an empty vector having a DNA-binding domain;

a vector obtained by inserting a gene encoding a deubiquitinating enzyme USP15 in an empty vector having a DNA-binding domain;

a vector obtained by inserting a gene encoding a deubiquitinating enzyme USP16 in an empty vector having a DNA-binding domain;

a vector obtained by inserting a gene encoding a deubiquitinating enzyme USP17 in an empty vector having a DNA-binding domain;

a vector obtained by inserting a gene encoding a deubiquitinating enzyme USP18 in an empty vector having a DNA-binding domain;

a vector obtained by inserting a gene encoding a deubiquitinating enzyme USP19 in an empty vector having a DNA-binding domain;

a vector obtained by inserting a gene encoding a deubiquitinating enzyme USP20 in an empty vector having a DNA-binding domain;

a vector obtained by inserting a gene encoding a deubiquitinating enzyme USP21 in an empty vector having a DNA-binding domain;

a vector obtained by inserting a gene encoding a deubiquitinating enzyme USP25 in an empty vector having a DNA-binding domain;

a vector obtained by inserting a gene encoding a deubiquitinating enzyme USP28 in an empty vector having a DNA-binding domain;

a vector obtained by inserting a gene encoding a deubiquitinating enzyme USP30 in an empty vector having a DNA-binding domain;

a vector obtained by inserting a gene encoding a deubiquitinating enzyme USP33 in an empty vector having a DNA-binding domain;

a vector obtained by inserting a gene encoding a deubiquitinating enzyme USP34 in an empty vector having a DNA-binding domain;

a vector obtained by inserting a gene encoding a deubiquitinating enzyme USP35 in an empty vector having a DNA-binding domain;

a vector obtained by inserting a gene encoding a deubiquitinating enzyme USP36 in an empty vector having a DNA-binding domain;

a vector obtained by inserting a gene encoding a deubiquitinating enzyme USP37 in an empty vector having a DNA-binding domain;

a vector obtained by inserting a gene encoding a deubiquitinating enzyme USP38 in an empty vector having a DNA-binding domain;

a vector obtained by inserting a gene encoding a deubiquitinating enzyme USP39 in an empty vector having a DNA-binding domain;

a vector obtained by inserting a gene encoding a deubiquitinating enzyme USP44 in an empty vector having a DNA-binding domain;

a vector obtained by inserting a gene encoding a deubiquitinating enzyme USP46 in an empty vector having a DNA-binding domain; and a vector obtained by inserting a gene encoding a deubiquitinating enzyme USP49 in an empty vector having a DNA-binding domain.

2. The vector library according to claim 1, wherein the empty vector having a DNA-binding domain is a pGBT9 vector.

3. A method for identifying a deubiquitinating enzyme binding to a target protein, the method comprising:

(a) inserting a gene encoding a target protein into an empty vector having a transcription activation domain to prepare a vector;

(b) transforming yeasts with each vector of the vector library according to claim 1 and the vector prepared in Step (a); and (c) culturing the yeasts obtained in Step (b) in a medium containing X-gal and free of tryptophan and leucine.

4. The method according to claim 3, wherein the empty vector having a transcription activation domain is a pGAD424 vector.

* * * * *

SEQUENCE LISTING

```
Sequence total quantity: 89
SEQ ID NO: 1            moltype = DNA  length = 2358
FEATURE                 Location/Qualifiers
misc_feature            1..2358
                        note = other DNA
source                  1..2358
                        mol_type = other DNA
                        organism = Homo sapiens
SEQUENCE: 1
atgcctggtg tcatacctag tgaaagtaat ggactttcaa gaggtagccc ttcaaagaaa  60
aacagacttt ccttaaagtt ttttcagaaa aaggaaacta agagagcttt ggatttcaca  120
gattctcaag aaaatgaaga aaaagcttct gaatatagag catctgaaat tgatcaagtt  180
gttcctgcag cacagtcttc acctataaac tgtgagaaga gagaaaactt gttaccattt  240
gtgggactga ataatctcgg caatacttgc tatcttaata gtatacttca ggtattatat  300
```

-continued

```
ttttgtcccg gttttaaatc tggagtaaag cacttattta atattatttc aaggaagaaa  360
gaagctctaa aggatgaagc caatcaaaaa gacaagggaa attgcaaaga agattctttg  420
gcaagttatg aattgatatg cagtttacag tccttaatca tttcggttga acagctccag  480
gctagttttc tcttaaatcc agagaaatat actgatgaac ttgccactca gccaaggcga  540
ctgcttaaca cactgaggga actcaaccct atgtatgaag gatatctaca gcatgatgca  600
caggaagtat tacaatgtat tttgggaaac attcaagaaa catgccaact cctaaaaaaa  660
gaagaagtaa aaaatgtggc agaattacct actaaggtag aagaaatacc tcatccgaaa  720
gaggaaatga atggtattaa cagcatagag atggacagta tgaggcattc tgaagacttt  780
aaagagaaac tcccaaaagg aaatgggaaa agaaaaagtg acactgaatt tggtaacatg  840
aagaaaaaag ttaaattatc caaggaacac cagtcattgg aagagaacca gagacaaact  900
agatcaaaaa gaaaagctac aagtgataca ttagagagtc ctcctaaaat aattcccaag  960
tatatttctg aaaatgagag tccaagaccc tcacaaaaga aatcaagagt taaaataaat  1020
tggttaaagt ctgcaactaa gcaacccagc attctttcta aattttgtag tctgggaaaa  1080
ataacaacaa accaaggagt caaaggacaa tctaaagaaa atgaatgtga tcctgaagag  1140
gacttgggga agtgtgaaag tgataacaca actaatggtt gtggacttga atctccagga  1200
aatactgtta cacctgtaaa tgttaatgaa gttaaaccca taaacaaagg tgaagaacaa  1260
attggtttg agctagtgga gaaattattt caaggtcagc tggtattaag gacgcgttgc  1320
ttggaatgtg aaagtttaac agaaagaaga gaagattttc aagacatcag tgtgccagta  1380
caagaagatg agctttccaa agtagaggag agttctgaaa tttctccaga gccaaaaaca  1440
gaaatgaaga ccctgagatg ggcaatttca caatttgctt cagtagaaag gattgtagga  1500
gaagataaat atttctgtga aaactgccat cattatactg aagctgaacg aagtcttttg  1560
tttgacaaaa tgcctgaagt tataactatt catttgaagt gctttgctgc tagtggtttg  1620
gagtttgatt gttatggtgg tggactttcc aagatcaaca ctcctttatt gacacctctt  1680
aaattgtcac tagaagaatg gagcacaaag ccaactaacg acagctatgg attatttgcg  1740
gttgtgatgc atagtggcat tacaattagt agtgggcatt acactgcttc tgttaaagtc  1800
actgacctta acagtttaga actagataaa ggaaattttg tggttgacca aatgtgtgaa  1860
ataggtaagc cagaaccatt gaatgaggag gaagcaaggg gtgtggttga gaattataat  1920
gatgaagaag tgtcaattag agttggtgga aatacacagc caagtaaagt tttgaacaaa  1980
aaaaatgtag aagctattgg acttcttgga ggacaaaaga gcaaagcaga ttatgagcta  2040
tacaacaaag cctctaatcc tgataaggtt gctagtacag cgtttgctga aaatagaaat  2100
tctgagacta gtgatactac tgggacccat gaatctgata gaaacaagga atccagtgac  2160
caaacaggca ttaatattag tggatttgag aacaaaattt catacgtagt gcaaagctta  2220
aaggagtatg aggggaagtg gttgcttttt gatgattctg aagtcaaagt tactgaagag  2280
aaggactttc tgaattctct ttccccttct acatctccta cttctactcc ttacttgcta  2340
ttttataaga aattatag                                                2358

SEQ ID NO: 2           moltype = AA  length = 785
FEATURE                Location/Qualifiers
source                 1..785
                       mol_type = protein
                       organism = Homo sapiens
SEQUENCE: 2
MPGVIPSESN GLSRGSPSKK NRLSLKFFQK KETKRALDFT DSQENEEKAS EYRASEIDQV  60
VPAAQSSPIN CEKRENLLPF VGLNNLGNTC YLNSILQVLY FCPGFKSGVK HLFNIISRKK  120
EALKDEANQK DKGNCKEDSL ASYELICSLQ SLIISVEQLQ ASFLLNPEKY TDELATQPRR  180
LLNTLRELNP MYEGYLQHDA QEVLQCILGN IQETCQLLKK EEVKNVAELP TKVEEIPHPK  240
EEMNGINSIE MDSMRHSEDF KEKLPKGNGK RKSDTEFGNM KKKVKLSKEH QSLEENQRQT  300
RSKRKATSDT LESPPKIIPK YISENESPRP SQKKSRVKIN WLKSATKQPS ILSKFCSLGK  360
ITTNQGVKGQ SKENECDPEE DLGKCESDNT TNGCGLESPG NTVTPVNVNE VKPINKGEEQ  420
IGFELVEKLF QGQLVLRTRC LECESLTERR EDFQDISVPV QEDELSKVEE SSEISPEPKT  480
EMKTLRWAIS QFASVERIVG EDKYFCENCH HYTEAERSLL FDKMPEVITI HLKCFAASGL  540
EFDCYGGGLS KINTPLLTPL KLSLEEWSTK PTNDSYGLFA VVMHSGITIS SGHYTASVKV  600
TDLNSLELDK GNFVVDQMCE IGKPEPLNEE EARGVVENYN DEEVSIRVGG NTQPSKVLNK  660
KNVEAIGLLG GQKSKADYEL YNKASNPDKV ASTAFAENRN SETSDTTGTH ESDRNKESSD  720
QTGINISGFE NKISYVVQSL KEYEGKWLLF DDSEVKVTEE KDFLNSLSPS TSPTSTPYLL  780
FYKKL                                                              785

SEQ ID NO: 3           moltype = DNA  length = 1818
FEATURE                Location/Qualifiers
misc_feature           1..1818
                       note = Other DNA
source                 1..1818
                       mol_type = other DNA
                       organism = Homo sapiens
SEQUENCE: 3
atgtcccagc tctcctccac cctgaagcgc tacacagaat cggcccgcta cacagatgcc  60
cactatgcca agtcgggcta tggtgcctac accccatcct cctatggggc caatctggct  120
gcctccttac tggagaagga gaaacttggt ttcaagccgg tccccaccag cagcttcctc  180
acccgtcccc gtacctatgg cccctcctcc ctcctggact atgaccgggg ccgccccctg  240
ctgagacccg acatcactgg gggtggtaag cgggcagaga gccagacccg gggtactgag  300
cggcctttag gcagtggcct cagcgggggc agcggattcc cttatggagt gaccaacaac  360
tgcctcagct acctgcccat caatgcctat gaccaggggg tgaccctaac ccagaagctg  420
gacagccaat cagacctggc ccgggatttc tccagcctcc ggacctcaga tagctaccgg  480
atagacccca ggaacctggg ccgcagcccc atgctggccc ggacgcgcaa ggagctctgc  540
accctgcagg ggctctacca gacagccagc tgccctgaat acctggtcga ctacctggag  600
aactatggtc gcaagggcag tgcatctcag gtgccctccc aggcccctcc ctcacgagtc  660
cctgaaatca tcagcccaac ctaccgaccc attggccgct acacgctgtg ggagacggga  720
aagggtcagg cccctgggcc cagccgctcc agctccccgg gaagagacgg catgaattct  780
aagagtgccc agggtctggc tggtcttcga aaccttggga acacgtgctt catgaactca  840
```

-continued

```
attctgcagt gcctgagcaa cactcgggag ttgagagatt actgcctcca gaggctctac  900
atgcgggacc tgcaccacgg cagcaatgca cacacagccc tcgtggaaga gtttgcaaaa  960
ctaattcaga ccatatggac ttcatccccc aatgatgtgg tgagcccatc tgagttcaag  1020
acccagatcc agagatatgc accgcgcttt gttggctata atcagcagga tgctcaggag  1080
ttccttcgct ttcttctgga tggctccat aacgaggtga accgagtgac actgagacct  1140
aagtccaacc ctgagaacct cgatcatctt cctgatgacg agaaaggccg acagatgtgg  1200
agaaaatatc tagaacggga agacagtagg atcggggatc tctttgttgg gcagctaaag  1260
agctcgctga cgtgtacaga ttgtggttac tgttctacgg tcttcgaccc cttctgggac  1320
ctctcactgc ccattgctaa gcgaggttat cctgaggtga cattaatgga ctgcatgagg  1380
ctcttcacca aagaggatgt gcttgatgga gatgaaaagc caacatgctg tcgctgccga  1440
ggcagaaaac ggtgtataaa gaagttctcc atccagaggt tcccaaagat cttggtgctc  1500
catctgaagc ggttctcaga atccaggatc cgaaccagca agctcacaac atttgtgaac  1560
ttcccccctaa gagacctgga cttaagagaa tttgcctcag aaaacaccaa ccatgctgtt  1620
tacaacctgt acgctgtgtc caatcactcc ggaaccacca tgggtggcca ctatacagcc  1680
tactgtcgca gtccagggac aggagaatgg cacactttca acgactccag cgtcactccc  1740
atgtcctcca gccaagtgcg caccagcgac gcctacctgc tcttctacga actggccagc  1800
ccgccctccc gaatgtag                                               1818

SEQ ID NO: 4            moltype = AA  length = 605
FEATURE                 Location/Qualifiers
source                  1..605
                        mol_type = protein
                        organism = Homo sapiens
SEQUENCE: 4
MSQLSSTLKR YTESARYTDA HYAKSGYGAY TPSSYGANLA ASLLEKEKLG FKPVPTSSFL  60
TRPRTYGPSS LLDYDRGRPL LRPDITGGGK RAESQTRGTE RPLGSGLSGG SGFPYGVTNN  120
CLSYLPINAY DQGVTLTQKL DSQSDLARDF SSLRTSDSYR IDPRNLGRSP MLARTRKELC  180
TLQGLYQTAS CPEYLVDYLE NYGRKGSASQ VPSQAPPSRV PEIISPTYRP IGRYTLWETG  240
KGQAPGPSRS SSPGRDGMNS KSAQGLAGLR NLGNTCFMNS ILQCLSNTRE LRDYCLQRLY  300
MRDLHHGSNA HTALVEEFAK LIQTIWTSSP NDVVSPSEFK TQIQRYAPRF VGYNQQDAQE  360
FLRFLLDGLH NEVNRVTLRP KSNPENLDHL PDDEKGRQMW RKYLEREDSR IGDLFVGQLK  420
SSLTCTDCGY CSTVFDPFWD LSLPIAKRGY PEVTLMDCMR LFTKEDVLDG DEKPTCCRCR  480
GRKRCIKKFS IQRFPKILVL HLKRFSESRI RTSKLTTFVN FPLRDLDLRE FASENTNHAV  540
YNLYAVSNHS GTTMGGHYTA YCRSPGTGEW HTFNDSSVTP MSSSQVRTSD AYLLFYELAS  600
PPSRM                                                             605

SEQ ID NO: 5            moltype = DNA  length = 1566
FEATURE                 Location/Qualifiers
misc_feature            1..1566
                        note = Other DNA
source                  1..1566
                        mol_type = other DNA
                        organism = Homo sapiens
SEQUENCE: 5
atggagtgtc cacacctgag ctccagcgtc tgcattgctc cggactcagc caagttcccc  60
aacggctccc cgtcgtcctg gtgctgcagc gtgtgccggt ccaacaaaag cccttgggtc  120
tgtttgactt gttcaagtgt ccactgtgga aggtatgtga atggccatgc aaaaaaacat  180
tatgaagatg cacaagtacc tttaaccaac cataagaaat cagaaaagca agataaagtt  240
cagcacacag tatgtatgga ttgcagtagc tacagtacat actgttatcg ctgtgatgat  300
tttgtggtta atgacaccaa gctgggactg gtacagaaag tcagagaaca cttacagaac  360
ttggaaaact cagctttcac agctgacagg cataagaaaa gaaaactttt ggaaaactca  420
acactaaaca gcaagttatt aaaagtaaat ggaagcacca ctgccatttg tgccacaggc  480
cttcggaatt tggggaacac atgtttcatg aatgccatcc ttcagtcact cagtaacatt  540
gagcagtttt gctgttattt caaagaactg cccgccgtgg agttaaggaa tgggaaaaca  600
gcaggaaggc ggacatacca caccaggagc caaggggata acaatgtgtc tttggtagaa  660
gagtttagaa agacactctg tgctttatgg caaggcagcc agactgcatt tagcccagag  720
tccttatttt atgttgtttg gaagattatg ccaaacttta ggggctatca acagcaggac  780
gcccatgaat tcaatgcgct accttttgga ccacctacac ttgggaactt cagggcggtt  840
tcaacggtgt ttcccgctca gcaattctgc aggagaattc tactctgtct gcaagtaaac  900
aagtgttgca taaatggagc atctactgtt gtcacggcta tattcggagg cattctccaa  960
aatgaggtta actgcctcat atgtgggaca gaatctagaa agtttgatcc attcctagac  1020
ctttcattag atattccaag tcagttcaga agtaagcgct ctaagaatca agaaaatgga  1080
ccagtttgtt cgttacgaga ttgtcttcgc agttttaccg acttagaaga acttgatgag  1140
acagagttat atatgtgcca taaatgcaaa aagaaacaaa agtccacaaa aaagttttgg  1200
attcaaaaac tacccaaggt gctatgctta catttgaaaa gatttcattg gacagcatat  1260
ttaagaaata aagttgatac atacgtagaa tttccactga gaggcctaga catgaaatgg  1320
tacttactag agcctgagaa cagtggcccg gagagctgcc tgtatgacct cgccgctgtg  1380
gtggtgcacc atggttccgg ggttggttct ggacattaca cagcatacgc aactcacgaa  1440
ggccgctggt tccacttcaa tgacagtact gtaacactga ctgacgagga gactgtggtg  1500
aaggcgaagg cctacatcct tttctacgtg gaacaccagg ccaaagctgg atcggataaa  1560
ctttaa                                                            1566

SEQ ID NO: 6            moltype = AA  length = 521
FEATURE                 Location/Qualifiers
source                  1..521
                        mol_type = protein
                        organism = Homo sapiens
SEQUENCE: 6
MECPHLSSSV CIAPDSAKFP NGSPSSWCCS VCRSNKSPWV CLTCSSVHCG RYVNGHAKKH  60
```

```
YEDAQVPLTN HKKSEKQDKV QHTVCMDCSS YSTYCYRCDD FVVNDTKLGL VQKVREHLQN  120
LENSAFTADR HKKRKLLENS TLNSKLLKVN GSTTAICATG LRNLGNTCFM NAILQSLSNI  180
EQFCCYFKEL PAVELRNGKT AGRRTYHTRS QGDNNVSLVE EFRKTLCALW QGSQTAFSPE  240
SLFYVVWKIM PNFRGYQQQD AHEFNALPFG PPTLGNFRAV STVFPAQQFC RRILLCLQVN  300
KCCINGASTV VTAIFGGILQ NEVNCLICGT ESRKFDPFLD LSLDIPSQFR SKRSKNQENG  360
PVCSLRDCLR SFTDLEELDE TELYMCHKCK KKQKSTKKFW IQKLPKVLCL HLKRFHWTAY  420
LRNKVDTYVE FPLRGLDMKW YLLEPENSGP ESCLYDLAAV VVHHGSGVGS GHYTAYATHE  480
GRWFHFNDST VTLTDEETVV KAKAYILFYV EHQAKAGSDK L                      521

SEQ ID NO: 7           moltype = DNA  length = 2892
FEATURE                Location/Qualifiers
misc_feature           1..2892
                       note = Other DNA
source                 1..2892
                       mol_type = other DNA
                       organism = Homo sapiens
SEQUENCE: 7
atggcggaag gtggaggctg ccgtgagcga ccggatgcgg agactcagaa gtccgagctt  60
ggacccttaa tgaggaccac actccaacgc ggggcgcagt ggtatcttat tgacagccgg  120
tggttcaagc agtggaagaa gtatgtgggc tttgacagct gggacatgta caatgtgggt  180
gaacataacc tatttcctgg cccaatagac aactctgggc tattttcaga tcctgagagt  240
cagaccttga aagaacactt aattgatgaa ttggactatg tattggtccc taccgaggcg  300
tggaataaac tactaaactg gtacggctgt gtagaaggcc agcaacccat cgtcagaaaa  360
gttgtggagc atggcctgtt tgtcaagcac tgcaaagtcg aggtgtattt gctggaactg  420
aagctctgtg agaacagtga ccccaccaat gtgctgagtt gccatttcag caaggcagac  480
accattgcaa ccatcgagaa agagatgcgg aagctattca acatccctgc ggagcgtgaa  540
acacggctct ggaacaaata catgagcaac acctacgagc agttgagcaa gctagacaac  600
actgtccagg atgctgggct ataccagggt caggtgctag taattgagcc tcaaaatgaa  660
gatggcacat ggcccaggca gaccttgcag tcaaaatcaa gcactgcgcc tagcagaaat  720
tttactacct ctccaaaatc atcagcaagt ccctattcct cagtgtctgc ctctctcatt  780
gcaaatggtg atagcactag cacctgtggg atgcacagtt ccggtgtcag caggggtgga  840
tctggctttt ctgcttcgta taattgtcag gagccaccat cctctcatat acaacctggg  900
ctctgtggac ttggaaacct gggaaacacc tgcttcatga actccgcttt gcagtgtttg  960
agcaacactg caccactgac tgactacttt ctcaaagatg agtatgaagc cgaaatcaac  1020
agagacaacc ctctggggat gaaaggggaa attgcagaag cctatgctga actcattaag  1080
cagatgtggt ctggaaggga cgcccatgtg gcacctcgca tgttcaaaac tcaagtagga  1140
cgttttgctc ctcaattttc tggctaccag caacaagatt ctcaggagct gctggccttt  1200
cttctagatg gattgcatga agatctgaac cgggtaaaga aaaagcccta cttggagctg  1260
aaggatgcca atgggcggcc agatgcggtg gtggcaaagg aagcctggga gaatcacagg  1320
ttgaggaatg attctgtgat tgtggatact ttccatggcc tcttcaaatc tactttgggt  1380
tgcccagaat gtgctaaggt ttctgtgacc tttgacccat tttgctatct aacgctgcca  1440
ctgcccttga agaaagatcg agttatggag gttttcctgg ttcctgctga ccctcactgc  1500
agacctactc agtaccgtgt gactgtgccg ctgatggggg ctgtgtccga cctgtgcgag  1560
gctctctcca ggctgtctgg cattgctgca gaaaatatgg tggtcgcaga tgtgtataat  1620
caccgattcc acaaaatttt ccaaatggat gaaggtttaa accacatcat gcctcgggat  1680
gacattttcg tgtacgaggt ctgcagcact tccgtggatg gctcggaatg tgtcacgctt  1740
ccagtctact tcagggagag gaagtccagg ccatcaagca cttcctccgc atcagcgcta  1800
tatgggcagc cactattgct ttctgtcccc aagcacaagt taacccttga gtctttgtac  1860
caggctgttt gtgatcgtat cagccgctat gtgaaacagc ctttacctga tgagtttggc  1920
agctcaccct tggagccagg ggcctgcaat ggctccagga acagctgtga aggagaagat  1980
gaggaagaaa tggagcatca ggaagaaggc aaagagcagc tttcagaaac agaaggcagt  2040
ggggaagatg agccaggaaa tgaccccagt gagaccaccc aaaagaagat caaaggccag  2100
ccctgcccaa aaaggctttt taccttcagt cttgtgaact cctatggaac agctgacata  2160
aattcacttg cagctgatgg aaaactactt aaactcaact ctcgatctac actggccatg  2220
gattgggaca gtgaaactcg gagactttac tatgatgagc aagaatctga ggcctacgag  2280
aagcatgtga gcatgttgca gcctcagaag aagaagaaga ccacagtggc cctgagagac  2340
tgcatcgagc tcttcaccac catggagacc cttggggagc atgacccctg gtactgtccc  2400
aactgtaaga agcatcaaca ggccacaaaa aagtttgacc tatggtcctt gcccaagatc  2460
ctggtggtcc acctcaaacg tttctcctac aacagatact ggagggataa gctcgacaca  2520
gtcgtagaat tcccaatcag agggctgaac atgtccgagt ttgtctgtaa cctgtcagca  2580
aggccttatg tgtacgacct cattgccgtg tccaatcatt atggagccat ggggggttggc  2640
cactacactg catatgcgaa gaacaaactg aatggtaaat ggtattactt tgatgatagc  2700
aacgtgtccc tggcctctga ggatcagata gtgactaaag cagcttatgt gctattttac  2760
caacgtcgag atgatgaatt ttataagaca ccttcactta gcagttctgg ttcctctgat  2820
ggagggacac gaccaagcag ctctcagcag ggctttgggg atgatgaggc ttgcagcatg  2880
gacaccaact aa                                                      2892

SEQ ID NO: 8           moltype = AA  length = 963
FEATURE                Location/Qualifiers
source                 1..963
                       mol_type = protein
                       organism = Homo sapiens
SEQUENCE: 8
MAEGGGCRER PDAETQKSEL GPLMRTTLQR GAQWYLIDSR WFKQWKKYVG FDSWDMYNVG  60
EHNLFPGPID NSGLFSDPES QTLKEHLIDE LDYVLVPTEA WNKLLNWYGC VEGQQPIVRK  120
VVEHGLFVKH CKVEVYLLEL KLCENSDPTN VLSCHFSKAD TIATIEKEMR KLFNIPAERE  180
TRLWNKYMSN TYEQLSKLDN TVQDAGLYQG QVLVIEPQNE DGTWPRQTLQ SKSSTAPSRN  240
FTTSPKSSAS PYSSVSASLI ANGDSTSTCG MHSSGVSRGG SGFSASYNCQ EPPSSHIQPG  300
LCGLGNLGNT CFMNSALQCL SNTAPLTDYF LKDEYEAEIN RDNPLGMKGE IAEAYAELIK  360
```

-continued

```
QMWSGRDAHV APRMFKTQVG RFAPQFSGYQ QQDSQELLAF LLDGLHEDLN RVKKKPYLEL  420
KDANGRPDAV VAKEAWENHR LRNDSVIVDT FHGLFKSTLG CPECAKVSVT FDPFCYLTLP  480
LPLKKDRVME VFLVPADPHC RPTQYRVTVP LMGAVSDLCE ALSRLSGIAA ENMVVADVYN  540
HRFHKIFQMD EGLNHIMPRD DIFVYEVCST SVDGSECVTL PVYFRERKSR PSSTSSASAL  600
YGQPLLLSVP KHKLTLESLY QAVCDRISRY VKQPLPDEFG SSPLEPGACN GSRNSCEGED  660
EEEMEHQEEG KEQLSETEGS GEDEPGNDPS ETTQKKIKGQ PCPKRLFTFS LVNSYGTADI  720
NSLAADGKLL KLNSRSTLAM DWDSETRRLY YDEQESEAYE KHVSMLQPQK KKTTVALRD   780
CIELFTTMET LGEHDPWYCP NCKKHQQATK KFDLWSLPKI LVVHLKRFSY NRYWRDKLDT  840
VVEFPIRGLN MSEFVCNLSA RPYVYDLIAV SNHYGAMGVG HYTAYAKNKL NGKWYYFDDS  900
NVSLASEDQI VTKAAYVLFY QRRDDEFYKT PSLSSSGSSD GGTRPSSSQQ GFGDDEACSM  960
DTN                                                                963

SEQ ID NO: 9           moltype = DNA  length = 2508
FEATURE                Location/Qualifiers
misc_feature           1..2508
                       note = Other DNA
source                 1..2508
                       mol_type = other DNA
                       organism = Homo sapiens
SEQUENCE: 9
atggcggagc tgagtgagga ggcgctgctg tcagtattac cgacgatccg ggtccctaag  60
gctggagacc gggtccacaa agacgagtgc gccttctcct tcgacacgcc ggagtctgag  120
gggggcctct acatctgtat gaacacgttt ctgggctttg ggaaacagta tgtggagaga  180
catttcaata agaccggcca gcgagtctac ttgcacctcc ggcggacccg gcgcccgaaa  240
gaggaggacc ctgctacagg cactggagac ccacccccgga agaagcccac gcggctggct  300
attggtgttg aaggcggatt tgaccttagc gaggagaagt ttgaattaga cgaggatgtg  360
aagattgtca ttttgccaga ttacctggag attgcccggg atggactggg gggactgcct  420
gacattgtca gagatcgggt gaccagtgca gtggaggccc tactgtcggc cgactcagcc  480
tcccgcaagc aggaggtgca ggcatgggat ggggaagtac ggcaggtgtc taagcatgcc  540
ttcagcctca agcagttgga caaccctgct cgaatccctc cctgtggctg gaagtgctcc  600
aagtgtgaca tgagagagaa cctgtggctc aacctgactg atggctccat cctctgtggg  660
cgacgctact tcgatggcag tgggggcaac aaccacgctg tggagcacta ccgagagaca  720
ggctacccgt tagctgtcaa gctgggcacc atcacccctg atggagctga cgtgtactca  780
tatgatgagg atgacatggt cctggacccc agcctggctg agcacctgtc ccacttcggc  840
atcgacatgc tgaagatgca gaagacagac aagacgatga ctgagttgga gatagacatg  900
aaccagcgga ttggtgaatg ggagctgatc caggagtcag gtgtgccact caagcccctg  960
tttgggcctg gctacacagg catccggaac ctgggtaaca gctgctacct caactctgtg  1020
gtccaggtgc tcttcagcat ccctgacttc cagaggaagt atgtggataa gctggagaag  1080
atcttccaga atgccccgac ggaccctacc caggatttca gcacccaggt ggccaagctg  1140
ggccatggcc ttctctccgg ggagtattcc aagccagtac cggagtcggg cgatggggag  1200
cgggtgccag aacagaagga agttcaagat ggcattgccc ctcggatgtt caaggccctc  1260
atcggcaagg gccaccctga attctccacc aaccggcagc aggatgccca ggagttcttc  1320
cttcacctta tcaacatggt ggagaggaat tgccggagct ctgaaaatcc taatgaagtg  1380
ttccgcttct tggtggagga aaagatcaag tgcctggcca cagagaaggt gaagtacacc  1440
cagcgagttg actacatcat gcagctgcct gtgcccatgg atgcagccct taacaaagag  1500
gagcttctgg agtacgagga gaagaagcgg caagccgaag aggagaagat ggcactgcca  1560
gaactggttc gggcccaggt gcccttcagc tcttgcctgg aggcctacgg ggcccctgag  1620
caggtcgatg acttctggag cacggccctg caggccaagt cagtagctgt caagaccaca  1680
cgatttgcct cattccctga ctacctggtc atccagatca agaagttcac cttcggctta  1740
gactgggtgc ccaagaaact ggatgtgtcc atcgagatgc cagaggagct cgacatctcc  1800
cagttgaggg gcacagggct gcagcccgga gaggaggagc tgccagacat tgccccaccc  1860
ctggtcactc cggatgagcc caaagcgccc atgctggatg aatcagtcat catccagctg  1920
gtggagatgg gattccctat ggacgcctgc cgcaaagctg tctactacac gggcaacagc  1980
ggggctgagg ccgccatgaa ctgggtcatg tcacacatgg atgatccaga ttttgcaaac  2040
cccctcatcc tgcctggctc tagtgggccg ggctccacaa gcgcagcagc cgaccccccct  2100
cctgaggact gtgtgaccac cattgtctcc atgggcttct cccgggacca ggccttgaaa  2160
gcgctgcggg ccacgaacaa tagtttagaa cgggctgtgg actggatctt cagtcacatt  2220
gacgacctgg atgctgaagc tgccatggac atctcagagg gccgctcagc tgccgactcc  2280
atctctgagt ctgtgccagt gggacctaaa gtccgggatg gtcctggaaa gtatcagctc  2340
tttgccttca ttagtcacat gggcacctct accatgtgtg gtcactacgt ctgccacatc  2400
aagaaagaag gcagatgggt gatctacaat gaccagaaag tgtgtgcctc cgagaagccg  2460
cccaaggacc tgggctacat ctacttctac cagagagtgg ccagctaa               2508

SEQ ID NO: 10          moltype = AA  length = 835
FEATURE                Location/Qualifiers
source                 1..835
                       mol_type = protein
                       organism = Homo sapiens
SEQUENCE: 10
MAELSEEALL SVLPTIRVPK AGDRVHKDEC AFSFDTPESE GGLYICMNTF LGFGKQYVER  60
HFNKTGQRVY LHLRRTRRPK EEDPATGTGD PPRKKPTRLA IGVEGGFDLS EEKFELDEDV  120
KIVILPDYLE IARDGLGGLP DIVRDRVTSA VEALLSADSA SRKQEVQAWD GEVRQVSKHA  180
FSLKQLDNPA RIPPCGWKCS KCDMRENLWL NLTDGSILCG RRYFDGSGGN NHAVEHYRET  240
GYPLAVKLGT ITPDGADVYS YDEDDMVLDP SLAEHLSHFG IDMLKMQKTD KTMTELEIDM  300
NQRIGEWELI QESGVPLKPL FGPGYTGIRN LGNSCYLNSV VQVLFSIPDF QRKYVDKLEK  360
IFQNAPTDPT QDFSTQVAKL GHGLLSGEYS KPVPESGDGE RVPEQKEVQD GIAPRMFKAL  420
IGKGHPEFST NRQQDAQEFF LHLINMVERN CRSSENPNEV FRFLVEEKIK CLATEKVKYT  480
QRVDYIMQLP VPMDAALNKE ELLEYEEKKR QAEEEKMALP ELVRAQVPFS SCLEAYGAPE  540
QVDDFWSTAL QAKSVAVKTT RFASFPDYLV IQIKKFTFGL DWVPKKLDVS IEMPEELDIS  600
```

-continued

```
QLRGTGLQPG EEELPDIAPP LVTPDEPKAP MLDESVIIQL VEMGFPMDAC RKAVYYTGNS  660
GAEAAMNWVM SHMDDPDFAN PLILPGSSGP GSTSAAADPP PEDCVTTIVS MGFSRDQALK  720
ALRATNNSLE RAVDWIFSHI DDLDAEAAMD ISEGRSAADS ISESVPVGPK VRDGPGKYQL  780
FAFISHMGTS TMCGHYVCHI KKEGRWVIYN DQKVCASEKP PKDLGYIYFY QRVAS       835

SEQ ID NO: 11           moltype = DNA  length = 4221
FEATURE                 Location/Qualifiers
misc_feature            1..4221
                        note = Other DNA
source                  1..4221
                        mol_type = other DNA
                        organism = Homo sapiens
SEQUENCE: 11
atggacatgg tagagaatgc agatagtttg caggcacagg agcggaagga catacttatg  60
aagtatgaca agggacaccg agctgggctg ccagaggaca aggggcctga gcccgttgga  120
atcaacagca gcattgatcg ttttggcatt ttgcatgaga cggagctgcc tcctgtgact  180
gcacgggagg cgaagaaaat tcggcgggag atgacacgaa cgagcaagtg gatggaaatg  240
ctgggagaat gggagacata taagcacagt agcaaactca tagatcgagt gtacaaggga  300
attcccatga acatccgggg cccggtgtgg tcagtcctcc tgaacattca ggaaatcaag  360
ttgaaaaacc ccggaagata ccagatcatg aaggagaggg gcaagaggtc atctgaacac  420
atccaccaca tcgacctgga cgtgaggacg actctccgga accatgtctt ctttagggat  480
cgatatggag ccaagcagag ggaactattc tacatcctcc tggcctattc ggagtataac  540
ccggaggtgg gctactgcag ggacctgagc cacatcaccg ccttgttcct cctttatctg  600
cctgaggagg acgcattctg ggcactggtg cagctgctgg ccagtgagag gcactccctg  660
ccaggattcc acagcccaaa tggtgggaca gtccaggggc tccaagacca acaggagcat  720
gtggtaccca agtcacaacc caagaccatg tggcatcagg acaaggaagg tctatgcggg  780
cagtgtgcct cgttaggctg ccttctccgg aacctgattg acgggatctc tctcgggctc  840
accctgcgcc tgtgggacgt gtatttggtg gaaggagaac aggtgttgat gccaataacc  900
agcattgctc ttaaggttca gcagaagcgc ctcatgaaga catccaggtg tggcctgtgg  960
gcacgtctgc ggaaccaatt cttcgatacc tgggccatga acgatgacac cgtgctcaag  1020
catcttaggg cctctacgaa gaaactaaca aggaagcaag gggacctgcc acccccagcc  1080
aaacgcgagc aagggtcctt ggcacccagg cctgtgccgg cttcacgtgg tgggaagacc  1140
ctctgcaagg ggtataggca ggcccctcca ggcccaccag cccagttcca gcggcccatt  1200
tgctcagctt ccccgccatg ggcatctcgt ttttccacgc cctgtcctgg tggggctgtc  1260
cgggaagaca cgtaccctgt gggcactcag ggtgtgccca gcctggccct ggctcaggga  1320
ggacctcagg gttcctggag attcctggag tggaagtcaa tgccccggct cccaacggac  1380
ctggatatag gggccccttg gttcccccat tatgattttg aatggagctg ctgggtccgt  1440
gccatatccc aggaggacca gctggccacc tgctggcagg ctgaacactg cggagaggtt  1500
cacaacaaag atatgagttg gcctgaggag atgtctttta cagcaaatag tagtaaaata  1560
gatagacaaa aggttcccac agaaaaggga gccacaggtc taagcaacct gggaaacaca  1620
tgcttcatga actcaagcat ccagtgcgtt agtaacacac agccactgac acagtatttt  1680
atctcaggga gacatcttta tgaactcaac aggacaaatc ccattggtat gaagggggcat  1740
atggctaaat gctatggtga tttagtgcag gaactctgga gtggaactca gaagagtgtt  1800
gccccattaa agcttcggcg gaccatagca aaatatgctc ccaagtttga tgggtttcag  1860
caacaagact cccaagaact tctggctttt ctcttggatg gtcttcatga agatctcaac  1920
cgagtccatg aaaagccata tgtggaactg aaggacagtg atggccgacc agactgggaa  1980
gtagctgcag aggcctggga caaccatcta agaagaaata gatcaattat tgtggatttg  2040
ttccatgggc agctaagatc tcaagtcaaa tgcaagacat gtgggcatat aagtgtccga  2100
tttgaccctt tcaatttttt gtctttgcca ctaccaatgg acagttacat ggacttagaa  2160
ataacagtga ttaagttaga tggtactacc cctgtacggt atggactaag actgaatatg  2220
gatgaaaagt acacaggttt aaaaaaacag ctgagggatc tctgtggact taattcagaa  2280
caaatcctac tagcagaagt acatgattcc aacataaaga actttcctca ggataaccaa  2340
aaagtacaac tctcagtgag cggatttttg tgtgcatttg aaattcctgt cccttcatct  2400
ccaatttcag cttctagtcc aacacaaata gatttctcct cttcaccatc tacaaatgga  2460
atgttcaccc taactaccaa tggggaccta cccaaaccaa tattcatccc caatggaatg  2520
ccaaacactg ttgtgccatg tggaactgag aagaacttca caaatggaat ggttaatggt  2580
cacatgccat ctcttcctga cagccccttt acaggttaca tcattgcagt ccaccgaaaa  2640
atgatgagga cagaactgta tttcctgtca cctcaggaga atcgccccag cctctttgga  2700
atgccattga ttgttccatg cactgtgcat acccggaaga aagacctata tgatgcggtt  2760
tggattcaag tatcctggtt agcaagacca ctcccacctc aggaagctag tattcatgcc  2820
caggatcgtg ataactgtat gggctatcaa tatccattca ctctacgagt tgtgcagaaa  2880
gatgggaact cctgtgcttg gtgcccacag tatagatttt gcagaggctg taaaattgat  2940
tgtggggaag acagagcttt cattggaaat gcctatattg ctgtggattg gcaccccaca  3000
gcccttcacc ttcgctatca aacatcccag gaaagggttg tagataagca tgagagtgtg  3060
gagcagagtc ggcgagcgca agccgagccc atcaacctgg acagctgtct ccgtgctttc  3120
accagtgagg aagagctagg ggaaagtgag atgtactact gttccaagtg taagacccac  3180
tgcttagcaa caaagaagct ggatctctgg aggcttccac ccttcctgat tattcacctt  3240
aagcgatttc aatttgtaaa tgatcagtgg ataaaatcac agaaaattgt cagatttctt  3300
cgggaaagtt ttgatccgag tgcttttttg gtaccacgag acccggccct ctgccagcat  3360
aaaccactca caccccaggg ggatgagctc tccaagccca ggattctggc aagagaggtg  3420
aagaaagtgg atgcgcagag ttcggctgga aaagaggaca tgctcctaag caaaagccca  3480
tcctcactca gcgctaacat cagcagcagc ccaaaaggtt ctccttcttc atcaagaaaa  3540
agtggaacca gctgtccctc cagcaaaaac agcagcccta atagcagccc acggactttg  3600
gggaggagca aagggaggct ccggctgccc cagattggca gcaaaaataa gccgtcaagt  3660
agtaagaaga acttggatgc cagcaaagag aatggggctg ggcagatctg tgagctggct  3720
gacgccttga gccgagggca tatgcggggg ggcagccaac cagagctggt cactcctcag  3780
gaccatgagg tagctttggc caatggattc ctttatgagc atgaagcatg tggcaatggc  3840
tgtggcgatg gctacagcaa tggtcagctt ggaaaccaca gtgaagaaga cagcactgat  3900
gaccaaagag aagacactca tattaagcct atttataatc tatatgcaat ttcatgccat  3960
```

-continued

```
tcaggaattc tgagtggggg ccattacatc acttatgcca aaaacccaaa ctgcaagtgg  4020
tactgttata atgacagcag ctgtgaggaa cttcaccctg atgaaattga caccgactct  4080
gcctacattc ttttctatga gcagcagggg atagactacg cacaatttct gccaaagatt  4140
gatggcaaaa agatggcaga cacaagcagt acggatgaag actctgagtc tgattacgaa  4200
aagtactcta tgttacagta a                                           4221

SEQ ID NO: 12          moltype = AA  length = 1406
FEATURE                Location/Qualifiers
source                 1..1406
                       mol_type = protein
                       organism = Homo sapiens
SEQUENCE: 12
MDMVENADSL QAQERKDILM KYDKGHRAGL PEDKGPEPVG INSSIDRFGI LHETELPPVT  60
AREAKKIRRE MTRTSKWMEM LGEWETYKHS SKLIDRVYKG IPMNIRGPVW SVLLNIQEIK  120
LKNPGRYQIM KERGKRSSEH IHHIDLDVRT TLRNHVFFRD RYGAKQRELF YILLAYSEYN  180
PEVGYCRDLS HITALFLLYL PEEDAFWALV QLLASERHSL PGFHSPNGGT VQGLQDQQEH  240
VVPKSQPKTM WHQDKEGLCG QCASLGCLLR NLIDGISLGL TLRLWDVYLV EGEQVLMPIT  300
SIALKVQQKR LMKTSRCGLW ARLRNQFFDT WAMNDDTVLK HLRASTKKLT RKQGDLPPPA  360
KREQGSLAPR PVPASRGGKT LCKGYRQAPP GPPAQFQRPI CSASPPWASR FSTPCPGGAV  420
REDTYPVGTQ GVPSLALAQG GPQGSWRFLE WKSMPRLPTD LDIGGPWFPH YDFEWSCWVR  480
AISQEDQLAT CWQAEHCGEV HNKDMSWPEE MSFTANSSKI DRQKVPTEKG ATGLSNLGNT  540
CFMNSSIQCV SNTQPLTQYF ISGRHLYELN RTNPIGMKGH MAKCYGDLVQ ELWSGTQKSV  600
APLKLRRTIA KYAPKFDGFQ QQDSQELLAF LLDGLHEDLN RVHEKPYVEL KDSDGRPDWE  660
VAAEAWDNHL RRNRSIIVDL FHGQLRSQVK CKTCGHISVR FDPFNFLSLP LPMDSYMDLE  720
ITVIKLDGTT PVRYGLRLNM DEKYTGLKKQ LRDLCGLNSE QILLAEVHDS NIKNFPQDNQ  780
KVQLSVSGFL CAFEIPVPSS PISASSPTQI DFSSSPSTNG MFTLTTNGDL PKPIFIPNGM  840
PNTVVPCGTE KNFTNGMVNG HMPSLPDSPF TGYIIAVHRK MMRTELYFLS PQENRPSLFG  900
MPLIVPCTVH TRKKDLYDAV WIQVSWLARP LPPQEASIHA QDRDNCMGYQ YPFTLRVVQK  960
DGNSCAWCPQ YRFCRGCKID CGEDRAFIGN AYIAVDWHPT ALHLRYQTSQ ERVVDKHESV  1020
EQSRRAQAEP INLDSCLRAF TSEEELGESE MYYCSKCKTH CLATKKLDLW RLPPFLIIHL  1080
KRFQFVNDQW IKSQKIVRFL RESFDPSAFL VPRDPALCQH KPLTPQGDEL SKPRILAREV  1140
KKVDAQSSAG KEDMLLSKSP SSLSANISSS PKGSPSSSRK SGTSCPSSKN SSPNSSPRTL  1200
GRSKGRLRLP QIGSKNKPSS SKKNLDASKE NGAGQICELA DALSRGHMRG GSQPELVTPQ  1260
DHEVALANGF LYEHEACGNG CGDGYSNGQL GNHSEEDSTD DQREDTHIKP IYNLYAISCH  1320
SGILSGGHYI TYAKNPNCKW YCYNDSSCEE LHPDEIDTDS AYILFYEQQG IDYAQFLPKI  1380
DGKKMADTSS TDEDSESDYE KYSMLQ                                      1406

SEQ ID NO: 13          moltype = DNA  length = 3309
FEATURE                Location/Qualifiers
misc_feature           1..3309
                       note = Other DNA
source                 1..3309
                       mol_type = other DNA
                       organism = Homo sapiens
SEQUENCE: 13
atgaaccacc agcagcagca gcagcagcag aaagcgggcg agcagcagtt gagcgagccc  60
gaggacatgg agatggaagc gggagataca gatgacccac caagaattac tcagaaccct  120
gtgatcaatg ggaatgtggc cctgagtgat ggacacaaca ccgcggagga ggacatggag  180
gatgacacca gttggcgctc cgaggcaacc tttcagttca ctgtggagcg cttcagcaga  240
ctgagtgagt cggtccttag ccctccgtgt tttgtgcgaa atctgccatg gaagattatg  300
gtgatgccac gcttttatcc agacagacca caccaaaaaa gcgtaggatt ctttctccag  360
tgcaatgctg aatctgattc cacgtcatgg tcttgccatg cacaagcagt gctgaagata  420
ataaattaca gagatgatga aaagtcgttc agtcgtcgta ttagtcattt gttcttccat  480
aaagaaaatg attggggatt ttccaatttt atggcctgga gtgaagtgac cgatcctgag  540
aaaggattta tagatgatga caaagttacc tttgaagtct ttgtacaggc ggatgctccc  600
catggagttg cgtgggattc aaagaagcac acaggctacg tcggcttaaa gaatcaggga  660
gcgacttgtt acatgaacag cctgctacag acgttatttt tcacgaatca gctacgaaag  720
gctgtgtaca tgatgccaac cgagggggat gattcgtcta aaagcgtccc tttagcatta  780
caaagagtgt tctatgaatt acagcatagt gataaacctg taggaacaaa aaagttaaca  840
aagtcatttg ggtgggaaac tttagatagc ttcatgcaac atgatgttca ggagctttgt  900
cgagtgttgc tcgataatgt ggaaaataag atgaaaggca cctgtgtaga gggcaccata  960
cccaaattat tccgcggcaa aatggtgtcc tatatccagt gtaaagaagt agactatcgg  1020
tctgatagaa gagaagatta ttatgatatc cagctaagta tcaaaggaaa gaaaaatata  1080
tttgaatcat ttgtggatta tgtggcagta gaacagctcg atggggacaa taaatacgac  1140
gctggggaac atggcttaca ggaagcagag aaaggtgtga aattcctaac attgccacca  1200
gtgttacatc tacaactgat gagatttatg tatgaccctc agacggacca aaatatcaag  1260
atcaatgata ggtttgaatt cccagagcag ttaccacttg atgaattttt gcaaaaaaca  1320
gatcctaagg accctgcaaa ttatattctt catgcagtcc tggttcatag tggagataat  1380
catggtggac attatgtggt ttatctaaac cccaaagggg atggcaaatg gtgtaaattt  1440
gatgacgacg tggtgtcaag gtgtactaaa gaggaagcaa ttgagcacaa ttatgggggt  1500
cacgatgacg acctgtctgt tcgacactgc actaatgctt acatgttagt ctacatcagg  1560
gaatcaaaac tgagtgaagt tttacaggcg gtcaccgacc atgatattcc tcagcagttg  1620
gtggagcgat tacaagaaga gaaaaggatc gaggctcaga agcggaagga gcggcaggaa  1680
gcccatctct atatgcaagt gcagatagtc gcagaggacc agttttgtgg ccaccaaggg  1740
aatgacatgt acgatgaaga aaaagtgaaa tacactgtgt tcaaagtatt gaagaactcc  1800
tcgcttgctg agtttgttca gagcctctct cagaccatgg gatttccaca agatcaaatt  1860
cgattgtggc ccatgcaagc aaggagtaat ggaacaaaac gaccagcaat gttagataat  1920
gaagccgacg gcaataaaac aatgattgag ctcagtgata atgaaaaccc ttggacaata  1980
ttcctggaaa cagttgatcc cgagctggct gctagtggag cgaccttacc caagtttgat  2040
```

-continued

```
aaagatcatg atgtaatgtt atttttgaag atgtatgatc ccaaaacgcg gagcttgaat  2100
tactgtgggc atatctacac accaatatcc tgtaaaatac gtgacttgct cccagttatg  2160
tgtgacagag caggatttat tcaagatact agccttatcc tctatgagga agttaaaccg  2220
aatttaacag agagaattca ggactatgac gtgtctcttg ataaagccct tgatgaacta  2280
atggatggtg acatcatagt atttcagaag gatgaccctg aaaatgataa cagtgaatta  2340
cccaccgcaa aggagtattt ccgagatctc taccaccgcg ttgatgtcat tttctgtgat  2400
aaaacaatcc ctaatgatcc tggatttgtg gttacgttat caaatagaat gaattatttt  2460
caggttgcaa agacagttgc acagaggctc aacacagatc caatgttgct gcagtttttc  2520
aagtctcaag gttataggga tggcccaggt aatcctctta gacataatta tgaaggtact  2580
ttaagagatc ttctacagtt cttcaagcct agacaaccta agaaacttta ctatcagcag  2640
cttaagatga aaatcacaga ctttgagaac aggcgaagtt ttaaatgtat atggttaaac  2700
agccaattta gggaagagga aataacacta tatccagaca agcatgggtg tgtccgggac  2760
ctgttagaag aatgtaaaaa ggccgtggag cttggggaga aagcatcagg gaaacttagg  2820
ctgctagaaa ttgtaagcta caaaatcatt ggtgttcatc aagaagatga actattagaa  2880
tgtttatctc ctgcaacgag ccggacgttt cgaatagagg aaatcccttt ggaccaggtg  2940
gacatagaca aagagaatga gatgcttgtc acagtggcgc atttccacaa agaggtcttc  3000
ggaacgttcg gaatcccgtt tttgctgagg atacaccagg gcgagcattt tcgagaagtg  3060
atgaagcgaa tccagagcct gctggacatc caggagaagg agtttgagaa gtttaaattt  3120
gcaattgtaa tgatgggccg acaccagtac ataaatgaag acgagtatga agtaaatttg  3180
aaagactttg agccacagcc cggtaatatg tctcatcctc ggccttggct agggctcgac  3240
cacttcaaca aagccccaaa gaggagtcgc tacacttacc ttgaaaaggc cattaaaatc  3300
cataactga                                                         3309
```

```
SEQ ID NO: 14          moltype = AA  length = 1102
FEATURE                Location/Qualifiers
source                 1..1102
                       mol_type = protein
                       organism = Homo sapiens
SEQUENCE: 14
MNHQQQQQQQ KAGEQQLSEP EDMEMEAGDT DDPPRITQNP VINGNVALSD GHNTAEEDME  60
DDTSWRSEAT FQFTVERFSR LSESVLSPPC FVRNLPWKIM VMPRFYPDRP HQKSVGFFLQ  120
CNAESDSTSW SCHAQAVLKI INYRDDEKSF SRRISHLFFH KENDWGFSNF MAWSEVTDPE  180
KGFIDDDKVT FEVFVQADAP HGVAWDSKKH TGYVGLKNQG ATCYMNSLLQ TLFFTNQLRK  240
AVYMMPTEGD DSSKSVPLAL QRVFYELQHS DKPVGTKKLT KSFGWETLDS FMQHDVQELC  300
RVLLDNVENK MKGTCVEGTI PKLFRGKMVS YIQCKEVDYR SDRREDYYDI QLSIKGKKNI  360
FESFVDYVAV EQLDGDNKYD AGEHGLQEAE KGVKFLTLPP VLHLQLMRFM YDPQTDQNIK  420
INDRFEFPEQ LPLDEFLQKT DPKDPANYIL HAVLVHSGDN HGGHYVVYLN PKGDGKWCKF  480
DDDVVSRCTK EEAIEHNYGG HDDDLSVRHC TNAYMLVYIR ESKLSEVLQA VTDHDIPQQL  540
VERLQEEKRI EAQKRKERQE AHLYMQVQIV AEDQFCGHQG NDMYDEEKVK YTVFKVLKNS  600
SLAEFVQSLS QTMGFPQDQI RLWPMQARSN GTKRPAMLDN EADGNKTMIE LSDNENPWTI  660
FLETVDPELA ASGATLPKFD KDHDVMLFLK MYDPKTRSLN YCGHIYTPIS CKIRDLLPVM  720
CDRAGFIQDT SLILYEEVKP NLTERIQDYD VSLDKALDEL MDGDIIVFQK DDPENDNSEL  780
PTAKEYFRDL YHRVDVIFCD KTIPNDPGFV VTLSNRMNYF QVAKTVAQRL NTDPMLLQFF  840
KSQGYRDGPG NPLRHNYEGT LRDLLQFFKP RQPKKLYYQQ LKMKITDFEN RRSFKCIWLN  900
SQFREEEITL YPDKHGCVRD LLEECKKAVE LGEKASGKLR LLEIVSYKII GVHQEDELLE  960
CLSPATSRTF RIEEIPLDQV DIDKENEMLV TVAHFHKEVF GTFGIPFLLR IHQGEHFREV  1020
MKRIQSLLDI QEKEFEKFKF AIVMMGRHQY INEDEYEVNL KDFEPQPGNM SHPRPWLGLD  1080
HFNKAPKRSR YTYLEKAIKI HN                                          1102
```

```
SEQ ID NO: 15          moltype = DNA  length = 3357
FEATURE                Location/Qualifiers
misc_feature           1..3357
                       note = Other DNA
source                 1..3357
                       mol_type = other DNA
                       organism = Homo sapiens
SEQUENCE: 15
atgcctgctg tggcttcagt tcctaaagaa ctctacctca gttcttcact aaaagacctt  60
aataagaaga cagaagttaa accagagaaa ataagcacta agagttatgt gcacagtgcc  120
ctgaagatct ttaagacagc agaagaatgc agattagatc gtgatgagga aagggcctat  180
gtactatata tgaaatacgt gactgtttat aatcttatca aaaaaagacc tgatttcaag  240
caacagcagg attatttcca ttcaatactt ggacctggaa acatcaaaaa agctgtcgaa  300
gaagctgaaa gactctctga aagccttaaa ttaagatatg aagaagctga agtccggaaa  360
aaacttgagg aaaaagacag gcaggaggaa gcacagcggc tacaacaaaa aaggcaggaa  420
acaggaagag aggatggtgg cacattggct aaaggctctt tggagaatgt tttggattcc  480
aaagacaaaa cccaaaagag caatggtgaa aagaatgaaa aatgtgagac caaagagaaa  540
ggagcaatca cagcaaagga actatacaca atgatgacgg ataaaaacat cagcttgatt  600
ataatggatg ctcgaagaat gcaggattat caggattcct gtattttaca ttctctcagt  660
gttcctgaag aagccatcag tccaggagtc actgctagtt ggattgaagc acacctgcca  720
gatgattcta aagacacatg gaagaagagg gggaatgtgg agtatgtggt acttcttgac  780
tggtttagtt ctgccaaaga tttacagatt ggaacaactc tccggagtct gaaagatgca  840
cttttcaagt gggaaagtaa aactgtcctg cgcaatgagc ctttggtttt agagggaggc  900
tatgaaaact ggctcctttg ttatccccag tatacaacaa atgctaaggt cactccaccc  960
ccacgacgcc agaatgaaga ggtgtctatc tcattggatt ttacttatcc ctcattggaa  1020
gaatcaattc cttctaaacc tgctgcccag acgccacctg catctataga agtagatgaa  1080
aatatagaat tgataagtgg tcaaaatgag agaatgggac cactgaatat atcaactcca  1140
gttgaaccag ttgctgcttc taaatctgat gtttcaccca taattcagcc agtgcctagt  1200
ataaagaatg ttccacagat tgatcgtact aaaaaaccag cagtcaaatt gcctgaagag  1260
catagaataa aatctgaaag tacaaaccat gagcaacaat ctcctcagag tggaaaagtt  1320
```

```
attcctgatc gttccaccaa gccagtagtt ttttctccaa ctctcatgtt aacagatgaa  1380
gaaaaggctc gtattcatgc agaaactgct cttctaatgg aaaaaaacaa acaagaaaaa  1440
gaacttcggg aaaggcagca agaggaacag aaagagaaac tgaggaagga agaacaagaa  1500
caaaaagcca aaaagaaaca agaagctgaa gaaaatgaaa ttacagagaa gcaacaaaaa  1560
gcaaaagaag aaatggagaa gaaagaaagt gaacaggcca agaaagaaga taaagaaacc  1620
tcagcaaaga ggggcaaaga aataacagga gtaaaaagac aaagtaaaag tgaacatgaa  1680
acttctgatg ccaagaaatc tgtagaagat agggggaaaa ggtgtccaac cccagaaata  1740
cagaaaaagt caacaggaga tgtgccccat acatctgtga caggggattc aggttcaggc  1800
aagccattta agattaaagg acaaccagaa agtggaattc taaggacagg aacttttaga  1860
gaggatacag acgataccga aagaaataaa gctcaacgag aacctttgac aagagcacga  1920
agtgaagaaa tggggaggat cgtaccagga ctgccttcag gctgggccaa gtttcttgac  1980
ccaatcactg gaacctttcg ttattatcat tcacccacca acactgttca tatgtaccca  2040
ccggaaatgg ctccttcatc tgcacctcct tccacccctc caactcataa agccaagcca  2100
cagattcctg ctgagcggga tagggaacct tccaaactga agcgctccta ctcctcccca  2160
gatataaccc aggctattca agaggaagag aagaggaagc caacagtaac tccaacagtt  2220
aatcgggaaa acaagccaac atgttatcct aaagctgaga tctcaaggct ttctgcttct  2280
cagattcgga acctcaatcc tgtttttgga ggttctggac cagctcttac tggacttcgt  2340
aacttaggaa atacttgtta tatgaactca atattgcagt gcctatgtaa cgctccacat  2400
ttggctgatt atttcaaccg aaactgttat caggatgata ttaacaggtc aaatttgttg  2460
gggcataaag gtgaagtggc agaagaattt ggtataatca tgaaagccct gtggacagga  2520
cagtatagat atatcagtcc aaaggacttt aaaatcacca ttgggaagat caatgaccag  2580
tttgcaggat acagtcagca agattcacaa gaattgcttc tgttcctaat ggatggtctc  2640
catgaagatc taaataaagc tgataatcgg aagagatata aagaagaaaa taatgatcat  2700
ctcgatgact ttaaagctgc agaacatgcc tggcagaaac acaagcagct caatgagtct  2760
attattgttg cactttttca gggtcaattc aaatctacag tacagtgcct cacatgtcac  2820
aaaaagtcta ggacatttga ggccttcatg tatttgtctc taccactagc atccacaagt  2880
aaatgtacat tacaggattg ccttagatta ttttccaaag aagaaaaact cacagataac  2940
aacagatttt actgcagtca ttgcagagct cgacgggatt ctctaaaaaa gatagaaatc  3000
tggaagttac cacctgtgct tttagtgcat ctgaaacgtt tttcctacga tggcaggtgg  3060
aaacaaaaat tacagacatc tgtggacttc ccgttagaaa atcttgactt gtcacagtat  3120
gttattggtc caaagaacaa tttgaagaaa tataatttgt ttctgtttc aaatcactac   3180
ggtgggctgg atggaggcca ctacacagcc tattgtaaaa atgcagcaag acaacggtgg  3240
tttaagtttg atgatcatga agtttctgat atctccgttt cttctgtgaa atcttcagca  3300
gcttatatcc tcttttatac ttcattggga ccacgagtaa ctgatgtagc cacataa     3357

SEQ ID NO: 16          moltype = AA  length = 1118
FEATURE                Location/Qualifiers
source                 1..1118
                       mol_type = protein
                       organism = Homo sapiens
SEQUENCE: 16
MPAVASVPKE LYLSSSLKDL NKKTEVKPEK ISTKSYVHSA LKIFKTAEEC RLDRDEERAY  60
VLYMKYVTVY NLIKKRPDFK QQQDYFHSIL GPGNIKKAVE EAERLSESLK LRYEEAEVRK  120
KLEEKDRQEE AQRLQQKRQE TGREDGGTLA KGSLENVLDS KDKTQKSNGE KNEKCETKEK  180
GAITAKELYT MMTDKNISLI IMDARRMQDY QDSCILHSLS VPEEAISPGV TASWIEAHLP  240
DDSKDTWKKR GNVEYVVLLD WFSSAKDLQI GTTLRSLKDA LFKWESKTVL RNEPLVLEGG  300
YENWLLCYPQ YTTNAKVTPP PRRQNEEVSI SLDFTYPSLE ESIPSKPAAQ TPPASIEVDE  360
NIELISGQNE RMGPLNISTP VEPVAASKSD VSPIIQPVPS IKNVPQIDRT KKPAVKLPEE  420
HRIKSESTNH EQQSPQSGKV IPDRSTKPVV FSPTLMLTDE EKARIHAETA LLMEKNKQEK  480
ELRERQQEEQ KEKLRKEEQE QKAKKKQEAE ENEITEKQQK AKEEMEKKES EQAKKEDKET  540
SAKRGKEITG VKRQSKSEHE TSDAKKSVED RGKRCPTPEI QKKSTGDVPH TSVTGDSGSG  600
KPFKIKGQPE SGILRTGTFR EDTDDTERNK AQREPLTRAR SEEMGRIVPG LPSGWAKFLD  660
PITGTFRYYH SPTNTVHMYP PEMAPSSAPP STPPTHKAKP QIPAERDREP SKLKRSYSSP  720
DITQAIQEEE KRKPTVTPTV NRENKPTCYP KAEISRLSAS QIRNLNPVFG GSGPALTGLR  780
NLGNTCYMNS ILQCLCNAPH LADYFNRNCY QDDINRSNLL GHKGEVAEEF GIIMKALWTG  840
QYRYISPKDF KITIGKINDQ FAGYSQQDSQ ELLLFLMDGL HEDLNKADNR KRYKEENNDH  900
LDDFKAAEHA WQKHKQLNES IIVALFQGQF KSTVQCLTCH KKSRTFEAFM YLSLPLASTS  960
KCTLQDCLRL FSKEEKLTDN NRFYCSHCRA RRDSLKKIEI WKLPPVLLVH LKRFSYDGRW  1020
KQKLQTSVDF PLENLDLSQY VIGPKNNLKK YNLFSVSNHY GGLDGGHYTA YCKNAARQRW  1080
FKFDDHEVSD ISVSSVKSSA AYILFYTSLG PRVTDVAT                          1118

SEQ ID NO: 17          moltype = DNA  length = 2397
FEATURE                Location/Qualifiers
misc_feature           1..2397
                       note = Other DNA
source                 1..2397
                       mol_type = other DNA
                       organism = Homo sapiens
SEQUENCE: 17
atggccctcc acagcccgca gtatattttt ggagatttta gccctgatga attcaatcaa  60
ttctttgtga ctcctcgatc ttcagttgag cttcctccat acagtggaac agttctgtgt  120
ggcacacagg ctgtggataa actacctgat ggacaagaat atcagagaat tgagtttggt  180
gtcgatgaag tcattgaacc cagtgacact ttgccgagaa cccccagcta cagtatttca  240
agcacactga accctcaggc ccctgaattt attctcggtt gtacagcttc caaaataacc  300
cctgatggta tcactaaaga agcaagctat ggctccatcg actgccagta cccaggctct  360
gccctcgctt tggatggaag ttctaatgtg gaggcggaag ttttggaaaa tgatggtgtc  420
tcaggtggtc ttggacaaag ggagcgtaaa aagaagaaaa agcggccacc tggatattac  480
agctatttga aagatggtgg cgatgatagt atctccacag aagccctggt caatggccat  540
gccaattcag cagtcccgaa cagtgtcagt gcagaggatg cagaatttat gggtgacatg  600
```

-continued cctccgccac ttacgcccag gacttgtaac agcccccaga actccacaga ctctgtcagt 660
gacattgtgc ctgacagtcc tttccccgga gcactcggca gtgacaccag gactgcaggg 720
cagccagagg ggggccccgg ggctgatttt ggtcagtcct gcttccctgc agaggctggc 780
agagacaccc tgtcaaggac agctggggct cagccctgcg ttggtaccga tactactgaa 840
aaccttggag ttgctaatgg acaaatactt gaatcctcgg gtgagggcac agctaccaac 900
ggggtggagt tgcacaccac ggaaagcata gacttggacc caaccaaacc cgagagtgca 960
tcacctcctg ctgacggcac gggctctgca tcaggcaccc ttcctgtcag ccagcccaag 1020
tcctgggcca gcctctttca tgattctaag ccctcttcct cctcgccggt ggcctatgtg 1080
gaaactaagt attcccctcc cgccatatct cccctggttt ctgaaaagca ggttgaagtc 1140
aaagaagggc ttgttccggt ttcagaggat cctgtagcca taaagattgc agagttgctg 1200
gagaatgtaa ccctaatcca taaaccagtg tcgttgcaac cccgtgggct gatcaataaa 1260
gggaactggt gctacattaa tgctacactg caggcattgg ttgcttgccc gccgatgtac 1320
cacctgatga agttcattcc tctgtattcc aaagtgcaaa ggccttgtac gtcaacaccc 1380
atgatagaca gctttgttcg gctaatgaat gagttcacta atatgccagt acctccaaaa 1440
ccccgacaag ctcttggaga taaaatcgtg agggatattc gccctggagc tgcctttgag 1500
cccacatata tttacagact cctgacagtt aacaagtcaa gcctgtctga aaagggtcga 1560
caagaagatg ctgaggaata cttaggcttc attctaaatg gacttcatga ggaaatgttg 1620
aacctaaaga agcttctctc accaagtaat gaaaaactta cgatttccaa cggcccccaaa 1680
aaccactcgg tcaatgaaga agagcaggaa gaacaaggtg aaggaagcga ggatgaatgg 1740
gaacaagtgg gcccccggaa caagacttcc gtcacccgcc aggcggattt tgttcagact 1800
ccaatcaccg gcatttttgg tggacacatc aggtctgtgg tttaccagca gagttcaaaa 1860
gaatctgcca ctttgcagcc atttttcacg ttgcagttgg atatccagtc agacaagata 1920
cgcacagtcc aggatgcact ggagagcttg gtggcaagag aatctgtcca aggttatacc 1980
acaaaaacca aacaagaggt tgagataagt cgaagagtga ctctggaaaa actccctcct 2040
gtcctcgtgc tgcacctgaa acgattcgtt tatgagaaga ctggtgggtg ccagaagctt 2100
atcaaaaata ttgaatatcc tgtggacttg gaaattagta aagaactgct ttctccaggg 2160
gttaaaaata agaattttaa atgccaccga acctatcggc tctttgcagt ggtctaccat 2220
cacggcaaca gtgcgacggg cggccattac actacagacg tcttccagat cggtctgaat 2280
ggctggctgc gcatcgatga ccagacagtc aaggtgatca accagtacca ggtggtgaaa 2340
ccaactgctg aacgcacagc ctacctcctg tattaccgcc gagtggacct gctgtaa 2397

SEQ ID NO: 18 moltype = AA length = 798
FEATURE Location/Qualifiers
source 1..798
mol_type = protein
organism = Homo sapiens
SEQUENCE: 18
MALHSPQYIF GDFSPDEFNQ FFVTPRSSVE LPPYSGTVLC GTQAVDKLPD GQEYQRIEFG 60
VDEVIEPSDT LPRTPSYSIS STLNPQAPEF ILGCTASKIT PDGITKEASY GSIDCQYPGS 120
ALALDGSSNV EAEVLENDGV SGGLGQRERK KKKRPPGYY SYLKDGGDDS ISTEALVNGH 180
ANSAVPNSVS AEDAEFMGDM PPPLTPRTCN SPQNSTDSVS DIVPDSPFPG ALGSDTRTAG 240
QPEGGPGADF GQSCFPAEAG RDTLSRTAGA QPCVGTDTTE NLGVANGQIL ESSGEGTATN 300
GVELHTTESI DLDPTKPESA SPPADGTGSA SGTLPVSQPK SWASLFHDSK PSSSSPVAYV 360
ETKYSPPAIS PLVSEKQVEV KEGLVPVSED PVAIKIAELL ENVTLIHKPV SLQPRGLINK 420
GNWCYINATL QALVACPPMY HLMKFIPLYS KVQRPCTSTP MIDSFVRLMN EFTNMPVPPK 480
PRQALGDKIV RDIRPGAAFE PTYIYRLLTV NKSSLSEKGR QEDAEEYLGF ILNGLHEEML 540
NLKKLLSPSN EKLTISNGPK NHSVNEEEQE EQGEGSEDEW EQVGPRNKTS VTRQADFVQT 600
PITGIFGGHI RSVVYQQSSK ESATLQPFFT LQLDIQSDKI RTVQDALESL VARESVQGYT 660
TKTKQEVEIS RRVTLEKLPP VLVLHLKRFV YEKTGGCQKL IKNIEYPVDL EISKELLSPG 720
VKNKNFKCHR TYRLFAVVYH HGNSATGGHY TTDVFQIGLN GWLRIDDQTV KVINQYQVVK 780
PTAERTAYLL YYRRVDLL 798

SEQ ID NO: 19 moltype = DNA length = 2763
FEATURE Location/Qualifiers
misc_feature 1..2763
note = Other DNA
source 1..2763
mol_type = other DNA
organism = Homo sapiens
SEQUENCE: 19
atggcgacgg tcgcagcaaa tccagctgct gctgcggcgg ctgtggcggc ggcagcggcg 60
gtgactgagg atagagagcc acagcacgag gagctgccag gcctggacag ccagtggcgc 120
cagatagaaa acggcgagag tgggcgagaa cgtccactgc gggccggcga aagctggttc 180
cttgtggaga agcactggta taagcagtgg gaggcatacg tgcagggagg ggaccaggac 240
tccagcacct tccctggctg catcaacaat gccacactct ttcaagatga gataaactgg 300
cgcctcaagg agggactggt ggaaggcgag gattatgtgc tgctcccagc agctgcttgg 360
cattacctgg tcagctggta tggtctagag catggccagc cacccattga acgcaaggtc 420
atagagctgc ccaacatcca gaaggtcgaa gtgtacccag tagaactgct gcttgtccgg 480
cacaatgatt tgggcaaatc tcacactgtt cagttcagcc ataccgattc tattggccta 540
gtattgcgca cagctcggga gcggtttctg gtggagcccc aggaagacac tcggctttgg 600
gccaagaact cagaaggctc tttggatagg ttgtatgaca cacacatcac ggttctcgat 660
gcggcccttg agactgggca gttgatcatc atggagaccc gcaagaaaga tggcacttgg 720
cccagcgcac agctgcatgt catgaacaac aacatgtcgg aagaggatga ggacttcaag 780
ggtcagccag gcatctgtgg cctcaccaat ctgggcaaca cgtgcttcat gaactcggcc 840
ctgcagtgcc tcagcaatgt gccacagctc accgagtact tcctcaacaa ctgctacctg 900
gaggagctca acttccgcaa cccactgggc atgaagggtg agatcgcaga ggcctatgca 960
gacctggtga agcaggcgtg gtctggccac caccgctcca ttgtgccaca tgtgttcaag 1020
aacaaggttg gccattttgc atcccaattt ctgggctacc agcagcatga ctctcaggag 1080
ctgctgtcat tcctcctgga cgggctgcat gaggacctta atcgggtgaa gaagaaggag 1140

```
tatgtggagc tgtgcgatgc tgctgggcga ccggatcagg aggtggcaca ggaggcatgg  1200
caaaaccaca aacggcggaa cgattctgtg atcgtggaca ctttccacgg cctcttcaag  1260
tccacgctgg tgtgccccga ttgtggcaat gtatctgtga ccttcgaccc cttctgctac  1320
ctcagtgttc cactgcctat cagccacaag agggtcttgg aggtcttctt tatccccatg  1380
gatccgcgcc gcaagccaga gcagcaccgg ctcgtggtcc ccaagaaagg caagatctcg  1440
gatctatgtg tggctctgtc caaacacacg ggcatctcgc cagagaggat gatggtggct  1500
gatgtcttca gtcaccgctt ctataagctc tatcagctag aggagcctct gagcagcatc  1560
ttggaccgtg atgatatctt cgtctatgag gtgtcaggtc gcattgaggc cattgagggc  1620
tcaagagagg acatcgtggt tcctgtctac ctgcgggagc gcacccctgc ccgtgactac  1680
aacaactcct actacggcct gatgcttttt ggacaccccc tcctggtatc agtgccccgg  1740
gaccgcttca cctgggaggg cctgtataac gtcctgatgt accggctctc acgctacgtg  1800
accaaaccca actcagatga tgaggacgat ggggatgaga aagaagatga cgaggaggat  1860
aaagatgacg tccctgggcc ctcaactggg ggcagcctcc gagaccctga gccagagcag  1920
gctgggccca gctctggagt cacgaacagg tgcccgttcc tcctggacaa ttgccttggc  1980
acatctcagt ggcccccaag gcgacgacgc aagcagctgt tcaccctgca gacggtgaac  2040
tccaatggga ccagcgaccg cacaacctcc cctgaagaag tccatgccca gccgtacatt  2100
gctatcgact gggagccaga gatgaagaag cgttactatg acgaggtaga ggctgagggc  2160
tacgtgaagc atgactgcgt cgggtacgtg atgaagaagg ctcccgtgcg gctgcaggag  2220
tgcattgagc tcttcaccac tgtggagacc ctggagaagg aaaacccctg gtactgccct  2280
tcctgcaagc agcaccagct ggcaaccaag aagctggacc tgtggatgct gccggagatt  2340
ctcatcatcc acctgaaacg cttttcctac accaagttct cccgagagaa gctggacacc  2400
ctcgtggagt ttcctatccg ggacctggac ttctctgagt ttgtcatcca gccacagaat  2460
gagtcgaatc cggagctgta caaatatgac ctcatcgcgg tttccaacca ttatgggggc  2520
atgcgtgatg gacactacac aacatttgcc tgcaacaagg acagcggcca gtggcactac  2580
tttgatgaca acagcgtctc ccctgtcaat gagaatcaga tcgagtccaa ggcagcctat  2640
gtcctcttct accaacgcca ggacgtggcg cgacgcctgc tgtccccggc cggctcatct  2700
ggcgccccag cctcccctgc ctgcagctcc ccacccagct ctgagttcat ggatgttaat  2760
tga                                                                2763
```

```
SEQ ID NO: 20          moltype = AA  length = 920
FEATURE                Location/Qualifiers
source                 1..920
                       mol_type = protein
                       organism = Homo sapiens
SEQUENCE: 20
MATVAANPAA AAAAVAAAAA VTEDREPQHE ELPGLDSQWR QIENGESGRE RPLRAGESWF  60
LVEKHWYKQW EAYVQGGDQD SSTFPGCINN ATLFQDEINW RLKEGLVEGE DYVLLPAAAW  120
HYLVSWYGLE HGQPPIERKV IELPNIQKVE VYPVELLLVR HNDLGKSHTV QFSHTDSIGL  180
VLRTARERFL VEPQEDTRLW AKNSEGSLDR LYDTHITVLD AALETGQLII METRKKDGTW  240
PSAQLHVMNN NMSEEDEDFK GQPGICGLTN LGNTCFMNSA LQCLSNVPQL TEYFLNNCYL  300
EELNFRNPLG MKGEIAEAYA DLVKQAWSGH HRSIVPHVFK NKVGHFASQF LGYQQHDSQE  360
LLSFLLDGLH EDLNRVKKKE YVELCDAAGR PDQEVAQEAW QNHKRRNDSV IVDTFHGLFK  420
STLVCPDCGN VSVTFDPFCY LSVPLPISHK RVLEVFFIPM DPRRKPEQHR LVVPKKGKIS  480
DLCVALSKHT GISPERMMVA DVFSHRFYKL YQLEEPLSSI LDRDDIFVYE VSGRIEAIEG  540
SREDIVVPVY LRERTPARDY NNSYYGLMLF GHPLLVSVPR DRFTWEGLYN VLMYRLSRYV  600
TKPNSDDEDD GDEKEDDEED KDDVPGPSTG GSLRDPEPEQ AGPSSGVTNR CPFLLDNCLG  660
TSQWPPRRRR KQLFTLQTVN SNGTSDRTTS PEEVHAQPYI AIDWEPEMKK RYYDEVEAEG  720
YVKHDCVGYV MKKAPVRLQE CIELFTTVET LEKENPWYCP SCKQHQLATK KLDLWMLPEI  780
LIIHLKRFSY TKFSREKLDT LVEFPIRDLD FSEFVIQPQN ESNPELYKYD LIAVSNHYGG  840
MRDGHYTTFA CNKDSGQWHY FDDNSVSPVN ENQIESKAAY VLFYQRQDVA RRLLSPAGSS  900
GAPASPACSS PPSSEFMDVN                                              920
```

```
SEQ ID NO: 21          moltype = DNA  length = 1113
FEATURE                Location/Qualifiers
misc_feature           1..1113
                       note = Other DNA
source                 1..1113
                       mol_type = other DNA
                       organism = Homo sapiens
SEQUENCE: 21
atggaaatcc taatgacagt ctccaaattc gcctccatct gtaccatggg cgccaatgct  60
tcggcattag agaaagagat tggtccagaa cagtttccgg tcaatgagca ctattttgga  120
ttagtcaatt ttgggaatac ctgctactgc aattcagttc ttcaagcact ttatttttgt  180
cgtccatttc gggaaaaagt tcttgcgtat aagagtcaac ctaggaaaaa ggagagcctt  240
cttacatgct tagcagatct cttccatagc atagccactc agaagaaaaa ggttggagta  300
atacccccta agaagttcat cacaagatta cggaaagaaa atgagctttt tgacaactac  360
atgcaacaag atgcccatga attcttaaat tacctactaa atacaattgc tgatatttta  420
caagaagaga gaaagcagga aaaacaaaat ggtcgtttac ctaatggtaa tattgataat  480
gaaaataata acagcacacc agacccaacg tgggttcatg agatttttca gggaacatta  540
actaatgaaa ccagatgtct tacttgtgaa actataagca gcaaagatga agattttta  600
gacctttctg ttgacgtgga acaaaataca tcaattactc actgcttaag ggggtttcagc  660
aacacagaaa ctctgtgcag tgaatacaag tattactgtg aagagtgtcg cagcaaacag  720
gaagcacaca aacggatgaa agttaaaaaa ctgcccatga ttctagctct acacctgaag  780
agatttaaat atatggatca acttcatcga tatacaaaac tctcttaccg ggtagttttt  840
cctttagaac ttcgtctgtt taacacttca ggtgatgcca ccaatccaga cagaatgtac  900
gaccttgttg ctgttgtggt tcactgtgga agtggtccca atcgaggcca ttatattgca  960
atagttaaga gtcatgattt ttggttgttg tttgatgacg acattgtaga aaaaatagat  1020
gcacaagcta ttgaagaatt ctacgggttg acatcagata tctcaaagaa ctctgagtct  1080
ggttacatcc ttttctatca gtctcgggac tga                               1113
```

```
SEQ ID NO: 22          moltype = AA  length = 370
FEATURE                Location/Qualifiers
source                 1..370
                       mol_type = protein
                       organism = Homo sapiens
SEQUENCE: 22
MEILMTVSKF ASICTMGANA SALEKEIGPE QFPVNEHYFG LVNFGNTCYC NSVLQALYFC  60
RPFREKVLAY KSQPRKKESL LTCLADLFHS IATQKKKVGV IPPKKFITRL RKENELFDNY  120
MQQDAHEFLN YLLNTIADIL QEERKQEKQN GRLPNGNIDN ENNNSTPDPT WVHEIFQGTL  180
TNETRCLTCE TISSKDEDFL DLSVDVEQNT SITHCLRGFS NTETLCSEYK YYCEECRSKQ  240
EAHKRMKVKK LPMILALHLK RFKYMDQLHR YTKLSYRVVF PLELRLFNTS GDATNPDRMY  300
DLVAVVVHCG SGPNRGHYIA IVKSHDFWLL FDDDIVEKID AQAIEEFYGL TSDISKNSES  360
GYILFYQSRD                                                      370

SEQ ID NO: 23          moltype = DNA  length = 1485
FEATURE                Location/Qualifiers
misc_feature           1..1485
                       note = Other DNA
source                 1..1485
                       mol_type = other DNA
                       organism = Homo sapiens
SEQUENCE: 23
atgccgctct actccgttac tgtaaaatgg ggaaaggaga aatttgaagg tgtagaattg  60
aatacagatg aacctccaat ggtattcaag gctcagctgt ttgcgttgac tggagtccag  120
cctgccagac agaaagttat ggtgaaagga ggaacgctaa aggatgatga ttggggaaac  180
atcaaaataa aaaatggaat gactctacta atgatggggt cagcagatgc tcttccagaa  240
gaaccctcag ccaaaactgt cttcgtagaa gacatgacag aagaacagtt agcatctgct  300
atggagttac catgtggatt gacaaacctt ggtaacactt gttacatgaa tgccacagtt  360
cagtgtattc gttctgtgcc tgaactcaaa gatgccctta aaaggtatgc aggtgccttg  420
agagcttcag gggaaatggc ttcagcgcag tatattactg cagcccttag agatttgttt  480
gattccatgg ataaaacttc ttccagtatt ccacctatta ttctactgca gtttttgcac  540
atggctttcc cacagtttgc cgagaaaggt gaacaaggac agtatcttca acaggatgct  600
aatgaatgtt ggatacaaat gatgcgagta ttgcaacaga aattggaagc aatagaggat  660
gattctgtta aagagacaga ctcctcatct gcatcggcag cgacaccttc taaaaagaaa  720
agtttaatcg atcagttctt cggtgttgag tttgaaacta ccatgaaatg tacagaatct  780
gaagaagaag aagtcaccaa aggaaaggaa aatcaacttc agcttagctg ttttatcaat  840
caggaagtca agtatctttt tacaggactt aaattgcgac ttcaggaaga aatcaccaaa  900
cagtctccaa cgttgcaaag aaatgccttg tatatcaaat cttccaagat cagccggctg  960
cctgcttact tgaccattca gatggttcga ttttttata aagagaagga atctgtgaat  1020
gccaaagttc ttaaggatgt taaatttcct cttatgttgg atatgtatga actgtgtaca  1080
ccagaacttc aagagaaaat ggtgtctttt cgatccaaat tcaaggatct agaagataaa  1140
aaagtgaatc agcagccaaa tacaagtgac aaaaagagta gtccccagaa agaagttaag  1200
tatgaaccct tttcttttgc tgatgatatt ggctccaata attgtggata ctatgactta  1260
caagcagtac taacacacca gggaaggtct agttcttcag gtcattatgt atcatgggtg  1320
aaaaggaaac aagatgaatg gattaagttt gatgatgaca aagtcagcat cgtaacacca  1380
gaagatatct tacggctttc tggtggtgga gactggcata tcgcttacgt tctactctat  1440
gggcctcgca gagttgaaat aatggaagag gaaagtgaac agtaa                1485

SEQ ID NO: 24          moltype = AA  length = 494
FEATURE                Location/Qualifiers
source                 1..494
                       mol_type = protein
                       organism = Homo sapiens
SEQUENCE: 24
MPLYSVTVKW GKEKFEGVEL NTDEPPMVFK AQLFALTGVQ PARQKVMVKG GTLKDDDWGN  60
IKIKNGMTLL MMGSADALPE EPSAKTVFVE DMTEEQLASA MELPCGLTNL GNTCYMNATV  120
QCIRSVPELK DALKRYAGAL RASGEMASAQ YITAALRDLF DSMDKTSSSI PPIILLQFLH  180
MAFPQFAEKG EQGQYLQQDA NECWIQMMRV LQQKLEAIED DSVKETDSSS ASAATPSKKK  240
SLIDQFFGVE FETTMKCTES EEEEVTKGKE NQLQLSCFIN QEVKYLFTGL KLRLQEEITK  300
QSPTLQRNAL YIKSSKISRL PAYLTIQMVR FFYKEKESVN AKVLKDVKFP LMLDMYELCT  360
PELQEKMVSF RSKFKDLEDK KVNQQPNTSD KKSSPQKEVK YEPFSFADDI GSNNCGYYDL  420
QAVLTHQGRS SSSGHYVSWV KRKQDEWIKF DDDKVSIVTP EDILRLSGGG DWHIAYVLLY  480
GPRRVEIMEE ESEQ                                                 494

SEQ ID NO: 25          moltype = DNA  length = 2859
FEATURE                Location/Qualifiers
misc_feature           1..2859
                       note = Other DNA
source                 1..2859
                       mol_type = other DNA
                       organism = Homo sapiens
SEQUENCE: 25
atggcggaag gcggagcggc ggatctggac acccagcggt ctgacatcgc gacgctgctc  60
aaaacctcgc tccggaaagg ggacacctgg tacctagtcg atagtcgctg gttcaaacag  120
tggaaaaaat atgttggctt tgacagttgg gacaaatacc agatgggaga tcaaaatgtg  180
tatcctggac ccattgataa ctctggactt ctcaaagatg gtgatgccca gtcacttaag  240
gaacacctta ttgatgaatt ggattacata ctgttgccaa ctgaaggttg gaataaactt  300
gtcagctggt acacattgat ggaaggtcaa gagccaatag cacgaaaggt ggttgaacag  360
```

```
ggtatgtttg taaagcactg caaagtagaa gtatatctca cagaattgaa gctatgtgaa  420
aatggaaaca tgaataatgt tgtaactcga agatttagca aagctgacac aatagataca  480
attgaaaagg aaataagaaa aatcttcagt attccagatg aaaaggagac cagattgtgg  540
aacaaataca tgagtaacac atttgaacca ctgaataaac cagacagcac cattcaggat  600
gctggtttat accaaggaca ggtattagtg atagaacaga aaaatgaaga tggaacatgg  660
ccaaggggtc cttctactcc taatgtgaaa aactcaaatt actgtcttcc atcatatacc  720
gcttataaga actatgatta ttcggaacct ggaagaaaca atgaacagcc aggcctctgt  780
ggcctaagta acttgggaaa tacgtgtttc atgaactcag ctattcagtg tttgagcaac  840
acacctccac ttactgagta tttcctcaat gataagtatc aagaagaact gaattttgac  900
aatcccttag gaatgagagg tgaaatagct aaatcttatg ccgaactgat caagcaaatg  960
tggtctggaa agtttagcta cgtcacccca agagccttta agacacaggt aggacgtttt  1020
gcacctcagt tctctggata tcagcagcaa gactgtcaag aactgttagc tttcctatta  1080
gatggattac atgaggattt gaatagaatt aggaaaaaac catatataca attaaaagat  1140
gcagatggaa ggccagataa ggtggttgcc gaagaagcct gggaaaacca tttaaaacga  1200
aatgattcta tcatagtaga tatatttcat ggccttttca aatcaacttt agtttgtcct  1260
gagtgtgcta agatttcagt aacatttgat cctttttgtt acttgacact tccattgccc  1320
atgaaaaaag aacgcacctt ggaagtttac ttagttagaa tggatccact taccaaacct  1380
atgcagtaca aagtggttgt ccccaaaatt ggaaacatat tagatctttg tacagcattg  1440
tctgctttgt caggaatacc tgcagataag atgatagtta ctgatatata caatcataga  1500
tttcacagaa tattcgctat ggatgaaaac cttagtagta ttatggaacg ggatgatatt  1560
tatgtgtttg aaattaacat caataggaca gaagatacag agcacgtgat tattcctgtt  1620
tgcctaagag aaaaattcag acactcgagt tatacccacc atactggttc ttcacttttt  1680
ggtcagccct ttcttatggc tgtaccacga aacaatactg aagacaaact ttataatctc  1740
ctgctcttga gaatgtgccg atatgtcaaa atatctactg aaactgaaga aactgaagga  1800
tccctacact gctgtaagga ccaaaatatt aatgggaatg gcccaaatgg catacatgaa  1860
gaaggctcac caagtgaaat ggaaacagat gagccagatg atgaatccag ccaggatcaa  1920
gaacttccct cagagaatga aaacagtcag tctgaagatt cagttggagg agataatgat  1980
tctgaaaatg gattatgtac tgaggatact tgcaaaggtc aactcacggg acacaaaaaa  2040
cgattgttta cattccagtt caacaactta ggcaatactg atatcaacta catcaaagat  2100
gataccaggc atataagatt tgatgatagg cagcttaggc tagatgaaag atttttttctt  2160
gctttggatt gggatcctga tttgaaaaaa agatattttg atgaaaatgc tgccgaggac  2220
tttgaaaaac atgaaagtgt ggagtataaa cctcctaaaa aaccctttgt gaaattaaaa  2280
gattgcattg aacttttac aacaaaagaa aagctaggtg ctgaagatcc ctggtattgt  2340
ccgaattgta aagaacatca gcaagccaca aagaaattgg atttatggtc cctgcctcca  2400
gtacttgtag tacatctcaa gcgattttct tacagtcgat acatgagaga caagttggat  2460
accttagttg attttcctat caatgacttg gatatgtcgg aattcttaat taatccaaat  2520
gcaggtcctt gccgctataa tctgattgct gtttccaacc actatggagg gatgggagga  2580
ggacactata ctgcttttgc aaaaaataaa gatgatggaa aatggtacta ttttgatgac  2640
agtagtgtct ccactgcatc tgaagaccaa attgtgtcca aagcagcata tgtactcttc  2700
taccagagac aagacacttt cagtggaact ggcttttttc ctcttgaccg agaaactaaa  2760
ggtgcttcag ctgccactgg catcccatta gaaagtgatg aagatagcaa tgataatgac  2820
aatgatatag aaaatgaaaa ctgtatgcac actaactaa                        2859

SEQ ID NO: 26           moltype = AA  length = 952
FEATURE                 Location/Qualifiers
source                  1..952
                        mol_type = protein
                        organism = Homo sapiens
SEQUENCE: 26
MAEGGAADLD TQRSDIATLL KTSLRKGDTW YLVDSRWFKQ WKKYVGFDSW DKYQMGDQNV  60
YPGPIDNSGL LKDGDAQSLK EHLIDELDYI LLPTEGWNKL VSWYTLMEGQ EPIARKVVEQ  120
GMFVKHCKVE VYLTELKLCE NGNMNNVVTR RFSKADTIDT IEKEIRKIFS IPDEKETRLW  180
NKYMSNTFEP LNKPDSTIQD AGLYQGQVLV IEQKNEDGTW PRGPSTPNVK NSNYCLPSYT  240
AYKNYDYSEP GRNNEQPGLC GLSNLGNTCF MNSAIQCLSN TPPLTEYFLN DKYQEELNFD  300
NPLGMRGEIA KSYAELIKQM WSGKFSYVTP RAFKTQVGRF APQFSGYQQQ DCQELLAFLL  360
DGLHEDLNRI RKKPYIQLKD ADGRPDKVVA EEAWENHLKR NDSIIVDIFH GLFKSTLVCP  420
ECAKISVTFD PFCYLTLPLP MKKERTLEVY LVRMDPLTKP MQYKVVVPKI GNILDLCTAL  480
SALSGIPADK MIVTDIYNHR FHRIFAMDEN LSSIMERDDI YVFEININRT EDTEHVIIPV  540
CLREKFRHSS YTHHTGSSLF GQPFLMAVPR NNTEDKLYNL LLLRMCRYVK ISTETEETEG  600
SLHCCKDQNI NGNGPNGIHE EGSPSEMETD EPDDESSQDQ ELPSENENSQ SEDSVGGDND  660
SENGLCTEDT CKGQLTGHKK RLFTFQFNNL GNTDINYIKD DTRHIRFDDR QLRLDERFFL  720
ALDWDPDLKK RYFDENAAED FEKHESVEYK PPKKPFVKLK DCIELFTTKE KLGAEDPWYC  780
PNCKEHQQAT KKLDLWSLPP VLVVHLKRFS YSRYMRDKLD TLVDFPINDL DMSEFLINPN  840
AGPCRYNLIA VSNHYGGMGG GHYTAFAKNK DDGKWYYFDD SSVSTASEDQ IVSKAAYVLF  900
YQRQDTFSGT GFFPLDRETK GASAATGIPL ESDEDSNDND NDIENENCMH TN          952

SEQ ID NO: 27           moltype = DNA  length = 1227
FEATURE                 Location/Qualifiers
misc_feature            1..1227
                        note = Other DNA
source                  1..1227
                        mol_type = other DNA
                        organism = Homo sapiens
SEQUENCE: 27
atgggaaaga aacggacaaa gggaaaaact gttccaatcg atgattcctc tgaaacttta  60
gaacctgtgt gcagacacat tagaaaagga ttggaacaag gtaatttgaa aaaggcttta  120
gtgaatgtgg aatggaatat ctgccaagac tgtaagactg acaataaagt gaaagataaa  180
gctgaagaag aaacagaaga aaagccttca gtttggctgt gtcttaaatg tggccatcag  240
ggctgtggca gaaattctca ggagcagcat gccttgaagc actatctgac gccaagatct  300
```

```
gaacctcact gtctggttct tagtttggac aactggagtg tatggtgtta cgtatgtgat  360
aatgaggtcc agtattgtag ttcaaaccag ttgggtcaag tggttgatta tgtcagaaaa  420
caagccagca ttacaactcc aaagccagca gagaaagata atggaaatat tgaacttgaa  480
aataaaaaat tagaaaaaga gagtaagaat gaacaagaga gagaaaagaa ggaaaacatg  540
gctaaagaga atcctcccat gaattctcct tgccaaataa ccgtgaaagg actcagtaat  600
ttgggaaaca catgtttctt caatgcagtt atgcagaact tgtcacaaac accagtgctt  660
agagaactac taaaagaagt gaaaatgtct ggaacaattg taaaaattga accacctgat  720
ttggcattaa cagaaccatt agaaataaac cttgagcctc caggccctct tactttagcc  780
atgagccagt ttcttaatga gatgcaagag accaaaaagg gggttgtgac accgaaagaa  840
ctcttttctc aggtctgtaa aaaagcagtg cggtttaaag gctatcagca gcaagacagc  900
caggagctgc ttcgctactt attggatggg atgagagcag aagaacacca aagagtgagt  960
aaaggaatac ttaaagcatt tggtaattct actgaaaagt tggatgaaga actaaaaaat  1020
aaagttaaag attatgagaa gaaaaaatca atgccaagtt ttgttgaccg catctttggt  1080
ggtgaactaa ctagtatgat catgtgtgat caatgcagaa ctgtctcctt ggttcatgaa  1140
tctttccttg atttgtccct cccagtttta gatgatcagg taagactatt gaatttattt  1200
tattcaagta gattttttt cctgtaa                                       1227

SEQ ID NO: 28          moltype = AA  length = 408
FEATURE                Location/Qualifiers
source                 1..408
                       mol_type = protein
                       organism = Homo sapiens
SEQUENCE: 28
MGKKRTKGKT VPIDDSSETL EPVCRHIRKG LEQGNLKKAL VNVEWNICQD CKTDNKVKDK  60
AEEETEEKPS VWLCLKCGHQ GCGRNSQEQH ALKHYLTPRS EPHCLVLSLD NWSVWCYVCD  120
NEVQYCSSNQ LGQVVDYVRK QASITTPKPA EKDNGNIELE NKKLEKESKN EQEREKKENM  180
AKENPPMNSP CQITVKGLSN LGNTCFFNAV MQNLSQTPVL RELLKEVKMS GTIVKIEPPD  240
LALTEPLEIN LEPPGPLTLA MSQFLNEMQE TKKGVVTPKE LFSQVCKKAV RFKGYQQQDS  300
QELLRYLLDG MRAEEHQRVS KGILKAFGNS TEKLDEELKN KVKDYEKKKS MPSFVDRIFG  360
GELTSMIMCD QCRTVSLVHE SFLDLSLPVL DDQVRLLNLF YSSRFFFL               408

SEQ ID NO: 29          moltype = DNA  length = 1593
FEATURE                Location/Qualifiers
misc_feature           1..1593
                       note = Other DNA
source                 1..1593
                       mol_type = other DNA
                       organism = Homo sapiens
SEQUENCE: 29
atggaggacg actcactcta cttgggaggt gagtggcagt tcaaccactt ttcaaaactc  60
acatcttctc ggccagatgc agcttttgct gaaatccagc ggacttctct ccctgagaag  120
tcaccactct catctgaggc ccgtgtcgac ctctgtgatg atttggctcc tgtggcaaga  180
cagcttgctc ccagggagaa gcttcctctg agtagcagga gacctgctgc ggtgggggct  240
gggctccaga atatgggaaa tacctgctac gagaacgctt ccctgcagtg cctgacatac  300
acaccgcccc ttgccaacta catgctgtcc cgggagcact ctcaaacatg tcagcgtccc  360
aagtgctgca tgctctgtac tatgcaagct cacatcacat gggccctcca cagtcctggt  420
catgtcatcc agccctcaca ggcattggct gctggcttcc atagaggcaa gcaggaagat  480
gcccatgaat ttctcatgtt cactgtggat gccatgaaaa aggcatgcct tcccggccac  540
aagcaggtag atcatcactc taaggacacc accctcatcc accaaatatt tggaggctgc  600
tggagatctc aaatcaagtg tctccactgc cacgggattc cagacacttt tgacccttac  660
ctggacatcg ccctggatat ccaggcagct cagagtgtca agcaagcttt ggaacagttg  720
gtgaagcccg aagaactcaa tggagagaat gcctatcatt gtggtctttg tctccagagg  780
gcgccggcct ccaagacgtt aactttacac acttctgcca aggtcctcat ccttgtmttg  840
aagagattct ccgatgtcac aggcaacaaa cttgccaaga atgtgcaata tcctgagtgc  900
cttgacatgc agccatacat gtctcagcag aacacaggac ctcttgtcta tgtcctctat  960
gctgtgctgg tccacgctgg gtggagttgt cacaacggac attacttctc ttatgtcaaa  1020
gctcaagaag gccagtggta taaaatggat gatgccgagg tcaccgcctc tagcatcact  1080
tctgtcctga gtcaacaggc ctacgtcctc ttttacatcc agaagagtga atgggaaaga  1140
cacagtgaga gtgtgtcaag aggcagggaa ccaagagccc ttggcgcaga agacacagac  1200
aggcgagcaa cgcaaggaga gctcaagaga gaccacccct gcctccaggc ccccgagttg  1260
gacgagcact tggtggaaag agccactcag gaaagcacct tagaccactg gaaattcctt  1320
caagagcaaa acaaaacgaa gcctgagttc aacgtcagaa aagtcgaagg taccctgcct  1380
cccgacgtac ttgtgattca tcaatcaaaa tacaagtgtg ggatgaagaa ccatcatcct  1440
gaacagcaaa gctccctgct aaacctctct tcgacgaccc cgacacatca ggagtccatg  1500
aacactggca cactcgcttc cctgcgaggg agggccagga gatccaaagg gaagaacaaa  1560
cacagcaaga gggctctgct tgtgtgccag tga                               1593

SEQ ID NO: 30          moltype = AA  length = 530
FEATURE                Location/Qualifiers
source                 1..530
                       mol_type = protein
                       organism = Homo sapiens
SEQUENCE: 30
MEDDSLYLGG EWQFNHFSKL TSSRPDAAFA EIQRTSLPEK SPLSSEARVD LCDDLAPVAR  60
QLAPREKLPL SSRRPAAVGA GLQNMGNTCY ENASLQCLTY TPPLANYMLS REHSQTCQRP  120
KCCMLCTMQA HITWALHSPG HVIQPSQALA AGFHRGKQED AHEFLMFTVD AMKKACLPGH  180
KQVDHHSKDT TLIHQIFGGC WRSQIKCLHC HGIPDTFDPY LDIALDIQAA QSVKQALEQL  240
VKPEELNGEN AYHCGLCLQR APASKTLTLH TSAKVLILVL KRFSDVTGNK LAKNVQYPEC  300
LDMQPYMSQQ NTGPLVYVLY AVLVHAGWSC HNGHYFSYVK AQEGQWYKMD DAEVTASSIT  360
```

```
SVLSQQAYVL FYIQKSEWER HSESVSRGRE PRALGAEDTD RRATQGELKR DHPCLQAPEL  420
DEHLVERATQ ESTLDHWKFL QEQNKTKPEF NVRKVEGTLP PDVLVIHQSK YKCGMKNHHP  480
EQQSSLLNLS STTPTHQESM NTGTLASLRG RARRSKGKNK HSKRALLVCQ             530

SEQ ID NO: 31          moltype = DNA  length = 1119
FEATURE                Location/Qualifiers
misc_feature           1..1119
                       note = Other DNA
source                 1..1119
                       mol_type = other DNA
                       organism = Homo sapiens
SEQUENCE: 31
atgagcaagg cgtttgggct cctgaggcaa atctgtcagt ccatcctggc tgagtcctcg  60
cagtccccgg cagatcttga agaaaagaag gaagaagaca gcaacatgaa gagagagcag  120
cccagagagc gtcccagggc ctgggactac cctcatggcc tggttggttt acacaacatt  180
ggacagacct gctgccttaa ctccttgatt caggtgttcg taatgaatgt ggacttcacc  240
aggatattga agaggatcac ggtgcccagg ggagctgacg agcagaggag aagcgtccct  300
ttccagatgc ttctgctgct ggagaagatg caggacagcc ggcagaaagc agtgcggccc  360
ctggagctgg cctactgcct gcagaagtgc aacgtgccct tgtttgtcca acatgatgct  420
gcccaactgt acctcaaact ctggaacctg attaaggacc agatcactga tgtgcacttg  480
gtggagagac tgcaggccct gtatacgatc cgggtgaagg actccttgat ttgcgttgac  540
tgtgccatgg agagtagcag aaacagcagc atgctcaccc tcccactttc tctttttgat  600
gtggactcaa agcccctgaa gacactggag gacgccctgc actgcttctt ccagcccagg  660
gagttatcaa gcaaaagcaa gtgcttctgt gagaactgtg ggaagaagac ccgtgggaaa  720
caggtcttga agctgaccca tttgccccag accctgacaa tccacctcat gcgattctcc  780
atcaggaatt cacagacgag aaagatctgc cactccctgt acttccccca gagcttggat  840
ttcagccaga tccttccaat gaagcgagag tcttgtgatg ctgaggagca gtctggaggg  900
cagtatgagc tttttgctgt gattgcgcac gtgggaatgg cagactccgg tcattactgt  960
gtctacatcc ggaatgctgt ggatggaaaa tggttctgct tcaatgactc caatatttgc  1020
ttggtgtcct gggaagacat ccagtgtacc tacggaaatc ctaactacca ctggcaggaa  1080
actgcatatc ttctggttta catgaagatg gagtgctaa                         1119

SEQ ID NO: 32          moltype = AA  length = 372
FEATURE                Location/Qualifiers
source                 1..372
                       mol_type = protein
                       organism = Homo sapiens
SEQUENCE: 32
MSKAFGLLRQ ICQSILAESS QSPADLEEKK EEDSNMKREQ PRERPRAWDY PHGLVGLHNI  60
GQTCCLNSLI QVFVMNVDFT RILKRITVPR GADEQRRSVP FQMLLLLEKM QDSRQKAVRP  120
LELAYCLQKC NVPLFVQHDA AQLYLKLWNL IKDQITDVHL VERLQALYTI RVKDSLICVD  180
CAMESSRNSS MLTLPLSLFD VDSKPLKTLE DALHCFFQPR ELSSKSKCFC ENCGKKTRGK  240
QVLKLTHLPQ TLTIHLMRFS IRNSQTRKIC HSLYFPQSLD FSQILPMKRE SCDAEEQSGG  300
QYELFAVIAH VGMADSGHYC VYIRNAVDGK WFCFNDSNIC LVSWEDIQCT YGNPNYHWQE  360
TAYLLVYMKM EC                                                      372

SEQ ID NO: 33          moltype = DNA  length = 3957
FEATURE                Location/Qualifiers
misc_feature           1..3957
                       note = Other DNA
source                 1..3957
                       mol_type = other DNA
                       organism = Homo sapiens
SEQUENCE: 33
atgtctggcg gggccagtgc cacaggccca aggagagggc ccccaggact ggaggacacc  60
actagtaaga agaagcagaa ggatcgagca aaccaggaga gcaaggatgg agatcctagg  120
aaagagacag ggtctcgata tgttgcccag gctggtcttg aacctctggc ctcaggtgat  180
ccttctgcct cagcctccca tgcagctggg atcacaggct cacgccaccg tacccggctg  240
ttctttcctt catcgtcagg gtcagcatcc actcctcaag aggagcagac caaagaggga  300
gcttgtgaag accctcatga tctcttggct actcccactc cagagttgtt gctcgattgg  360
aggcagagtg cagaagaggt gattgtcaag cttcgtgtgg gagtaggtcc cctgcagctg  420
gaggatgtag atgctgcttt cacagataca gactgtgtgg tgcggtttgc aggtggtcag  480
cagtggggtg gtgtcttcta tgctgagata aaaagctctt gtgctaaagt gcaaacccgc  540
aagggcagtc tcctgcacct gacactgccc aaaaaggtgc ctatgctcac gtggccctcc  600
ctcctggttg aggctgatga acagctttgc ataccaccgc tgaactccca aacctgcctc  660
ctgggctcag aggagaattt agccccttg gcaggagaga aagcagtgcc tcccgggaat  720
gacccagtct ctccagccat ggtccggagc agaaaccctg ggaaagatga ctgtgccaag  780
gaggagatgg cagtggcagc agatgctgca accttggtgg atgagcccga gtcgatggtg  840
aacctggcgt ttgtcaagaa tgactcgtat gagaagggcc cggattcagt ggtggtgcac  900
gtgtacgtga aggagatctg cagggacacc tcaagagtac ttttccgtga gcaggacttc  960
acgctcatct tccagaccag ggatggaaac ttcctgaggc tgcacccggg ctgtgggccc  1020
cacaccacct tccgttggca ggtgaagctc aggaatctga ttgagccaga gcagtgcacc  1080
ttctgtttca cggcttctcg catcgacatc tgccttcgta agaggcagag tcagcgctgg  1140
gggggcctgg aggccccggc tgcacgagtg ggtggtgcaa aggttgccgt gccgacaggt  1200
ccaacccctc tggattcaac cccaccagga ggtgctcccc accccctgac aggccaggag  1260
gaggcccggg ctgtggagaa ggataaatcc aaggcacgat ctgaggacac agggctagac  1320
agtgtggcaa cccgcacacc catggagcat gtaaccccaa agccagagac acacctggcc  1380
tcgcccaagc ctacatgcat ggtgcctccc atgccccaca gcccagttag tggagacagc  1440
gtggaggagg aggaagagga agagaagaag gtgtgtctgc caggcttcac tggccttgtc  1500
```

```
aatttaggca acacctgctt catgaacagc gtcattcagt ctctgtccaa cactcgggaa  1560
ctccgggact tcttccatga ccgctccttt gaggctgaga tcaactacaa caaccccacta  1620
gggactggtg ggcgtctggc cattggcttt gccgtgctgc ttcgggcgct gtggaagggc  1680
acccaccatg ccttccagcc ttccaagttg aaggccattg tggcgagtaa ggccagccag  1740
ttcacaggct atgcacagca tgatgcccag gagttcatgg ctttcctgct ggatgggctg  1800
cacgaggacc tgaatcgcat tcagaacaag ccctacacag agaccgtgga ttcagatggg  1860
cggcccgatg aggtggtagc tgaggaagca tggcagcggc acaagatgag gaatgactct  1920
ttcatcgtgg acctatttca ggggcagtac aagtcgaagc tggtgtgccc tgtgtgtgcc  1980
aaggtctcca tcacttttga cccgtttctt tatctgccgg tgcccttgcc acaaaagcaa  2040
aaggttctcc ctgtctttta ttttgcccga gagccccaca gcaagcccat caagttcctg  2100
gtgagcgtca gcaaggagaa ctccactgcg agcgaagtat tggactccct ctctcagagt  2160
gttcatgtga agcctgagaa cctgcgtttg gcggaggtaa ttaagaatcg ttttcatcgt  2220
gtgttcctac cctcccactc actggacact gtgtccccat ctgatacgct cctctgcttt  2280
gagctgctat cctcagagtt ggctaaggag cgggtagtgg tgctagaggt gcaacagcgc  2340
ccccaggtgc ccagcgtccc catctccaag tgtgcagcct gccagcggaa gcaacagtcg  2400
gaggatgaaa agctgaagcg ctgtacccgg tgctaccgtg tgggctactg caaccagctc  2460
tgccagaaaa cccactggcc tgaccacaag ggcctctgcc gacctgagaa cattggctac  2520
cccttcctgg tcagtgtacc tgcctcacgc ctcacttatg cccgcctcgc tcagttgcta  2580
gagggctatg cccggtactc tgtgagtgta ttccagccac cctttcagcc aggccgcatg  2640
gccttggagt ctcagagccc tggctgcacc acactgctct ccacaggttc cctggaggct  2700
ggggacagcg agagagaccc cattcagcca cctgagctcc agctggtgac ccctatggct  2760
gagggggaca cagggcttcc ccgggtgtgg gcagcccctg accggggtcc tgtgcccagc  2820
accagtggaa tttcttctga gatgctggcc agtgggccca ttgaggttgg ctccttgcca  2880
gctggcgaga gggtgtcccg acccgaagct gctgtgcctg ggtaccagca tccaagtgaa  2940
gctatgaatg cccacacacc ccagttcttc atctataaaa ttgattcatc caaccgagag  3000
cagcggctag aggacaaagg agacacccca ctggagctgg gtgacgactg tagcctggct  3060
ctcgtctggc ggaacaatga gcgcttgcag gagtttgtgt tggtagcctc caaggagctg  3120
gaatgtgctg aggatccagg ctctgccggt gaggctgccc gggccggcca cttcaccctg  3180
gaccagtgcc tcaacctctt cacacggcct gaggtgctgg cacccgagga ggcctggtac  3240
tgcccacagt gcaaacagca ccgtgaggcc tccaagcagc tgttgctatg gcgcctgcca  3300
aatgttctca tcgtgcagct caagcgcttc tcctttcgta gttttatctg gcgtgacaag  3360
atcaatgact tggtggagtt ccctgttagg aacctggacc tgagcaagtt ctgcattggt  3420
cagaaagagg agcagctgcc cagctacgat ctatatgctg tcatcaacca ctatggaggc  3480
atgattggtg gccactacac tgcctgtgca cgcctgccca atgatcgtag cagtcagcgc  3540
agtgacgtgg gctggcgctt gtttgatgac agcacagtga caacggtaga cgagagccag  3600
gttgtgacgc gttatgccta tgtactcttc taccgccggc ggaactctcc tgtggagagg  3660
cccccccaggg caggtcactc tgagcaccac ccagacctag gccctgcagc tgaggctgct  3720
gccagccagg cttcccggat ttggcaggag ctggaggctg aggaggagcc ggtgcctgag  3780
gggtctgggc ccctgggtcc ctgggggccc caagactggg tgggcccccct accacgtggc  3840
cctaccacac cagatgaggg ctgcctccgg tactttgtcc tgggcaccgt ggcggctttg  3900
gtggccctcg tgctcaacgt gttctatcct ctggtatccc agagtcgctg gagatga     3957

SEQ ID NO: 34          moltype = AA  length = 1318
FEATURE                Location/Qualifiers
source                 1..1318
                       mol_type = protein
                       organism = Homo sapiens
SEQUENCE: 34
MSGGASATGP RRGPPGLEDT TSKKKQKDRA NQESKDGDPR KETGSRYVAQ AGLEPLASGD  60
PSASASHAAG ITGSRHRTRL FFPSSSGSAS TPQEEQTKEG ACEDPHDLLA TPTPELLLDW  120
RQSAEEVIVK LRVGVGPLQL EDVDAAFTDT DCVVRFAGGQ QWGGVFYAEI KSSCAKVQTR  180
KGSLLHLTLP KKVPMLTWPS LLVEADEQLC IPPLNSQTCL LGSEENLAPL AGEKAVPPGN  240
DPVSPAMVRS RNPGKDDCAK EEMAVAADAA TLVDEPESMV NLAFVKNDSY EKGPDSVVVH  300
VYVKEICRDT SRVLFREQDF TLIFQTRDGN FLRLHPGCGP HTTFRWQVKL RNLIEPEQCT  360
FCFTASRIDI CLRKRQSQRW GGLEAPAARV GGAKVAVPTG PTPLDSTPPG GAPHPLTGQE  420
EARAVEKDKS KARSEDTGLD SVATRTPMEH VTPKPETHLA SPKPTCMVPP MPHSPVSGDS  480
VEEEEEEEKK VCLPGFTGLV NLGNTCFMNS VIQSLSNTRE LRDFFHDRSF EAEINYNNPL  540
GTGGRLAIGF AVLLRALWKG THHAFQPSKL KAIVASKASQ FTGYAQHDAQ EFMAFLLDGL  600
HEDLNRIQNK PYTETVDSDG RPDEVVAEEA WQRHKMRNDS FIVDLFQGQY KSKLVCPVCA  660
KVSITFDPFL YLPVPLPQKQ KVLPVFYFAR EPHSKPIKFL VSVSKENSTA SEVLDSLSQS  720
VHVKPENLRL AEVIKNRFHR VFLPSHSLDT VSPSDTLLCF ELLSSELAKE RVVVLEVQQR  780
PQVPSVPISK CAACQRKQQS EDEKLKRCTR CYRVGYCNQL CQKTHWPDHK GLCRPENIGY  840
PFLVSVPASR LTYARLAQLL EGYARYSVSV FQPPFQPGRM ALESQSPGCT TLLSTGSLEA  900
GDSERDPIQP PELQLVTPMA EGDTGLPRVW AAPDRGPVPS TSGISSEMLA SGPIEVGSLP  960
AGERVSRPEA AVPGYQHPSE AMNAHTPQFF IYKIDSSNRE QRLEDKGDTP LELGDDCSLA  1020
LVWRNNERLQ EFVLVASKEL ECAEDPGSAG EAARAGHFTL DQCLNLFTRP EVLAPEEAWY  1080
CPQCKQHREA SKQLLLWRLP NVLIVQLKRF SFRSFIWRDK INDLVEFPVR NLDLSKFCIG  1140
QKEEQLPSYD LYAVINHYGG MIGGHYTACA RLPNDRSSQR SDVGWRLFDD STVTTVDESQ  1200
VVTRYAYVLF YRRRNSPVER PPRAGHSEHH PDLGPAAEAA ASQASRIWQE LEAEEEPVPE  1260
GSGPLGPWGP QDWVGPLPRG PTTPDEGCLR YFVLGTVAAL VALVLNVFYP LVSQSRWR    1318

SEQ ID NO: 35          moltype = DNA  length = 2742
FEATURE                Location/Qualifiers
misc_feature           1..2742
                       note = Other DNA
source                 1..2742
                       mol_type = other DNA
                       organism = Homo sapiens
SEQUENCE: 35
```

```
atgggggact ccagggacct ttgccctcac cttgactcca taggagaggt gaccaaagag  60
gacttgctgc tcaaatctaa gggaacctgt cagtcgtgtg ggtcaccgg accaaaccta  120
tgggcctgtc tgcaggttgc ctgcccctat gttggctgcg gagaatcctt cgctgaccac  180
agcaccattc atgcacaggc aaaaaagcac aacttgaccg tgaacctgac cacgttccga  240
ctgtggtgtt acgcctgtga gaaggaggta ttcctggagc agcggctggc agcccctctg  300
ctgggctcct cttccaagtt ctctgaacag gactccccgc caccctccca ccctctgaaa  360
gctgttccta ttgctgtggc tgatgaagga gagtctgagt cagaggatga tgacctgaaa  420
cctcgaggcc tcacgggcat gaagaacctc gggaactcct gctacatgaa cgccgccctg  480
caggccctgt ccaattgccc gccgctgact cagttcttct tggagtgtgg cggcctggtg  540
cgcacagata agaagccagc cctgtgcaag agctaccaga agctggtctc tgaggtctgg  600
cataagaaac ggccaagcta cgtggtcccc accagtctgt ctcatgggat caagttggtc  660
aacccaatgt tccgaggcta tgcccagcag gacacccaag agttccttcg ctgcctgatg  720
gaccagctgc acgaggagct caaggagccg gtggtggcca cggtggcgct gacggaggct  780
cgggactcag attcgagtga cacggatgag aaacgggagg gtgaccggag cccatcagaa  840
gatgagttct tgtcctgtga ctcgagcagt gaccggggtg agggtgacgg gcaggggcgt  900
ggcgggggca gctcgcaggc cgagacggag ctgctgatcc cagatgaggc gggccgagcc  960
atctctgaga aggagcggat gaaggaccgc aagttctcct ggggccagca gcgtacaaac  1020
tcggagcaag tggacgagga cgctgatgtg gacactgcca tggctgccct tgaccagccc  1080
gcggaggccc agcccccgtc accacggtcc tccagcccct gccggacgcc agagccggac  1140
aatgatgctc acctacgcag ctcctctcgc ccctgcagcc ccgtccacca ccacgagggc  1200
catgccaagc tgtctagcag ccccccctcgt gcaagccccg tgaggatggc accgtcgtac  1260
gtgctcaaga aagcccaggt attgagtgct ggcagccgga ggcggaagga gcagcgctac  1320
cgcagcgtca tctcagacat ctttgacggc tccattctca gcctcgtgca gtgtctcacc  1380
tgtgaccggg tatccaccac agtggaaacg ttccaggact tatcactgcc cattcctgga  1440
aaggaggacc tggccaagct ccattcagcc atctaccaga atgtgccggc caagccaggc  1500
gcctgtgggg acagctatgc cgcccagggc tggctggcct tcattgtgga gtacatccga  1560
cggtttgtgg tatcctgtac ccccagctgg ttttgggggc ctgtcgtcac cctggaagac  1620
tgccttgctg ccttctttgc cgctgatgag ttaaagggtg acaacatgta cagctgtgag  1680
cggtgtaaga agctgcggaa cggagtgaag tactgcaaag tcctgcggtt gcccgagatc  1740
ctgtgcattc acctaaagcg ctttcggcac gaggtgatgt actcattcaa gatcaacagc  1800
cacgtctcct tcccctcga ggggctcgac ctgcgcccct tccttgccaa ggagtgcaca  1860
tcccagatca ccacctacga cctcctctcg gtcatctgcc accacggcac ggcaggcagt  1920
gggcactaca tcgcctactg ccagaacgtg atcaatgggc agtggtacga gtttgatgac  1980
cagtacgtca cagaagtcca cgagacggtg gtgcagaacg ccgagggcta cgtactcttc  2040
tacaggaaga gcagcgagga ggccatgcgg gagcgacagc aggtggtgtc cctggccgcc  2100
atgcgggagc ccagcctgct gcggttctac gtgtcccgcg agtggctcaa caagttcaac  2160
accttcgcgg agccaggccc catcaccaac cagaccttcc tctgctccca cggaggcatc  2220
ccgcccccaca aataccacta catcgacgac ctggtggtca tcctgcccca gaacgtctgg  2280
gagcacctgt acaacagatt cgggggtggc cccgccgtga accacctgta cgtgtgctcc  2340
atctgccagg tggagatcga ggcactggcc aagcgcagga ggatcgagat cgacaccttc  2400
atcaagttga acaaggcctt ccaggccgag gagtcgccgg gcgtcatcta ctgcatcagc  2460
atgcagtggt tccgggagtg ggaggcgttc gtcaagggga aggacaacga gccccccggg  2520
cccattgaca acagcaggat tgcacaggtc aaaggaagcg gccatgtcca gctgaagcag  2580
ggagctgact acgggcagat ttcggaggag acctggacct acctgaacag cctgtatgga  2640
ggtggccccg agattgccat ccgccagagt gtggcgcagc cgctgggccc agagaacctg  2700
cacggggagc agaagatcga agccgagacg cgggccgtgt ga  2742
```

```
SEQ ID NO: 36          moltype = AA  length = 913
FEATURE                Location/Qualifiers
source                 1..913
                       mol_type = protein
                       organism = Homo sapiens
SEQUENCE: 36
MGDSRDLCPH LDSIGEVTKE DLLLKSKGTC QSCGVTGPNL WACLQVACPY VGCGESFADH  60
STIHAQAKKH NLTVNLTTFR LWCYACEKEV FLEQRLAAPL LGSSSKFSEQ DSPPPSHPLK  120
AVPIAVADEG ESESEDDDLK PRGLTGMKNL GNSCYMNAAL QALSNCPPLT QFFLECGGLV  180
RTDKKPALCK SYQKLVSEVW HKKRPSYVVP TSLSHGIKLV NPMFRGYAQQ DTQEFLRCLM  240
DQLHEELKEP VVATVALTEA RDSDSSDTDE KREGDRSPSE DEFLSCDSSS DRGEGDGQGR  300
GGGSSQAETE LLIPDEAGRA ISEKERMKDR KFSWGQQRTN SEQVDEDADV DTAMAALDQP  360
AEAQPPSPRS SSPCRTPEPD NDAHLRSSSR PCSPVHHHEG HAKLSSSPPR ASPVRMAPSY  420
VLKKAQVLSA GSRRRKEQRY RSVISDIFDG SILSLVQCLT CDRVSTTVET FQDLSLPIPG  480
KEDLAKLHSA IYQNVPAKPG ACGDSYAAQG WLAFIVEYIR RFVVSCTPSW FWGPVVTLED  540
CLAAFFAADE LKGDNMYSCE RCKKLRNGVK YCKVLRLPEI LCIHLKRFRH EVMYSFKINS  600
HVSFPLEGLD LRPFLAKECT SQITTYDLLS VICHHGTAGS GHYIAYCQNV INGQWYEFDD  660
QYVTEVHETV VQNAEGYVLF YRKSSEEAMR ERQQVVSLAA MREPSLLRFY VSREWLNKFN  720
TFAEPGPITN QTFLCSHGGI PPHKYHYIDD LVVILPQNVW EHLYNRFGGG PAVNHLYVCS  780
ICQVEIEALA KRRRIEIDTF IKLNKAFQAE ESPGVIYCIS MQWFREWEAF VKGKDNEPPG  840
PIDNSRIAQV KGSGHVQLKQ GADYGQISEE TWTYLNSLYG GGPEIAIRQS VAQPLGPENL  900
HGEQKIEAET RAV                                                     913

SEQ ID NO: 37          moltype = DNA  length = 3168
FEATURE                Location/Qualifiers
misc_feature           1..3168
                       note = Other DNA
source                 1..3168
                       mol_type = other DNA
                       organism = Homo sapiens
SEQUENCE: 37
atgaccgtgg agcagaacgt gctgcagcag agcgcggcgc agaagcacca gcagacgttt  60
```

-continued

```
ttgaatcaac tgagagaaat tacggggatt aatgacaccc agatactaca gcaagccttg  120
aaggatagta atggaaactt ggaattagca gtggctttcc ttactgcgaa gaatgctaag  180
acccctcagc aggaggagac aacttactac caaacagcac ttcctggcaa tgatagatac  240
atcagtgtgg gaagccaagc agatacaaat gtgattgatc tcactggaga tgataaagat  300
gatcttcaga gagcaattgc cttgagtttg gccgaatcaa acagggcatt cagggagact  360
ggaataactg atgaggaaca agccattagc agagttcttg aagccagcat agcagagaat  420
aaagcatgtt tgaagaggac acctacagaa gtttggaggg attctcgaaa cccttatgat  480
agaaaaagac aggacaaagc tcccgttggg ctaaagaatg ttggcaatac ttgttggttt  540
agtgctgtta ttcagtcatt atttaatctt ttggaattta gaagattagt tctgaattac  600
aagcctccat caaatgctca agatttaccc cgaaaccaaa aggaacatcg gaatttgcct  660
tttatgcgtg agctgaggta tctatttgca cttcttgttg gtaccaaaag gaagtatgtt  720
gatccatcaa gagcagttga aattcttaag gatgctttca aatcaaatga ctcacagcag  780
caagatgtga gtgagtttac acacaaatta ttagattggt tagaagatgc cttccaaatg  840
aaagctgaag aggagacgga tgaagagaag ccaaagaacc ccatggtaga gttgttctat  900
ggcagattcc tggctgtggg agtacttgaa ggtaaaaaat ttgaaaacac tgaaatgttt  960
ggtcagtacc cacttcaggt caatgggttc aaagatctgc atgagtgcct agaagctgca  1020
atgattgaag gagaaattga gtctttacat tcagagaatt caggaaaatc aggccaagag  1080
cattggttta ctgaattacc acctgtgtta acatttgaat tgtcaagatt tgaatttaat  1140
caggcattgg gaagaccaga aaaaattcac aacaaattag aatttcccca agttttatat  1200
ttggacagat acatgcacag aaacagagaa ataacaagaa ttaagaggga agagatcaag  1260
agactgaaag attacctcac ggtattacaa caaaggctag aaagatattt aagctatggt  1320
tccggtccca aacgattccc cttggtagat gttcttcagt atgcattgga atttgcctca  1380
agtaaacctg tttgcacttc tcctgttgac gatattgacg ctagttcccc acctagtggt  1440
tccataccat cacagacatt accaagcaca acagaacaac agggagccct atcttcagaa  1500
ctgccaagca catcaccttc atcagttgct gccatttcat cgagatcagt aatacacaaa  1560
ccatttactc agtcccggat acctccagat ttgcccatgc atccggcacc aaggcacata  1620
acggaggaag aactttctgt gctggaaagt tgtttacatc gctggaggac agaaatagaa  1680
aatgacacca gagatttgca ggaaagcata tccagaatcc atcgaacaat tgaattaatg  1740
tactctgaca aatctatgat acaagttcct tatcgattac atgccgtttt agttcacgaa  1800
ggccaagcta atgctgggca ctactgggca tatatttttg atcatcgtga aagcagatgg  1860
atgaagtaca atgatattgc tgtgacaaaa tcatcatggg aagagctagt gagggactct  1920
tttggtggtt atagaaatgc cagtgcatac tgtttaatgt acataaatga taaggcacag  1980
ttcctaatac aagaggagtt taataaagaa actgggcagc cccttgttgg tatagaaaca  2040
ttaccaccgg atttgagaga ttttgttgag gaagacaacc aacgatttga aaaagaacta  2100
gaagaatggg atgcacaact tgcccagaaa gctttgcagg aaaagctttt agcgtctcag  2160
aaattgagag agtcagagac ttctgtgaca acagcacaag cagcaggaga cccagaatat  2220
ctagagcagc catcaagaag tgatttctca aagcacttga aagaagaaac tattcaaata  2280
attaccaagg catcacatga gcatgaagat aaaagtcctg aaacagtttt gcagtcggca  2340
attaagttgg aatatgcaag gttggttaag ttggcccaag aagacacccc accagaaacc  2400
gattatcgtt tacatcatgt agtggtctac tttatccaga accaggcacc aaagaaaatt  2460
attgagaaaa cattactaga acaatttgga gatagaaatt tgagttttga tgaaaggtgt  2520
cacaacataa tgaaagttgc tcaagccaaa ctggaaatga taaaacctga agaagtaaac  2580
ttggaggaat atgaggagtg gcatcaggat tataggaaat tcagggaaac aactatgtat  2640
ctcataattg ggctagaaaa ttttcaaaga gaaagttata tagattcctt gctgttcctc  2700
atctgtgctt atcagaataa caaagaactc ttgtctaaag gcttatacag aggacatgat  2760
gaagaattga tatcacatta tagaagagaa tgtttgctaa aattaaatga gcaagccgca  2820
gaactcttcg aatctggaga ggatcgagaa gtaaacaatg gtttgattat catgaatgag  2880
tttattgtcc catttttgcc attattactg gtggatgaaa tggaagaaaa ggatatacta  2940
gctgtagaag atatgagaaa tcgatggtgt tcctaccttg gtcaagaaat ggaaccacac  3000
ctccaagaaa agctgacaga ttttttgcca aaactgcttg attgttctat ggagattaaa  3060
agtttccatg agccaccgaa gttaccttca tattccacgc atgaactctg tgagcgattt  3120
gcccgaatca tgttgtccct cagtcgaact cctgctgatg gaagataa              3168

SEQ ID NO: 38          moltype = AA  length = 1055
FEATURE                Location/Qualifiers
source                 1..1055
                       mol_type = protein
                       organism = Homo sapiens
SEQUENCE: 38
MTVEQNVLQQ SAAQKHQQTF LNQLREITGI NDTQILQQAL KDSNGNLELA VAFLTAKNAK  60
TPQQEETTYY QTALPGNDRY ISVGSQADTN VIDLTGDDKD DLQRAIALSL AESNRAFRET  120
GITDEEQAIS RVLEASIAEN KACLKRTPTE VWRDSRNPYD RKRQDKAPVG LKNVGNTCWF  180
SAVIQSLFNL LEFRRLVLNY KPPSNAQDLP RNQKEHRNLP FMRELRYLFA LLVGTKRKYV  240
DPSRAVEILK DAFKSNDSQQ QDVSEFTHKL LDWLEDAFQM KAEEETDEEK PKNPMVELFY  300
GRFLAVGVLE GKKFENTEMF GQYPLQVNGF KDLHECLEAA MIEGEIESLH SENSGKSGQE  360
HWFTELPPVL TFELSRFEFN QALGRPEKIH NKLEFPQVLY LDRYMHRNRE ITRIKREEIK  420
RLKDYLTVLQ QRLERYLSYG SGPKRFPLVD VLQYALEFAS SKPVCTSPVD DIDASSPPSG  480
SIPSQTLPST TEQQGALSSE LPSTSPSSVA AISSRSVIHK PFTQSRIPPD LPMHPAPRHI  540
TEEELSVLES CLHRWRTEIE NDTRDLQESI SRIHRTIELM YSDKSMIQVP YRLHAVLVHE  600
GQANAGHYWA YIFDHRESRW MKYNDIAVTK SSWEELVRDS FGGYRNASAY CLMYINDKAQ  660
FLIQEEFNKE TGQPLVGIET LPPDLRDFVE EDNQRFEKEL EEWDAQLAQK ALQEKLLASQ  720
KLRESETSVT TAQAAGDPEY LEQPSRSDFS KHLKEETIQI ITKASHEHED KSPETVLQSA  780
IKLEYARLVK LAQEDTPPET DYRLHHVVVY FIQNQAPKKI IEKTLLEQFG DRNLSFDERC  840
HNIMKVAQAK LEMIKPEEVN LEEYEEWHQD YRKFRETTMY LIIGLENFQR ESYIDSLLFL  900
ICAYQNNKEL LSKGLYRGHD EELISHYRRE CLLKLNEQAA ELFESGEDRE VNNGLIIMNE  960
FIVPFLPLLL VDEMEEKDIL AVEDMRNRWC SYLGQEMEPH LQEKLTDFLP KLLDCSMEIK  1020
SFHEPPKLPS YSTHELCERF ARIMLSLSRT PADGR                            1055

SEQ ID NO: 39          moltype = DNA  length = 3264
```

```
FEATURE               Location/Qualifiers
misc_feature          1..3264
                      note = Other DNA
source                1..3264
                      mol_type = other DNA
                      organism = Homo sapiens
SEQUENCE: 39
atgaccgtgg agcagaacgt gctgcagcag agcgcggcgc agaagcacca gcagacgttt  60
ttgaatcaac tgagagaaat tacggggatt aatgacaccc agatactaca gcaagccttg  120
aaggatagta atggaaactt ggaattagca gtggctttcc ttactgcgaa gaatgctaag  180
acccctcagc aggaggagac aacttactac caaacagcac ttcctggcaa tgatagatac  240
atcagtgtgg gaagccaagc agatacaaat gtgattgatc tcactggaga tgataaagat  300
gatcttcaga gagcaattgc cttgagtttg gccgaatcaa acagggcatt cagggagact  360
ggaataactg atgaggaaca agccattagc agagttcttg aagccagcat agcagagaat  420
aaagcatgtt tgaagaggac acctacagaa gtttggaggg attctcgaaa cccttatgat  480
agaaaaagac aggacaaagc tcccgttggg ctaaagaatg ttggcaatac ttgttggttt  540
agtgctgtta ttcagtcatt atttaatctt ttggaattta gaagattagt tctgaattac  600
aagcctccat caaatgctca agatttaccc cgaaaccaaa aggaacatcg gaatttgcct  660
tttatgcgtg agctgaggta tctatttgca cttcttgttg gtaccaaaag gaagtatgtt  720
gatccatcaa gagcagttga aattcttaag gatgctttca aatcaaatga ctcacagcag  780
caagatgtga gtgagtttac acacaaatta ttagattggt tagaagatgc cttccaaatg  840
aaagctgaag aggagacgga tgaagagaag ccaaagaacc ccatggtaga gttgttctat  900
ggcagattcc tggctgtggg agtacttgaa ggtaaaaaat ttgaaaacac tgaaatgttt  960
ggtcagtacc cacttcaggt caatgggttc aaagatctgc atgagtgcct agaagctgca  1020
atgattgaag gagaaattga gtctttacat tcagagaatt caggaaaatc aggccaagag  1080
cattggttta ctgaattacc acctgtgtta acatttgaat tgtcaagatt tgaatttaat  1140
caggcattgg gaagaccaga aaaaattcac aacaaattag aatttcccca agttttatat  1200
ttggacagat acatgcacag aaacagagaa ataacaagaa ttaagaggga agagatcaag  1260
agactgaaag attacctcac ggtattacaa caaaggctag aaagatattt aagctatggt  1320
tccggtccca aacgattccc cttggtagat gttcttcagt atgcattgga atttgcctca  1380
agtaaacctg tttgcacttc tcctgttgac gatattgacg ctagttcccc acctagtggt  1440
tccataccat cacagacatt accaagcaca acagaacaac agggagccct atcttcagaa  1500
ctgccaagca catcaccttc atcagttgct gccatttcat cgagatcagt aatacacaaa  1560
ccatttactc agtcccggat acctccagat ttgcccatgc atccggcacc aaggcacata  1620
acggaggaaa aactttctgt gctggaaagt tgtttacatc gctggaggac agaaatagaa  1680
aatgacacca gagatttgca ggaaagcata tccagaatcc atcgaacaat tgaattaatg  1740
tactctgaca aatctatgat acaagttcct tatcgattac atgccgtttt agttcacgaa  1800
ggccaagcta atgctgggca ctactgggca tatatttttg atcatcgtga aagcagatgg  1860
atgaagtaca atgatattgc tgtgacaaaa tcatcatggg aagagctagt gagggactct  1920
tttggtggtt atagaaatgc cagtgcatac tgtttaatgt acataaatga taaggcacag  1980
ttcctaatac aagaggagtt taataaagaa actgggcagc cccttgttgg tatagaaaca  2040
ttaccaccgg atttgagaga ttttgttgag gaagacaacc aacgatttga aaaagaacta  2100
gaagaatggg atgcacaact tgcccagaaa gctttgcagg aaaagctttt agcgtctcag  2160
aaattgagag agtcagagac ttctgtgaca acagcacaag cagcaggaga cccagaatat  2220
ctagagcagc catcaagaag tgatttctca aagcacttga aagaagaaac tattcaaata  2280
attaccaagg catcacatga gcatgaagat aaaagtcctg aaacagtttt gcagtcgatc  2340
atgatgacac cgaacatgca aggtattatc atggcgatag gtaaatccag gagtgtatat  2400
gacaggtgtg gccctgaagc agggttcttt aaggcaatta agttggaata tgcaaggttg  2460
gttaagttgg cccaagaaga cacccccacca gaaaccgatt atcgtttaca tcatgtagtg  2520
gtctacttta tccagaacca ggcaccaaag aaaattattg agaaaacatt actagaacaa  2580
tttggagata gaaatttgag ttttgatgaa aggtgtcaca acataatgaa agttgctcaa  2640
gccaaactgg aaatgataaa acctgaagaa gtaaacttgg aggaatatga ggagtggcat  2700
caggattata ggaaattcag ggaaacaact atgtatctca taattgggct agaaaatttt  2760
caaagagaaa gttatataga ttccttgctg ttcctcatct gtgcttatca gaataacaaa  2820
gaactcttgt ctaaaggctt atacagagga catgatgaag aattgatatc acattataga  2880
agagaatgtt tgctaaaatt aaatgagcaa gccgcagaac tcttcgaatc tggagaggat  2940
cgagaagtaa acaatggttt gattatcatg aatgagttta ttgtcccatt tttgccatta  3000
ttactggtgg atgaaatgga agaaaaggat atactagctg tagaagatat gagaaatcga  3060
tggtgttcct accttggtca agaaatggaa ccacacctcc aagaaaagct gacagatttt  3120
ttgccaaaac tgcttgattg ttctatggag attaaaagtt tccatgagcc accgaagtta  3180
ccttcatatt ccacgcatga actctgtgag cgatttgccc gaatcatgtt gtccctcagt  3240
cgaactcctg ctgatggaag ataa                                         3264

SEQ ID NO: 40         moltype = AA  length = 1087
FEATURE               Location/Qualifiers
source                1..1087
                      mol_type = protein
                      organism = Homo sapiens
SEQUENCE: 40
MTVEQNVLQQ SAAQKHQQTF LNQLREITGI NDTQILQQAL KDSNGNLELA VAFLTAKNAK  60
TPQQEETTYY QTALPGNDRY ISVGSQADTN VIDLTGDDKD DLQRAIALSL AESNRAFRET  120
GITDEEQAIS RVLEASIAEN KACLKRTPTE VWRDSRNPYD RKRQDKAPVG LKNVGNTCWF  180
SAVIQSLFNL LEFRRLVLNY KPPSNAQDLP RNQKEHRNLP FMRELRYLFA LLVGTKRKYV  240
DPSRAVEILK DAFKSNDSQQ QDVSEFTHKL LDWLEDAFQM KAEEETDEEK PKNPMVELFY  300
GRFLAVGVLE GKKFENTEMF GQYPLQVNGF KDLHECLEAA MIEGEIESLH SENSGKSGQE  360
HWFTELPPVL TFELSRFEFN QALGRPEKIH NKLEFPQVLY LDRYMHRNRE ITRIKREEIK  420
RLKDYLTVLQ QRLERYLSYG SGPKRFPLVD VLQYALEFAS SKPVCTSPVD DIDASSPPSG  480
SIPSQTLPST TEQQGALSSE LPSTSPSSVA AISSRSVIHK PFTQSRIPPD LPMHPAPRHI  540
TEEKLSVLES CLHRWRTEIE NDTRDLQESI SRIHRTIELM YSDKSMIQVP YRLHAVLVHE  600
```

-continued

```
GQANAGHYWA YIFDHRESRW MKYNDIAVTK SSWEELVRDS FGGYRNASAY CLMYINDKAQ  660
FLIQEEFNKE TGQPLVGIET LPPDLRDFVE EDNQRFEKEL EEWDAQLAQK ALQEKLLASQ  720
KLRESETSVT TAQAAGDPEY LEQPSRSDFS KHLKEETIQI ITKASHEHED KSPETVLQSI  780
MMTPNMQGII MAIGKSRSVY DRCGPEAGFF KAIKLEYARL VKLAQEDTPP ETDYRLHHVV  840
VYFIQNQAPK KIIEKTLLEQ FGDRNLSFDE RCHNIMKVAQ AKLEMIKPEE VNLEEYEEWH  900
QDYRKFRETT MYLIIGLENF QRESYIDSLL FLICAYQNNK ELLSKGLYRG HDEELISHYR  960
RECLLKLNEQ AAELFESGED REVNNGLIIM NEFIVPFLPL LLVDEMEEKD ILAVEDMRNR  1020
WCSYLGQEME PHLQEKLTDF LPKLLDCSME IKSFHEPPKL PSYSTHELCE RFARIMLSLS  1080
RTPADGR                                                            1087

SEQ ID NO: 41          moltype = DNA  length = 3234
FEATURE                Location/Qualifiers
misc_feature           1..3234
                       note = Other DNA
source                 1..3234
                       mol_type = other DNA
                       organism = Homo sapiens
SEQUENCE: 41
atgactgcgg agctgcagca ggacgacgcg gccggcgcgg cagacggcca cggctcgagc  60
tgccaaatgc tgttaaatca actgagagaa atcacaggca ttcaggaccc ttcctttctc  120
catgaagctc tgaaggccag taatggtgac attactcagg cagtcagcct tctcactgat  180
gagagagtta aggagcccag tcaagacact gttgctacag aaccatctga agtagagggg  240
agtgctgcca acaaggaagt attagcaaaa gttatagacc ttactcatga taacaaagat  300
gatcttcagg ctgccattgc tttgagtcta ctggagtctc ccaaaattca agctgatgga  360
agagatctta acaggatgca tgaagcaacc tctgcagaaa ctaaacgctc aaagagaaaa  420
cgctgtgaag tctggggaga aaaccccaat cccaatgact ggaggagagt tgatggttgg  480
ccagttgggc tgaaaaatgt tggcaataca tgttggttta gtgctgttat tcagtctctc  540
tttcaattgc ctgaatttcg aagacttgtt ctcagttata gtctgccaca aaatgtactt  600
gaaaattgtc gaagtcatac agaaaagaga aatatcatgt ttatgcaaga gcttcagtat  660
ttgtttgctc taatgatggg atcaaataga aaatttgtag acccgtctgc agccctggat  720
ctattaaagg gagcattccg atcatctgag gaacagcagc aagatgtgag tgaattcaca  780
cacaagctcc tggattggct agaggacgca ttccagctag ctgttaatgt taacagtccc  840
aggaacaaat ctgaaaatcc aatggtgcag ctgttctatg gtactttcct gactgaaggg  900
gttcgtgaag gaaaaccctt ttgtaacaat gagaccttcg gccagtatcc tcttcaggta  960
aacggttatc gcaacttaga cgagtgtttg gaaggggcca tggtggaggg tgatgttgag  1020
cttcttccct ccgatcactc ggtgaagtat ggacaagagc gttggtttac aaagctacct  1080
ccagtgttga cctttgaact ctcaagattt gagtttaatc agtcccttgg gcagccagag  1140
aaaattcaca ataagctgga atttcctcag attatttata tggacaggta catgtacagg  1200
agcaaggagc ttattcgaaa taagagagag tgtattcgaa agttgaagga ggaaataaaa  1260
attctgcagc aaaaattgga aaggtatgtg aaatatggct caggcccagc tcggttcccg  1320
ctcccggaca tgctgaaata tgttattgaa tttgctagta caaaacctgc ctcagaaagc  1380
tgtccacctg aaagtgacac acatatgaca ttaccacttt cttcagtgca ctgctcggtt  1440
tctgaccaga catccaagga aagtacaagt acagaaagct cttctcagga tgttgaaagt  1500
accttttctt ctcctgaaga ttctttaccc aagtctaaac cactgacatc ttctcggtct  1560
tccatggaaa tgccttcaca gccagctcca cgaacagtca cagatgagga gataaatttt  1620
gttaagacct gtcttcagag atggaggagt gagattgaac aagatataca agatttaaag  1680
acttgtattg caagtactac tcagactatt gaacagatgt actgcgatcc tctccttcgt  1740
caggtgcctt atcgcttgca tgcagttctt gttcatgaag gacaagcaaa tgctggacac  1800
tattgggcct atatctataa tcaaccccga cagagctggc tcaagtacaa tgacatctct  1860
gttactgaat cttcctggga agaagttgaa agagattcct atggaggcct gagaaatgtt  1920
agtgcttact gtctgatgta cattaatgac aaactaccct acttcaatgc agaggcagcc  1980
ccaactgaat cagatcaaat gtcagaagtg gaagccctat ctgtggaact caagcattac  2040
attcaggagg ataactggcg gtttgagcag gaagtagagg agtgggaaga agagcagtct  2100
tgcaaaatcc ctcaaatgga gtcctccacc aactcctcat cacaggacta ctctacatca  2160
caagagcctt cagtagcctc ttctcatggg gttcgctgct tgtcatctga gcatgctgtg  2220
attgtaaagg agcaaactgc ccaggctatt gcaaacacag cccgtgccta tgagaagagc  2280
ggtgtagaag cggcactgag tgaggtgatg ctgagccctg ccatgcaagg ggtcatcctg  2340
gccatagcta aagcccgtca gacctttgac cgagatgggt ctgaagcagg gctgattaag  2400
gcattccatg aagaatactc caggctctat cagcttgcca aagagacccc cacctctcac  2460
agtgatcctc gacttcagca tgtccttgtc tactttttcc aaaatgaagc acccaaaagg  2520
gtagtagaac gaacccttct ggaacagttt gcagataaaa atcttagcta tgatgaaaga  2580
tcaatcagca ttatgaaggt ggctcaagcg aaactgaagg aaattggtcc agatgacatg  2640
aatatggaag agtacaagaa gtggcatgaa gattatagtt tgttccgaaa agtgtctgtg  2700
tatctcctaa caggcctaga actctatcaa aaaggaaagt accaagaggc actttcctac  2760
ctggtatatg cctaccagag caatgctgcc ctgctgatga aggggccccg ccgggggtc  2820
aaagaatccg tgattgcttt ataccgaaga aaatgccttc tggagctgaa tgccaaagca  2880
gcttctcttt ttgaaacaaa tgatgatcac tccgtaactg agggcattaa tgtgatgaat  2940
gaactgatca tcccctgcat tcaccttatc attaataatg acatttccaa ggatgatctg  3000
gatgccattg aggtcatgag aaaccattgg tgctcttacc ttgggcaaga tattgcagaa  3060
aatctgcagc tgtgcctagg ggagtttcta cccagacttc tagatccttc tgcagaaatc  3120
atcgtcttga aagagcctcc aactattcga cccaattctc cctatgacct atgtagccga  3180
tttgcagctg tcatggagtc aattcaggga gtttcaactg tgacagtgaa ataa        3234

SEQ ID NO: 42          moltype = AA  length = 1077
FEATURE                Location/Qualifiers
source                 1..1077
                       mol_type = protein
                       organism = Homo sapiens
SEQUENCE: 42
```

```
MTAELQQDDA AGAADGHGSS CQMLLNQLRE ITGIQDPSFL HEALKASNGD ITQAVSLLTD  60
ERVKEPSQDT VATEPSEVEG SAANKEVLAK VIDLTHDNKD DLQAAIALSL LESPKIQADG  120
RDLNRMHEAT SAETKRSKRK RCEVWGENPN PNDWRRVDGW PVGLKNVGNT CWFSAVIQSL  180
FQLPEFRRLV LSYSLPQNVL ENCRSHTEKR NIMFMQELQY LFALMMGSNR KFVDPSAALD  240
LLKGAFRSSE EQQQDVSEFT HKLLDWLEDA FQLAVNVNSP RNKSENPMVQ LFYGTFLTEG  300
VREGKPFCNN ETFGQYPLQV NGYRNLDECL EGAMVEGDVE LLPSDHSVKY GQERWFTKLP  360
PVLTFELSRF EFNQSLGQPE KIHNKLEFPQ IIYMDRYMYR SKELIRNKRE CIRKLKEEIK  420
ILQQKLERYV KYGSGPARFP LPDMLKYVIE FASTKPASES CPPESDTHMT LPLSSVHCSV  480
SDQTSKESTS TESSSQDVES TFSSPEDSLP KSKPLTSSRS SMEMPSQPAP RTVTDEEINF  540
VKTCLQRWRS EIEQDIQDLK TCIASTTQTI EQMYCDPLLR QVPYRLHAVL VHEGQANAGH  600
YWAYIYNQPR QSWLKYNDIS VTESSWEEVE RDSYGGLRNV SAYCLMYIND KLPYFNAEAA  660
PTESDQMSEV EALSVELKHY IQEDNWRFEQ EVEEWEEEQS CKIPQMESST NSSSQDYSTS  720
QEPSVASSHG VRCLSSEHAV IVKEQTAQAI ANTARAYEKS GVEAALSEVM LSPAMQGVIL  780
AIAKARQTFD RDGSEAGLIK AFHEEYSRLY QLAKETPTSH SDPRLQHVLV YFFQNEAPKR  840
VVERTLLEQF ADKNLSYDER SISIMKVAQA KLKEIGPDDM NMEEYKKWHE DYSLFRKVSV  900
YLLTGLELYQ KGKYQEALSY LVYAYQSNAA LLMKGPRRGV KESVIALYRR KCLLELNAKA  960
ASLFETNDDH SVTEGINVMN ELIIPCIHLI INNDISKDDL DAIEVMRNHW CSYLGQDIAE  1020
NLQLCLGEFL PRLLDPSAEI IVLKEPPTIR PNSPYDLCSR FAAVMESIQG VSTVTVK     1077

SEQ ID NO: 43          moltype = DNA  length = 1554
FEATURE                Location/Qualifiers
misc_feature           1..1554
                       note = Other DNA
source                 1..1554
                       mol_type = other DNA
                       organism = Homo sapiens
SEQUENCE: 43
atgctgagct cccgggccga ggcggcgatg accgcggccg acagggccat ccagcgcttc  60
ctgcggaccg gggcggccgt cagatataaa gtcatgaaga actggggagt tataggtgga  120
attgctgctg ctcttgcagc aggaatatat gttatttggg gtcccattac agaaaagaaag  180
aagcgtagaa aagggcttgt gcctggcctt gttaatttag ggaacacctg cttcatgaac  240
tccctgctac aaggcctgtc tgcctgtcct gctttcatca ggtggctgga agagttcacc  300
tcccagtact ccagggatca gaaggagccc ccctcacacc agtatttatc cttaacactc  360
ttgcaccttc tgaaagcctt gtcctgccaa gaagttactg atgatgaggt cttagatgca  420
agctgcttgt tggatgtctt aagaatgtac agatggcaga tctcatcatt tgaagaacag  480
gatgctcacg aattattcca tgtcattacc tcgtcattgg aagatgagcg agaccgccag  540
cctcgggtca cacatttgtt tgatgtgcat tccctggagc agcagtcaga aataactccc  600
aaacaaatta cctgccgcac aagagggtca cctcacccca catccaatca ctggaagtct  660
caacatcctt ttcatggaag actcactagt aatatggtct gcaaacactg tgaacaccag  720
agtcctgttc gatttgatac ctttgatagc ctttcactaa gtattccagc cgccacatgg  780
ggtcacccat tgaccctgga ccactgcctt caccacttca tctcatcaga atcagtgcgg  840
gatgttgtgt gtgacaactg tacaaagatt gaagccaagg gaacgttgaa cggggaaaag  900
gtggaacacc agaggaccac ttttgttaaa cagttaaaac tagggaagct ccctcagtgt  960
ctctgcatcc acctacagcg gctgagctgg tccagccacg gcacgcctct gaagcggcat  1020
gagcacgtgc agttcaatga gttcctgatg atggacattt acaagtacca cctccttgga  1080
cataaaccta gtcaacacaa ccctaaactg aacaagaacc cagggcctac actggagctg  1140
caggatgggc cgggagcccc cacaccagtt ctgaatcagc caggggcccc caaaacacag  1200
atttttatga atggcgcctg ctccccatct ttattgccaa cgctgtcagc gccgatgccc  1260
ttccctctcc cagttgttcc cgactacagc tcctccacat acctcttccg gctgatggca  1320
gttgtcgtcc accatggaga catgcactct ggacactttg tcacttaccg acggtcccca  1380
ccttctgcca ggaaccctct ctcaactagc aatcagtggc tgtgggtctc cgatgacact  1440
gtccgcaagg ccagcctgca ggaggtcctg tcctccagcg cctacctgct gttctacgag  1500
cgcgtccttt ccaggatgca gcaccagagc caggagtgca agtctgaaga atga        1554

SEQ ID NO: 44          moltype = AA  length = 517
FEATURE                Location/Qualifiers
source                 1..517
                       mol_type = protein
                       organism = Homo sapiens
SEQUENCE: 44
MLSSRAEAAM TAADRAIQRF LRTGAAVRYK VMKNWGVIGG IAAALAAGIY VIWGPITERK  60
KRRKGLVPGL VNLGNTCFMN SLLQGLSACP AFIRWLEEFT SQYSRDQKEP PSHQYLSLTL  120
LHLLKALSCQ EVTDDEVLDA SCLLDVLRMY RWQISSFEEQ DAHELFHVIT SSLEDERDRQ  180
PRVTHLFDVH SLEQQSEITP KQITCRTRGS PHPTSNHWKS QHPFHGRLTS NMVCKHCEHQ  240
SPVRFDTFDS LSLSIPAATW GHPLTLDHCL HHFISSESVR DVVCDNCTKI EAKGTLNGEK  300
VEHQRTTFVK QLKLGKLPQC LCIHLQRLSW SSHGTPLKRH EHVQFNEFLM MDIYKYHLLG  360
HKPSQHNPKL NKNPGPTLEL QDGPGAPTPV LNQPGAPKTQ IFMNGACSPS LLPTLSAPMP  420
FPLPVVPDYS SSTYLFRLMA VVVHHGDMHS GHFVTYRRSP PSARNPLSTS NQWLWVSDDT  480
VRKASLQEVL SSSAYLLFYE RVLSRMQHQS QECKSEE                          517

SEQ ID NO: 45          moltype = DNA  length = 2487
FEATURE                Location/Qualifiers
misc_feature           1..2487
                       note = Other DNA
source                 1..2487
                       mol_type = other DNA
                       organism = Homo sapiens
SEQUENCE: 45
atgacaggat caaattcaca cataacgata ttaaccttaa aggtgttacc tcattttgaa  60
```

```
agtcttggga aacaggaaaa aattcctaac aaaatgtcag cttttcgaaa tcattgtcca  120
catttggatt cagttggtga aataacaaaa gaagatttga tacaaaaatc ccttggtact  180
tgtcaggatt gtaaagtcca aggaccaaat ctttgggcat gtctggagaa tagatgttca  240
tatgttggct gtggtgaatc acaagtagat cacagcacca tacattctca ggagacaaag  300
cattatctaa ctgtgaacct taccactctt cgagtatggt gttatgcttg cagcaaagaa  360
gtatttttgg ataggaaatt aggaactcag ccttcattgc ctcatgtaag acaacctcac  420
caaatacaag aaaacagtgt ccaggatttt aaaataccca gtaatacaac attaaaaact  480
cctctggttg ccgtatttga tgatctggat atagaagcgg atgaagaaga tgaacttagg  540
gccagaggtc ttacaggttt gaaaaatatt ggaaatactt gttacatgaa tgcagctttg  600
caggctcttt ctaattgccc acctttgaca cagtttttc ttgattgtgg aggactagct  660
cgaacagata agaaacctgc catttgtaaa agttatctca aactaatgac agagctgtgg  720
cataaaagca ggccaggatc tgttgtgcct actactctgt ttcaaggaat taaaactgta  780
aatccaacat ttcgggggta ttctcagcag gatgctcaag aattccttcg atgtttaatg  840
gatttgcttc atgaagaatt gaaagagcaa gtcatggaag tagaagaaga tccgcaaacc  900
ataaccactg aggagacaat ggaagaagac aagagccagt cggatgtaga ttttcagtct  960
tgtgaatctt gtagcaacag tgatagagca gaaaatgaaa atggctctag atgcttttct  1020
gaagataata atgaaacaac aatgttaatt caggatgatg aaaacaattc agaaatgtca  1080
aaggattggc aaaaagagaa gatgtgcaat aagattaata aagtaaattc tgaaggcgaa  1140
tttgataaag atagagactc tatatctgaa acagtcgact taaacaacca ggaaactgtc  1200
aaagtgcaaa tacacagcag agcttcagaa tatatcactg atgtccattc gaatgacctg  1260
tctacaccac agatccttcc atcaaatgaa ggtgttaatc cacgtttatc ggcaagccct  1320
cctaaatcag gcaatttgtg gccaggattg gcaccaccac acaaaaaagc tcagtctgca  1380
tctccaaaga gaaaaaaaca gcacaagaaa tacagaagtg ttatttcaga catatttgat  1440
ggaacaatca ttagttcagt gcagtgtctg acttgtgaca gggtgtctgt aaccctcgag  1500
acctttcaag atctgtcctt gccaattcct ggcaaggaag accttgctaa gctgcattca  1560
tcaagtcatc caacttctat agtcaaagca ggatcatgtg gcgaagcata tgctccacaa  1620
gggtggatag cttttttcat ggaatatgtg aagagctggt tttggggtcc agtagtaacc  1680
ttgcaagatt gtcttgctgc cttctttgcc agagatgaac taaaaggtga caatatgtac  1740
agttgtgaaa aatgcaaaaa gttgagaaat ggagtgaagt tttgtaaagt acaaaacttt  1800
cctgagattt tgtgcatcca ccttaaaaga ttcagacatg aactaatgtt ttccaccaaa  1860
atcagtaccc atgtttcatt tccgctagaa ggcttggatc ttcagccatt tcttgctaag  1920
gatagtccag ctcaaattgt gacatatgat cttctgtcag tcatttgcca tcatggaact  1980
gcaagtagtg gacactatat agcctactgc cgaaacaatc taaataatct ctggtatgaa  2040
tttgatgatc agagtgtcac tgaagtttca gaatctactg tacaaaatgc agaagcttac  2100
gttctttttct ataggaagag cagcgaagag gcacaaaaag agaggagaag gatatcaaat  2160
ttattgaaca taatggaacc aagcctcctt cagttttata tttctcgaca gtggcttaat  2220
aaatttaaga cctttgccga acctggccct atttcaaata atgactttct ttgtattcat  2280
ggaggtgttc ctccaagaaa agctggttat attgaagacc tggttttgat gctgcctcag  2340
aacatttggg ataacctata tagcaggtat ggtggaggac cagctgtcaa ccatctgtac  2400
atttgtcata cttgccaaat tgaggcggag aaaattgaaa aaagaagaaa aactgaattg  2460
gaaattttta ttcgggtaaa aaagtga                                     2487
```

```
SEQ ID NO: 46          moltype = AA  length = 828
FEATURE                Location/Qualifiers
source                 1..828
                       mol_type = protein
                       organism = Homo sapiens
SEQUENCE: 46
MTGSNSHITI LTLKVLPHFE SLGKQEKIPN KMSAFRNHCP HLDSVGEITK EDLIQKSLGT  60
CQDCKVQGPN LWACLENRCS YVGCGESQVD HSTIHSQETK HYLTVNLTTL RVWCYACSKE  120
VFLDRKLGTQ PSLPHVRQPH QIQENSVQDF KIPSNTTLKT PLVAVFDDLD IEADEEDELR  180
ARGLTGLKNI GNTCYMNAAL QALSNCPPLT QFFLDCGGLA RTDKKPAICK SYLKLMTELW  240
HKSRPGSVVP TTLFQGIKTV NPTFRGYSQQ DAQEFLRCLM DLLHEELKEQ VMEVEEDPQT  300
ITTEETMEED KSQSDVDFQS CESCSNSDRA ENENGSRCFS EDNNETTMLI QDDENNSEMS  360
KDWQKEKMCN KINKVNSEGE FDKDRDSISE TVDLNNQETV KVQIHSRASE YITDVHSNDL  420
STPQILPSNE GVNPRLSASP PKSGNLWPGL APPHKKAQSA SPKRKKQHKK YRSVISDIFD  480
GTIISSVQCL TCDRVSVTLE TFQDLSLPIP GKEDLAKLHS SSHPTSIVKA GSCGEAYAPQ  540
GWIAFFMEYV KSWFWGPVVT LQDCLAAFFA RDELKGDNMY SCEKCKKLRN GVKFCKVQNF  600
PEILCIHLKR FRHELMFSTK ISTHVSFPLE GLDLQPFLAK DSPAQIVTYD LLSVICHHGT  660
ASSGHYIAYC RNNLNNLWYE FDDQSVTEVS ESTVQNAEAY VLFYRKSSEE AQKERRRISN  720
LLNIMEPSLL QFYISRQWLN KFKTFAEPGP ISNNDFLCIH GGVPPRKAGY IEDLVLMLPQ  780
NIWDNLYSRY GGGPAVNHLY ICHTCQIEAE KIEKRRKTEL EIFIRVKK               828
```

```
SEQ ID NO: 47          moltype = DNA  length = 10188
FEATURE                Location/Qualifiers
misc_feature           1..10188
                       note = Other DNA
source                 1..10188
                       mol_type = other DNA
                       organism = Homo sapiens
SEQUENCE: 47
atgagaagga aaaactctta ctatgtgtgg caaaaaattt ttcaaattca gtttccctta  60
tatactgctt acaagcataa tactcaccct actattgagg atatatcaac tcaagaaagt  120
aacatattag gggcattctg tgatatgaat gatgtagaag taccattgca tttgcttcgt  180
tatgtatgtt tgttttgtgg gaaaaatggc ctttctctca tgaaggattg ctttgaatat  240
ggaactcctg aaactttgcc atttcttata gcacatgcgt ttattacagt tgtgtctaat  300
attagaatat ggctacatat tcccgctgtc atgcagcaca ttataccttt taggacctat  360
gttattaggt atttatgcaa gctctcggat caggagttac gacagagtgc agctcgtaac  420
atggctgact taatgtggag cacagtcaaa gaaccattgg atacaacatt atgctttgat  480
```

-continued

```
aaagaaagcc tagatcttgc atttaagtac tttatgtcac ctactttgac tatgaggttg  540
gctggattga gtcagataac aaatcaactc cataccttca atgatgtgtg caataatgaa  600
tcattagtat cggacacaga aacgtccatt gcaaaagaac ttgcagactg gcttattagc  660
aacaatgtgg tggagcatat atttggacca aatttacata ttgagattat caaacagtgc  720
caagtgattt tgaatttttt ggcagcagaa gggcgactga gtactcaaca tattgactgt  780
atttgggctg cagcacagtt gaaacattgt agtcggtata tacatgactt atttccttca  840
ctcatcaaga atttggatcc cgtaccactt agacatctac ttaatctggt ctcagctctt  900
gagccaagtg ttcatactga acagacactg tacttggcat ccatgttaat taaagcactg  960
tggaataacg cactagcagc taaggctcag ttatctaaac agagttcttt tgcatcttta  1020
ttaaatacta atattcccat tggaaataag aaagaggaag aagagcttag aagaacagct  1080
ccatcacctt ggtcacctgc agctagtcct caaagcagtg ataatagcga tacacatcaa  1140
agtggaggta gtgacattga aatggatgag caacttatta atagaaccaa acatgtgcaa  1200
caacgacttt cagacacaga ggaatccatg cagggaagtt ctgacgaaac tgccaacagt  1260
ggtgaagatg gaagcagtgg tcctggtagc agtagtgggc atagtgatgg atctagcaat  1320
gaggttaatt ctagccacgc aagccagtca gctgggagcc ctggcagtga ggtacagtca  1380
gaagacattg cagatattga agccctcaaa gaggaagatg aagacgatga tcatggtcat  1440
aatcctccca aaagcagttg tggtacagat cttcggaata gaaagttaga gagtcaagca  1500
ggcatttgcc tgggggactc ccaaggcacg tcagaaagaa atgggacaag cagcggaaca  1560
ggaaaggacc tggtttttaa cactgaatca ttgccatcag tagataatcg aatgcgaatg  1620
ctggatgctt gttcacactc tgaagaccca gaacatgata tttcagggga aatgaatgct  1680
actcatatag cacaagggtc tcaggagtct tgtatcacac gaactgggga cttccttggg  1740
gagactattg ggaatgaatt atttaattgt cgacaattta ttggtccaca gcatcaccac  1800
caccaccacc accatcacca ccaccacgat gggcatatgg ttgatgatat gctaagtgca  1860
gatgatgtca gttgtagtag ctcccaggtt agtgcaaaat cagaaaaaaa tatggctgat  1920
tttgatggtg aagaatctgg atgtgaagag gagctagttc agattaattc acatgcggaa  1980
ctgacatctc acctccaaca acatcttccc aatttagctt ccatttacca tgaacatctt  2040
agtcaaggac ctgtagttca taaacatcaa ttcaacagta atgctgttac agacattaat  2100
ttggataatg tttgcaagaa aggaaatact ttgtttgtgg atatagtcca agatgaagat  2160
gcagttaatc tttctgaagg attaataaat gaagcagaga aacttctttg ttcgttagta  2220
tgttggttta cagatagaca aattcgaatg agattcattg aaggttgcct tgaaaacttg  2280
ggaaacaaca gatcagtagt aatttcactt cgtcttcttc caaaactatt tggtactttt  2340
cagcagtttg ggagcagtta cgatacacac tggataacaa tgtgggcaga aaaagaactg  2400
aacatgatga agcttttctt tgataatttg gtatactaca ttcaaactgt gagagaagga  2460
agacaaaaac atgcactgta cagccatagt gctgaagttc aagttcgtct tcaattcttg  2520
acttgtgtat tttcaactct gggatcacct gatcatttca ggttaagttt agagcaagtt  2580
gacatcttat ggcattgttt agtagaagat tctgaatgtt atgatgatgc actccattgg  2640
tttttaaatc aagttcgaag taaagatcaa catgctatgg gtatggaaac ctacaaacat  2700
cttttcctgg agaagatgcc ccagctaaaa cctgaaacaa ttagcatgac tggcttaaac  2760
ctgtttcagc atctctgtaa cttggctcga ttggctacca gtgcctatga tggttgttca  2820
aattctgagc tgtgtggtat ggaccaattt tggggcattg ctttaagagc acaatctggt  2880
gatgtcagtc gagcagctat ccagtatatt aactcctatt atattaatgg taaaacaggt  2940
ttggagaagg agcaagaatt tattagtaag tgcatggaga gtcttatgat agcttctagc  3000
agtcttgaac aggaatcaca ctcaagtctc atggttatag aaagaggact ccttatgctg  3060
aagacacatc tggaagcgtt taggagaagg tttgcatatc atctgagaca gtggcaaatt  3120
gaaggcactg gtattagtag tcatttgaaa gcactgagtg acaaacagtc tctgccgcta  3180
agggttgtat gccagccagc tggacttcct gacaagatga ctattgaaat gtatcctagt  3240
gaccaggtag cagatcttag ggctgaagta actcattggt atgaaaattt acagaaagaa  3300
caaataaatc aacaagctca gcttcaggag tttggtcaaa gcaaccgaaa aggagagttt  3360
cctggaggcc tcatgggacc tgtcaggatg atttcatctg gacacgagtt aacaacagat  3420
tatgatgaaa aagcacttca tgagcttggt tttaaggata tgcagatggt atttgtatct  3480
ttgggtgcac caaggagaga gcggaaaggg gaaggtgttc agctgccagc atcttgcctc  3540
ccaccccctc agaaggacaa cattccaatg cttttgcttt tacaagagcc tcatttaact  3600
actcttttg atttattaga gatgcttgca tcatttaaac caccctcagg aaaagtggca  3660
gtggatgata gtgagagctt acgatgtgaa gaacttcatc ttcatgcaga aaatctgtct  3720
aggcgggtct gggagctact gatgcttctt cctacatgtc ctaatatgtt gatggcattc  3780
cagaatatct cagatgagca gagtaatgat ggatttaatt ggaaagaact tctcaaaatt  3840
aagagcgccc acaagctatt gtatgctctg gaaattattg aagcactggg aaaacctaat  3900
agaagaataa ggagggagtc tacgggaagt tacagtgatc tttatccaga ttcagatgat  3960
tcaagtgagg atcaagtgga aaatagtaaa aattcctgga gttgcaagtt tgttgctgct  4020
ggagggcttc aacagttatt agaaattttt aattctggaa ttctagagcc taaagagcag  4080
gaatcatgga ctgtgtggca gctagactgt cttgcttgct tgctgaagtt aatatgccag  4140
tttgcagtag atccatccga tttggattta gcttatcatg atgtctttgc ctggtctggt  4200
atagcggaaa gccataggaa aagaacctgg cctggcaaat caaggaaggc tgctggtgat  4260
catgctaagg gtcttcatat accacgatta acagaggtat ttcttgttct tgtccaagga  4320
accagtttga ttcagcgact tatgtctgtt gcttatacgt atgataatct ggctcctaga  4380
gttttaaaag ctcagtctga tcacaggtct agacatgaag tttcacatta ttcaatgtgg  4440
ctcttggtga gttgggctca ttgctgttct ttagtgaaat ctagccttgc tgatagcgat  4500
catttacaag attggctaaa gaaattgact ctccttattc ctgagactgc agttcgtcat  4560
gaatcatgca gtggtctcta taagttatcc ctgtcagggc tggatggagg agactcaatc  4620
aatcgttctt ttctgctatt ggctgcctca acattattga aatttcttcc tgatgctcaa  4680
gcactcaaac ctattaggat agatgattat gaggaagaac caatattaaa accaggatgt  4740
aaagagtatt tttggttgtt atgcaaatta gttgacaaca tacatataaa ggacgctagt  4800
cagacaacgc tcctcgactt agatgccttg gcaagacatt tggctgactg tattcgaagt  4860
agggagatcc ttgatcatca ggatggtaat gtagaagatg atgggcttac aggactccta  4920
aggcttgcaa caagtgttgt taaacacaaa ccacccttta aattttcaag ggaaggacag  4980
gaatttttga gagatatctt caatctcctg tttttgttgc caagtctaaa ggaccgacaa  5040
cagccaaagt gcaaatcaca ttcttcaaga gctgccgctt acgatttgtt agtagagatg  5100
gtaaaggggt ctgttgagaa ctacaggcta atacacaact gggttatggc acaacacatg  5160
cagtcccatg caccttataa atgggattac tggcctcatg aagatgtccg tgctgaatgt  5220
```

-continued

```
agatttgttg gccttactaa ccttggagct acttgttact tagcttctac tattcagcaa  5280
ctttatatga tacctgaggc aagacaggct gtcttcactg ccaagtattc agaggatatg  5340
aagcacaaga ccactcttct ggagcttcag aaaatgttta catatttaat ggagagtgaa  5400
tgcaaagcat ataatcctag acctttctgt aaaacataca ccatggataa gcagcctctg  5460
aatactgggg aacagaaaga tatgacagag tttttttactg atctaattac caaaatcgaa  5520
gaaatgtctc ccgaactgaa aaataccgtc aaaagtttat ttggaggtgt aattacaaac  5580
aatgttgtat ccttggattg tgaacatgtt agtcaaactg ctgaagagtt ttatactgtg  5640
aggtgccaag tggctgatat gaagaacatt tatgaatctc ttgatgaagt tactataaaa  5700
gacactttgg aaggtgataa catgtatact tgttctcatt gtgggaagaa agtacgagct  5760
gaaaaaaggg catgttttaa gaaattgcct cgcattttga gtttcaatac tatgagatac  5820
acatttaata tggtcacgat gatgaaagag aaagtgaata cacacttttc cttcccatta  5880
cgtttggaca tgacgcccta tacagaagat ttcttatgg gaaagagtga gaggaaagaa  5940
ggttttaaag aagtcagtga tcattcaaaa gactcagaga gctatgaata tgacttgata  6000
ggagtgactg ttcacacagg aacggcagat ggtggacact attatagctt tatcagagat  6060
atagtaaatc cccatgctta taaaaacaat aaatggtatc tttttaatga tgctgaggta  6120
aaacctttttg attctgctca acttgcatct gaatgttttg gtggagagat gacgaccaag  6180
acctatgatt ctgttacaga taaatttatg gacttctctt ttgaaaagac acacagtgca  6240
tatatgctgt tttacaaacg catggaacca gaggaagaaa atggcagaga atacaaattt  6300
gatgtttcgt cagagttact agagtggatt tggcatgata acatgcagtt tcttcaagac  6360
aaaaacattt ttgaacatac atattttgga tttatgtggc aattgtgtag ttgtattccc  6420
agtacattac cagatcctaa agctgtgtcc ttaatgacag caaagttaag cacttccttt  6480
gtcctagaga catttattca ttctaaagaa aagcccacga tgcttcagtg gattgaactg  6540
ttgacgaaac agtttaataa tagtcaggca gcttgtgagt ggtttttaga tcgtatggct  6600
gatgacgact ggtggccaat gcagatacta attaagtgcc ctaatcaaat tgtgagacag  6660
atgtttcagc gtttgtgtat ccatgtgatt cagaggctga gacctgtgca tgctcatctc  6720
tatttgcagc caggaatgga agatgggtca gatgatatgg atacctcagt agaagatatt  6780
ggtggtcgtt catgtgtcac tcgctttgtg agaaccctgt tattaattat ggaacatggt  6840
gtaaaacctc acagtaaaca tcttacagag tattttgcct tcctttacga atttgcaaaa  6900
atgggtgaag aagagagcca atttttgctt tcattgcaag ctatatctac aatggtacat  6960
ttttacatgg gaacaaaagg acctgaaaat cctcaagttg aagtgttatc agaggaagaa  7020
ggggaagaag aagaggagga agaagatatc ctctctctgg cagaagaaaa atacaggcca  7080
gctgcccttg aaaagatgat agctttagtt gctcttttgg ttgaacagtc tcgatcagaa  7140
aggcatttga cattatcaca gactgacatg gcagcattaa caggaggaaa gggatttccc  7200
ttcttgtttc aacatattcg tgatggcatc aatataagac aaacttgtaa tctgattttc  7260
agcctgtgtc gatacaataa tcgacttgca gaacatattg tatctatgct tttcacatca  7320
atagcaaagt tgactcctga ggcagccaat cctttcttta agttgttgac tatgctaatg  7380
gagtttgctg gtggacctcc aggaatgcct ccctttgcat cttatattct gcagaggata  7440
tgggaggtga ttgaatacaa tccttctcag tgtctagatt ggttggcagt gcagacaccc  7500
cgaaataaac tggcacacag ctgggtctta cagaatatgg aaaactgggt cgagcggttt  7560
cttttggctc acaattatcc tagagtgagg acttctgcag cttatcttct ggtgtccctt  7620
ataccaagca attcattccg tcagatgttc cggtcaacaa ggtctttgca catcccaacc  7680
cgtgaccttc cactcagtcc agacacaaca gtagtcctac atcaggtcta caacgtgctc  7740
cttggtttgc tctcaagagc caaactttat gttgatgctg ctgttcatgg cactacaaag  7800
ctagtgccct attttagctt tatgacttac tgtttaattt ccaaaactga gaagctgatg  7860
ttttccacat atttcatgga tttgtggaac cttttccagc ctaaactttc tgagccagca  7920
atagctacaa atcacaataa acaggctttg ctttcatttt ggtacaatgt ctgtgctgac  7980
tgtccagaga atatccgcct tattgttcag aacccagtgg taaccaagaa cattgccttc  8040
aattacatcc ttgctgacca tgatgatcag gatgtggtgc tttttaaccg tgggatgctg  8100
ccagcgtact atggcattct gaggctctgc tgtgagcagt ctcctgcatt cacacgacaa  8160
ctggcttctc accagaacat ccagtgggcc tttaagaatc ttacaccaca tgccagccaa  8220
taccctggag cagtagaaga actgtttaac ctgatgcagc tgtttatagc tcagaggcca  8280
gatatgagag aagaagaatt agaagatatt aaacagttca agaaaacaac cataagttgt  8340
tacttacgtt gcttagatgg ccgctcctgc tggactactt taataagtgc cttcagaata  8400
ctattagaat ctgatgaaga cagacttctt gttgtattta atcgaggatt gattctaatg  8460
acagagtctt tcaacacttt gcacatgatg tatcacgaag ctacagcttg ccatgtgact  8520
ggagatttag tagaacttct gtcaatattt ctttcggttt tgaagtctac acgcccttat  8580
cttcagagaa aagatgtgaa acaagcatta atccagtggc aggagcgaat tgaatttgcc  8640
cataaactgt taactcttct taattcctat agtcctccag aacttagaaa tgcctgtata  8700
gatgtcctca aggaacttgt actttgagt ccccatgatt ttcttcatac tctggttccc  8760
tttctacaac acaaccattg tacttaccat cacagtaata taccaatgtc tcttggacct  8820
tatttccctt gtcgagaaaa tatcaagcta ataggaggga aaagcaatat tcggcctccg  8880
cgccctgaac tcaatatgtg cctcttgccc acaatggtgg aaaccagtaa gggcaaagat  8940
gacgtttatg atcgtatgct gctagactac ttctttttctt atcatcagtt catccatcta  9000
ttatgccgag ttgcaatcaa ctgtgaaaaa tttactgaaa cattagttaa gctgagtgtc  9060
ctagttgcct atgaaggttt gccacttcat cttgcactgt tccccaaact ttggactgag  9120
ctatgccaga ctcagtctgc tatgtcaaaa aactgcatca agcttttgtg tgaagatcct  9180
gttttcgcag aatatattaa atgtatccta atggatgaaa gaacttttttt aaacaacaac  9240
attgtctaca cgttcatgac acatttcctt ctaaaggttc aaagtcaagt gttttctgaa  9300
gcaaactgtg ccaatttgat cagcactctt attacaaact tgataagcca gtatcagaac  9360
ctacagtctg atttctccaa ccgagttgaa atttccaaag caagtgcttc tttaaatggg  9420
gacctgaggg cactcgcttt gctcctgtca gtacacactc ccaaacagtt aaacccagct  9480
ctaattccaa ctctgcaaga gcttttaagc aaatgcagga cttgtctgca acagagaaac  9540
tcactccaag agcaagaagc caaagaaaga aaaactaaag atgatgaagg agcaactccc  9600
attaaaaggc ggcgtgttag cagtgatgag gagcacactg tagacagctg catcagtgac  9660
atgaaaacag aaaccaggga ggtcctgacc ccaacgagca cttctgacaa tgagaccaga  9720
gactcctcaa ttattgatcc aggaactgag caagatcttc cttcccctga aaatagttct  9780
gttaaagaat accgaatgga agttccatct tcgttttcag aagacatgtc aaatatcagg  9840
tcacagcatg cagaagaaca gtccaacaat ggtagatatg acgattgtaa agaatttaaa  9900
gacctccact gttccaagga ttctaccta gctgaggaag aatctgagtt cccttctact  9960
```

```
tctatctctg cagttctgtc tgacttagct gacttgagaa gctgtgatgg ccaagctttg  10020
ccctcccagg accctgaggt tgctttatct ctcagttgtg gccattccag aggactcttt  10080
agtcatatgc agcaacatga cattttagat accctgtgta ggaccattga atctacaatc  10140
catgtcgtca caaggatatc tggcaaagga aaccaagctg cttcttga               10188

SEQ ID NO: 48          moltype = AA  length = 3395
FEATURE                Location/Qualifiers
source                 1..3395
                       mol_type = protein
                       organism = Homo sapiens
SEQUENCE: 48
MRRKNSYYVW QKIFQIQFPL YTAYKHNTHP TIEDISTQES NILGAFCDMN DVEVPLHLLR  60
YVCLFCGKNG LSLMKDCFEY GTPETLPFLI AHAFITVVSN IRIWLHIPAV MQHIIPFRTY  120
VIRYLCKLSD QELRQSAARN MADLMWSTVK EPLDTTLCFD KESLDLAFKY FMSPTLTMRL  180
AGLSQITNQL HTFNDVCNNE SLVSDTETSI AKELADWLIS NNVVEHIFGP NLHIEIIKQC  240
QVILNFLAAE GRLSTQHIDC IWAAAQLKHC SRYIHDLFPS LIKNLDPVPL RHLLNLVSAL  300
EPSVHTEQTL YLASMLIKAL WNNALAAKAQ LSKQSSFASL LNTNIPIGNK KEEEELRRTA  360
PSPWSPAASP QSSDNSDTHQ SGGSDIEMDE QLINRTKHVQ QRLSDTEESM QGSSDETANS  420
GEDGSSGPGS SSGHSDGSSN EVNSSHASQS AGSPGSEVQS EDIADIEALK EEDEDDDHGH  480
NPPKSSCGTD LRNRKLESQA GICLGDSQGT SERNGTSSGT GKDLVFNTES LPSVDNRMRM  540
LDACSHSEDP EHDISGEMNA THIAQGSQES CITRTGDFLG ETIGNELFNC RQFIGPQHHH  600
HHHHHHHHHD GHMVDDMLSA DDVSCSSSQV SAKSEKNMAD FDGEESGCEE ELVQINSHAE  660
LTSHLQQHLP NLASIYHEHL SQGPVVHKHQ FNSNAVTDIN LDNVCKKGNT LLWDIVQDED  720
AVNLSEGLIN EAEKLLCSLV CWFTDRQIRM RFIEGCLENL GNNRSVVISL RLLPKLFGTF  780
QQFGSSYDTH WITMWAEKEL NMMKLFFDNL VYYIQTVREG RQKHALYSHS AEVQVRLQFL  840
TCVFSTLGSP DHFRLSLEQV DILWHCLVED SECYDDALHW FLNQVRSKDQ HAMGMETYKH  900
LFLEKMPQLK PETISMTGLN LFQHLCNLAR LATSAYDGCS NSELCGMDQF WGIALRAQSG  960
DVSRAAIQYI NSYYINGKTG LEKEQEFISK CMESLMIASS SLEQESHSSL MVIERGLLML  1020
KTHLEAFRRR FAYHLRQWQI EGTGISSHLK ALSDKQSLPL RVVCQPAGLP DKMTIEMYPS  1080
DQVADLRAEV THWYENLQKE QINQQAQLQE FGQSNRKGEF PGGLMGPVRM ISSGHELTTD  1140
YDEKALHELG FKDMQMVFVS LGAPRRERKG EGVQLPASCL PPPQKDNIPM LLLLQEPHLT  1200
TLFDLLEMLA SFKPPSGKVA VDDSESLRCE ELHLHAENLS RRVWELLMLL PTCPNMLMAF  1260
QNISDEQSND GFNWKELLKI KSAHKLLYAL EIIEALGKPN RRIRRESTGS YSDLYPDSDD  1320
SSEDQVENSK NSWSCKFVAA GGLQQLLEIF NSGILEPKEQ ESWTVWQLDC LACLLKLICQ  1380
FAVDPSDLDL AYHDVFAWSG IAESHRKRTW PGKSRKAAGD HAKGLHIPRL TEVFLVLVQG  1440
TSLIQRLMSV AYTYDNLAPR VLKAQSDHRS RHEVSHYSMW LLVSWAHCCS LVKSSLADSD  1500
HLQDWLKKLT LLIPETAVRH ESCSGLYKLS LSGLDGGDSI NRSFLLLAAS TLLKFLPDAQ  1560
ALKPIRIDDY EEEPILKPGC KEYFWLLCKL VDNIHIKDAS QTTLLDLDAL ARHLADCIRS  1620
REILDHQDGN VEDDGLTGLL RLATSVVKHK PPFKFSREGQ EFLRDIFNLL FLLPSLKDRQ  1680
QPKCKSHSSR AAAYDLLVEM VKGSVENYRL IHNWVMAQHM QSHAPYKWDY WPHEDVRAEC  1740
RFVGLTNLGA TCYLASTIQQ LYMIPEARQA VFTAKYSEDM KHKTTLLELQ KMFTYLMESE  1800
CKAYNPRPFC KTYTMDKQPL NTGEQKDMTE FFTDLITKIE EMSPELKNTV KSLFGGVITN  1860
NVVSLDCEHV SQTAEEFYTV RCQVADMKNI YESLDEVTIK DTLEGDNMYT CSHCGKKVRA  1920
EKRACFKKLP RILSFNTMRY TFNMVTMMKE KVNTHFSFPL RLDMTPYTED FLMGKSERKE  1980
GFKEVSDHSK DSESYEYDLI GVTVHTGTAD GGHYYSFIRD IVNPHAYKNN KWYLFNDAEV  2040
KPFDSAQLAS ECFGGEMTTK TYDSVTDKFM DFSFEKTHSA YMLFYKRMEP EEENGREYKF  2100
DVSSELLEWI WHDNMQFLQD KNIFEHTYFG FMWQLCSCIP STLPDPKAVS LMTAKLSTSF  2160
VLETFIHSKE KPTMLQWIEL LTKQFNNSQA ACEWFLDRMA DDDWWPMQIL IKCPNQIVRQ  2220
MFQRLCIHVI QRLRPVHAHL YLQPGMEDGS DDMDTSVEDI GGRSCVTRFV RTLLLIMEHG  2280
VKPHSKHLTE YFAFLYEFAK MGEEESQFLL SLQAISTMVH FYMGTKGPEN PQVEVLSEEE  2340
GEEEEEEEDI LSLAEEKYRP AALEKMIALV ALLVEQSRSE RHLTLSQTDM AALTGGKGFP  2400
FLFQHIRDGI NIRQTCNLIF SLCRYNNRLA EHIVSMLFTS IAKLTPEAAN PFFKLLTMLM  2460
EFAGGPPGMP PFASYILQRI WEVIEYNPSQ CLDWLAVQTP RNKLAHSWVL QNMENWVERF  2520
LLAHNYPRVR TSAAYLLVSL IPSNSFRQMF RSTRSLHIPT RDLPLSPDTT VVLHQVYNVL  2580
LGLLSRAKLY VDAAVHGTTK LVPYFSFMTY CLISKTEKLM FSTYFMDLWN LFQPKLSEPA  2640
IATNHNKQAL LSFWYNVCAD CPENIRLIVQ NPVVTKNIAF NYILADHDDQ DVVLFNRGML  2700
PAYYGILRLC CEQSPAFTRQ LASHQNIQWA FKNLTPHASQ YPGAVEELFN LMQLFIAQRP  2760
DMREEELEDI KQFKKTTISC YLRCLDGRSC WTTLISAFRI LLESDEDRLL VVFNRGLILM  2820
TESFNTLHMM YHEATACHVT GDLVELLSIF LSVLKSTRPY LQRKDVKQAL IQWQERIEFA  2880
HKLLTLLNSY SPPELRNACI DVLKELVLLS PHDFLHTLVP FLQHNHCTYH HSNIPMSLGP  2940
YFPCRENIKL IGGKSNIRPP RPELNMCLLP TMVETSKGKD DVYDRMLLDY FFSYHQFIHL  3000
LCRVAINCEK FTETLVKLSV LVAYEGLPLH LALFPKLWTE LCQTQSAMSK NCIKLLCEDP  3060
VFAEYIKCIL MDERTFLNNN IVYTFMTHFL LKVQSQVFSE ANCANLISTL ITNLISQYQN  3120
LQSDFSNRVE ISKASASLNG DLRALALLLS VHTPKQLNPA LIPTLQELLS KCRTCLQQRN  3180
SLQEQEAKER KTKDDEGATP IKRRRVSSDE EHTVDSCISD MKTETREVLT PTSTSDNETR  3240
DSSIIDPGTE QDLPSPENSS VKEYRMEVPS SFSEDMSNIR SQHAEEQSNN GRYDDCKEFK  3300
DLHCSKDSTL AEEESEFPST SISAVLSDLA DLRSCDGQAL PSQDPEVALS LSCGHSRGLF  3360
SHMQQHDILD TLCRTIESTI HVVTRISGKG NQAAS                             3395

SEQ ID NO: 49          moltype = DNA  length = 3057
FEATURE                Location/Qualifiers
misc_feature           1..3057
                       note = Other DNA
source                 1..3057
                       mol_type = other DNA
                       organism = Homo sapiens
SEQUENCE: 49
atggacaaga tcttggaggc ggtggtgacg tcgtcatacc cggtcagcgt gaagcagggg  60
ctggttcggc gcgtgctgga ggcggcgcgg cagccgctgg agcgtgagca gtgcctggcg  120
```

```
ctgctggcgc tgggcgcgcg cctctacgtg ggcggcgcgg aggagctgcc gcgccgcgtg  180
ggctgccagc tgctgcacgt ggccggccgc caccaccccg acgtcttcgc cgagttcttc  240
agcgcgcgtc gcgtgctgcg cctgctgcag ggtggcgccg gcccccccggg cccccgcgcg  300
ctcgcctgcg tgcagctggg tctgcagctg ctgcccgagg ggcctgcggc cgacgaggtg  360
ttcgcgctgc tgcggcgcga ggtgctgcgc accgtgtgcg agcgcccggg ccccgcggcc  420
tgcgcgcagg tggcacggct gctggctcgc cacccgcgct gtgtgcccga cggaccccac  480
cgcctgctct tctgccagca gctggtgcgt tgcctcggcc gcttccgctg cccagccgaa  540
ggcgaggagg gcgccgtgga gttcctagag caggcccagc aggtgagcgg gctcctggcg  600
cagctgtggc gcgcacagcc cgccgccatc ctgccctgcc tcaaagagct gttcgcagtc  660
atctcctgcg cagaggagga gccaccatct agcgccctgg ccagcgtggt ccagcacctc  720
ccattggagc tcatggatgg tgttgtccgg aacctcagca atgatgacag tgtgacagac  780
tcgcagatgc tgactgccat tagcaggatg attgactggg tgtcctggcc cctggggaag  840
aatattgaca agtggatcat tgcactgctg aagggcctgg ctgctgttaa gaagttcagc  900
atcttgatcg aggtttcgct caccaaaatt gagaaggttt tctctaagct gctgtacccc  960
atcgtccggg gagctgcctt gtctgtgctc aagtacatgc tcctgacctt ccagcactcc  1020
cacgaagcct tccacctgct cctccctcac atcccccccca tggtggcctc tctggtcaag  1080
gaggactcga actcggggac cagctgcctg gagcagctgg cggagctggt ccactgcatg  1140
gtgttccggt tcccgggctt cccggatctg tatgagcctg tcatggaggc catcaaggac  1200
ctccatgttc ccaatgagga ccgcatcaag cagctgctgg ggcaggatgc ctggacttcg  1260
cagaagagcg agctggcggg tttctatccc cggctcatgg ccaagtcaga cacgggcaag  1320
attggtctca tcaacctggg caacacatgc tatgtcaaca gcatccttca ggccttattc  1380
atggcgtctg acttcagaca ttgtgtgctc cgcttgactg agaacaactc acagcccctg  1440
atgaccaagc tgcagtggct ctttggcttc ctagaacaca gccagcggcc tgccatttcc  1500
ccagagaact tcctctccgc atcctggacg ccctggttca gccctggcac ccagcaggac  1560
tgctcggagt atctgaagta cctgctggat cggctgcacg aagaggagaa aacgggcaca  1620
aggatctgcc agaaactcaa gcagtccagc tcgccctctc cgcccgagga gcccccggcc  1680
ccaagttcaa cctctgtgga aaaaatgttt ggaggcaaga tagtgactcg gatctgctgt  1740
ctctgctgcc tcaacgtctc ctcccgggag gaggccttca cggacctctc tctcgccttc  1800
cctcctcctg agcgctgtcg ccgccgccgc ctgggctctg tgatgcgccc cacagaagac  1860
atcacagccc gggagttgcc cccaccaacc agtgcacagg ggccaggcag ggtgggtcct  1920
cggaggcaaa ggaaacactg catcacagag gacacccccc ccaccagcct gtacatcgaa  1980
ggcctggact ccaaggaagc tggtgggcag agcagtcagg aggaaaggat agagagggag  2040
gaagaaggga aggaggagag aacggagaag gaagaagtgg gggaggagga ggaaagcacc  2100
agaggggaag gagagaggga gaaagaggag gaggtggaag aggaagaaga gaaggtggag  2160
aaggagacag aaaaggaggc tgagcaggaa aaggaagaag acagcctggg agcggggacc  2220
cacccggatg ctgccatccc ctccggggag cggacatgtg gctctgaggg ctcccgctcc  2280
gtcctggacc tggttaacta cttcctgtcc cccgagaagc tgacagcaga aaaccgctac  2340
tactgcgagt cgtgtgcctc cctgcaggat gccgagaagg tggtggagct gagccaaggg  2400
ccgtgctacc tcatcctcac actgctgcgc ttctctttcg acctgcgcac catgcggcgc  2460
cgcaagatcc tggatgacgt ctccatcccc ctgctgctcc gcctgccact ggctggtggc  2520
cgtggccagg cctatgacct ctgcagtgtg gtggtgcact ctggagtgtc ttcggagagt  2580
ggtcactact actgctatgc ccgtgagggc gctgcccgcc ctgccgcttc tctgggaact  2640
gccgataggc cagagcccga gaaccagtgg tacctgttca atgacactcg ggtgtccttc  2700
tcttccttcg aatctgtcag caacgtcacc tccttcttcc ctaaggacac agcctatgtg  2760
ctgttttacc ggcagcggcc cagggagggg cccgaggctg agttgggctc ttctagagtc  2820
cggacagagc ccaccctgca caaggacttg atggaagcca tttccaaaga caacatcctt  2880
tacctacagg agcaggagaa ggaggcccgg agcagggcgg cctacatctc tgcactcccc  2940
acatctccgc actgggggag gggctttgat gaagacaagg atgaggatga aggctctcca  3000
gggggctgca atcctgcagg tggcaatggt ggtgacttcc acagactggt cttctaa     3057
```

```
SEQ ID NO: 50          moltype = AA  length = 1018
FEATURE                Location/Qualifiers
source                 1..1018
                       mol_type = protein
                       organism = Homo sapiens
SEQUENCE: 50
MDKILEAVVT SSYPVSVKQG LVRRVLEAAR QPLEREQCLA LLALGARLYV GGAEELPRRV  60
GCQLLHVAGR HHPDVFAEFF SARRVLRLLQ GGAGPPGPRA LACVQLGLQL LPEGPAADEV  120
FALLRREVLR TVCERPGPAA CAQVARLLAR HPRCVPDGPH RLLFCQQLVR CLGRFRCPAE  180
GEEGAVEFLE QAQQVSGLLA QLWRAQPAAI LPCLKELFAV ISCAEEEPPS SALASVVQHL  240
PLELMDGVVR NLSNDDSVTD SQMLTAISRM IDWVSWPLGK NIDKWIIALL KGLAAVKKFS  300
ILIEVSLTKI EKVFSKLLYP IVRGAALSVL KYMLLTFQHS HEAFHLLLPH IPPMVASLVK  360
EDSNSGTSCL EQLAELVHCM VFRFPGFPDL YEPVMEAIKD LHVPNEDRIK QLLGQDAWTS  420
QKSELAGFYP RLMAKSDTGK IGLINLGNTC YVNSILQALF MASDFRHCVL RLTENNSQPL  480
MTKLQWLFGF LEHSQRPAIS PENFLSASWT PWFSPGTQQD CSEYLKYLLD RLHEEEKTGT  540
RICQKLKQSS SPSPPEEPPA PSSTSVEKMF GGKIVTRICC LCCLNVSSRE EAFTDLSLAF  600
PPPERCRRRR LGSVMRPTED ITARELPPPT SAQGPGRVGP RRQRKHCITE DTPPTSLYIE  660
GLDSKEAGGQ SSQEERIERE EEGKEERTEK EEVGEEEEST RGEGEREKEE EVEEEEEKVE  720
KETEKEAEQE KEEDSLGAGT HPDAAIPSGE RTCGSEGSRS VLDLVNYFLS PEKLTAENRY  780
YCESCASLQD AEKVVELSQG PCYLILTLLR FSFDLRTMRR RKILDDVSIP LLLRLPLAGG  840
RGQAYDLCSV VVHSGVSSES GHYYCYAREG AARPAASLGT ADRPEPENQW YLFNDTRVSF  900
SSFESVSNVT SFFPKDTAYV LFYRQRPREG PEAELGSSRV RTEPTLHKDL MEAISKDNIL  960
YLQEQEKEAR SRAAYISALP TSPHWGRGFD EDKDEDEGSP GGCNPAGGNG GDFHRLVF    1018

SEQ ID NO: 51          moltype = DNA  length = 3372
FEATURE                Location/Qualifiers
misc_feature           1..3372
                       note = Other DNA
source                 1..3372
```

mol_type = other DNA
organism = Homo sapiens
SEQUENCE: 51
```
atgccaatag tggataagtt gaaggaggcc ctgaaacccg gccgcaagga ctcggctgat  60
gatggagaac tggggaagct tcttgcctcc tctgccaaga aggtcctttt acagaaaatc  120
gagttcgagc cagccagcaa gagcttctcc taccagctgg aggccttaaa gagcaaatat  180
gtgttgctca accccaaaac agagggagct agtcgccaca agagtggaga tgacccaccg  240
gccaggagac agggcagtga gcacacgtat gagagctgtg gtgacggagt cccagccccg  300
cagaaagtgc ttttccccac ggagcgactg tctctgaggt gggagcgggt cttccgcgtg  360
ggcgcaggac tccacaacct tggcaacacc tgctttctca atgccaccat ccagtgcttg  420
acctacacac cacctctagc caactacctg ctctccaagg agcatgctcg cagctgccac  480
cagggaagct tctgcatgct gtgtgtcatg cagaaccaca ttgtccaggc cttcgccaac  540
agcggcaacg ccatcaagcc cgtctccttc atccgagacc tgaaaaagat cgcccgacac  600
ttccgctttg ggaaccagga ggacgcgcat gagttcctgc ggtacaccat cgacgccatg  660
cagaaagcct gcctgaatgg ctgtgccaag ttggatcgtc aaacgcaggc tactaccttg  720
gtccatcaaa tttttggagg gtatctcaga tcacgcgtga agtgctccgt gtgcaagagc  780
gtctcggaca cctacgaccc ctacttggac gtcgcgctgg agatccggca agctgcgaat  840
attgtgcgtg ctctggaact tttgtgaaa gcagatgtcc tgagtggaga gaatgcctac  900
atgtgtgcta aatgcaagaa gaaggttcca gccagcaagc gcttcaccat ccacagaaca  960
tccaacgtct taaccctttc cctcaagcgc tttgccaact tcagcggggg gaagatcacc  1020
aaggatgtag gctatccgga attcctcaac atacgtccgt atatgtccca gaataatggt  1080
gatcctgtca tgtatggact ctatgctgtc ctggtgcact cgggctacag ctgccatgcc  1140
gggcactatt actgctacgt gaaggcaagc aatggacagt ggtaccagat gaatgattcc  1200
ttggtccatt ccagcaacgt caaggtggtt ctgaaccagc aggcctacgt gctgttctat  1260
ctgcgaattc caggctctaa gaaaagtccc gagggcctca tctccaggac aggctcctcc  1320
tcccttcccg gccgcccgag tgtgattcca gatcactcca agaagaacat cggcaatggg  1380
attatttcct ccccactgac tggaaagcga caagactctg ggacgatgaa gaagccgcac  1440
accactgaag agattggtgt gcccatatcc aggaatggct ccaccctggg cctgaagtcc  1500
cagaacggct gcattcctcc aaagctgccc tcggggtccc cttcccccaa actctcccag  1560
acacccacac acatgccaac catcctagac gaccctggaa agaaggtgaa gaagccagct  1620
cctcccacagc acttttcccc cagaactgct cagggggctgc ctgggaccag caactcgaat  1680
agcagcagat ctgggagcca aaggcagggc tcctgggaca gcagggatgt tgtcctctct  1740
acctcaccta agctcctggc tacagccact gccaacgggc atgggctgaa ggggaacgac  1800
gagagcgctg gcctcgacag gaggggctcc agcagctcca gcccagagca ctcggccagc  1860
agcgactcca ccaaggcccc ccagaccccc aggagtggag cggcccatct ctgcgattct  1920
caggaaacga actgttccac cgctggccac tccaaaacgc cgccaagtgg agcagattct  1980
aagacggtga agctgaagtc ccctgtcctg agcaacacca ccactgagcc tgcaagcacc  2040
atgtctcctc caccagccaa aaaactggcc ctttctgcca agaaggccag caccctgtgg  2100
agggcgaccg gcaatgacct ccgtccacct ccccctcac catcctccga cctcacccac  2160
cccatgaaaa cctctcaccc cgtcgttgcc tccacttggc ccgtccatag agccagggct  2220
gtgtcacctg ctccccaatc atccagccgc ctgcaacccc ccttcagccc ccaccccaca  2280
ttgctgtcca gtaccccaa gcccccaggg acgtcagaac cacggagctg ctcctccatc  2340
tcgacggcgc tgcctcaggt caacgaggac cttgtgtctc ttccacacca gttgccagag  2400
gccagtgagc ccccccagag cccctctgag aagaggaaaa agacctttgt gggagagccg  2460
cagaggctgg gctcagagac gcgcctccca cagcacatca gggaggccac tgcggctccc  2520
cacgggaaga ggaagaggaa gaagaagaag cgcccggagg acacagctgc cagcgccctg  2580
caggaggggc agacacagag acagcctggg agccccatgt acaggaggga gggccaggca  2640
cagctgcccg ctgtcagacg gcaggaagat ggcacacagc cacaggtgaa tggccagcag  2700
gtgggatgtg ttacggacgg ccaccacgcg agcagcagga agcggaggag gaaaggagca  2760
gaaggtcttg gtgaagaagg cggcctgcac caggacccac ttcggcacag ctgctctccc  2820
atgggtgatg gtgatccaga ggccatggaa gagtctccaa ggaaaaagaa aaagaaaaaa  2880
agaaagcagg agacacagcg ggcagtagaa gaggatgggc atctcaaatg cccaaggagt  2940
gccaagcccc aagatgctgt tgtccccgag tccagcagct gcgcaccatc cgcgaatggc  3000
tggtgtcctg gggaccgcat ggggctgagc caggcccctc ctgtgtcttg gaatggagag  3060
cgggagtctg atgtggtcca ggaactgctc aaatactcat ctgataaagc ttacgggaga  3120
aaagttctga cctgggatgg caagatgtcg gcggtcagtc aggatgctat tgaagacagc  3180
agacaggccc ggactgagac cgtggttgat gactgggacg aagagtttga ccgagggaag  3240
gaaaagaaaa ttaaaaaatt taagagagag aagaggagaa acttcaacgc cttccagaaa  3300
cttcagactc gacggaactt ctggtctgtg actcacccag caaaggctgc cagcctcagc  3360
tatcgccgct ga                                                    3372
```

SEQ ID NO: 52 moltype = AA length = 1123
FEATURE Location/Qualifiers
source 1..1123
mol_type = protein
organism = Homo sapiens
SEQUENCE: 52
```
MPIVDKLKEA LKPGRKDSAD DGELGKLLAS SAKKVLLQKI EFEPASKSFS YQLEALKSKY  60
VLLNPKTEGA SRHKSGDDPP ARRQGSEHTY ESCGDGVPAP QKVLFPTERL SLRWERVFRV  120
GAGLHNLGNT CFLNATIQCL TYTPPLANYL LSKEHARSCH QGSFCMLCVM QNHIVQAFAN  180
SGNAIKPVSF IRDLKKIARH FRFGNQEDAH EFLRYTIDAM QKACLNGCAK LDRQTQATTL  240
VHQIFGGYLR SRVKCSVCKS VSDTYDPYLD VALEIRQAAN IVRALELFVK ADVLSGENAY  300
MCAKCKKKVP ASKRFTIHRT SNVLTLSLKR FANFSGGKIT KDVGYPEFLN IRPYMSQNNG  360
DPVMYGLYAV LVHSGYSCHA GHYYCYVKAS NGQWYQMNDS LVHSSNVKVV LNQQAYVLFY  420
LRIPGSKKSP EGLISRTGSS SLPGRPSVIP DHSKKNIGNG IISSPLTGKR QDSGTMKKPH  480
TTEEIGVPIS RNGSTLGLKS QNGCIPPKLP SGSPSPKLSQ TPTHMPTILD DPGKKVKKPA  540
PPQHFSPRTA QGLPGTSNSN SSRSGSQRQG SWDSRDVVLS TSPKLLATAT ANGHGLKGND  600
ESAGLDRRGS SSSPEHSAS SDSTKAPQTP RSGAAHLCDS QETNCSTAGH SKTPPSGADS  660
KTVKLKSPVL SNTTTEPAST MSPPPAKKLA LSAKKASTLW RATGNDLRPP PPSPSSDLTH  720
```

```
PMKTSHPVVA STWPVHRARA VSPAPQSSSR LQPPFSPHPT LLSSTPKPPG TSEPRSCSSI  780
STALPQVNED LVSLPHQLPE ASEPPQSPSE KRKKTFVGEP QRLGSETRLP QHIREATAAP  840
HGKRKRKKKK RPEDTAASAL QEGQTQRQPG SPMYRREGQA QLPAVRRQED GTQPQVNGQQ  900
VGCVTDGHHA SSRKRRRKGA EGLGEEGGLH QDPLRHSCSP MGDGDPEAME ESPRKKKKKK  960
RKQETQRAVE EDGHLKCPRS AKPQDAVVPE SSSCAPSANG WCPGDRMGLS QAPPVSWNGE  1020
RESDVVQELL KYSSDKAYGR KVLTWDGKMS AVSQDAIEDS RQARTETVVD DWDEEFDRGK  1080
EKKIKKFKRE KRRNFNAFQK LQTRRNFWSV THPAKAASLS YRR                   1123

SEQ ID NO: 53          moltype = DNA  length = 2940
FEATURE                Location/Qualifiers
misc_feature           1..2940
                       note = Other DNA
source                 1..2940
                       mol_type = other DNA
                       organism = Homo sapiens
SEQUENCE: 53
atgtctcctc tgaagataca tggtcctatc agaattcgaa gtatgcagac tgggattaca  60
aagtggaaag aaggatcctt tgaaattgta gaaaaagaga ataaagtcag cctagtagtt  120
cactacaata ctggaggaat tccaaggata tttcagctaa gtcataacat taaaaatgtg  180
gtgcttcgac ccagtggagc gaaacaaagc cgcctaatgt taactctgca agataacagc  240
ttcttgtcta ttgacaaagt accaagtaag gatgcagagg aaatgaggtt gtttctagat  300
gcagtccatc aaaacagact tcctgcagcc atgaaaccgt ctcaggggtc tggtagtttt  360
ggagccattc tgggcagcag gacctcacag aaggaaacca gcaggcagct ttcttactca  420
gacaatcagg cttctgcaaa aagaggaagt ttggaaacta aagatgatat tccatttcga  480
aaagttcttg gtaatccggg tagaggatcg attaagactg tagcaggaag tggaatagct  540
cggacgattc cttctttgac atctacttca acacctctta gatcagggtt gctagaaaat  600
cgtactgaaa agaggaaaag aatgatatca actggctcag aattgaatga agattaccct  660
aaggaaaatg attcatcatc gaacaacaag gccatgacag atccctccag aaagtattta  720
accagcagta gagaaaagca gctgagtttg aaacagtcag aagagaatag gacatcaggg  780
cttttacctt tacagtcatc atccttttat ggtagcagag ctggatccaa ggaacactct  840
tctggtggca ctaacttaga caggactaat gtttcaagcc agactccctc tgccaaaaga  900
agtttgggat ttcttcctca gccagttcct ctttctgtta aaaaactgag gtgtaaccag  960
gattacactg gctggaataa accaagagtg cccctttcct ctcaccaaca gcagcaactg  1020
cagggcttct ccaatttggg aaatacctgc tatatgaatg ctattctaca atctctattt  1080
tcactccagt catttgcaaa tgacttgctt aaacaaggta tcccatggaa gaaaattcca  1140
ctcaatgcac ttatcagacg ctttgcacac ttgcttgtta aaaaagatat ctgtaattca  1200
gagaccaaaa aggatttact caagaaggtt aaaaatgcca tttcagctac agcagagaga  1260
ttctctggtt atatgcagaa tgatgctcat gaattttttaa gtcagtgttt ggaccagctg  1320
aaagaagata tggaaaaatt aaataaaact tggaagactg aacctgtttc tggagaagaa  1380
aattcaccag atatttcagc taccagagca tacacttgcc ctgttattac taatttggag  1440
tttgaggttc agcactccat catttgtaaa gcatgtggag agattatccc caaaagagaa  1500
cagtttaatg acctctctat tgaccttcct cgtaggaaaa aaccactccc tcctcgttca  1560
attcaagatt ctcttgatct tttctttagg gccgaagaac tggagtattc ttgtgagaag  1620
tgtggtggga agtgtgctct tgtcaggcac aaatttaaca ggcttcctag ggtcctcatt  1680
ctccatttga aacgatatag cttcaatgtg gctctctcgc ttaacaataa gattgggcag  1740
caagtcatca ttccaagata cctgaccctg tcatctcatt gcactgaaaa tacaaaacca  1800
ccttttaccc ttggttggag tgcacatatg gcaatttcta gaccattgaa agcctctcaa  1860
atggtgaatt cctgcatcac cagcccttct acaccttcaa agaaattcac cttcaaatcc  1920
aagagctcct tggctttatg ccttgattca gacagtgagg atgagctaaa acgttctgtg  1980
gccctcagcc agagactttg tgaaatgtta ggcaacgaac agcagcagga agacctggaa  2040
aaagattcaa aattatgccc aatagagcct gacaagtctg aattggaaaa ctcaggattt  2100
gacagaatga gcgaagaaga gcttctagca gctgtcttgg agataagtaa gagagatgct  2160
tcaccatctc tgagtcatga agatgatgat aagccaacta gcagcccaga taccggattt  2220
gcagaagatg atattcaaga aatgccagaa aatccagaca ctatggaaac tgagaagccc  2280
aaaacaatca cagagctgga tcctgccagt tttactgaga taactaaaga ctgtgatgag  2340
aataaagaaa acaaaactcc agaaggatct cagggagaag ttgattggct ccagcagtat  2400
gatatggagc gtgaaaggga agagcaagag cttcagcagg cactggctca gagccttcaa  2460
gagcaagagg cttgggaaca gaaagaagat gatgacctca aaagagctac cgagttaagt  2520
cttcaagagt ttaacaactc ctttgtggat gcattgggtt ctgatgagga ctctggaaat  2580
gaggatgttt ttgatatgga gtacacagaa gctgaagctg aggaactgaa aagaaatgct  2640
gagacaggaa atctgcctca ttcgtaccgg ctcatcagtg ttgtcagtca cattggtagc  2700
acttcttctt caggtcatta cattagtgat gtatatgaca ttaagaagca agcgtggttt  2760
acttacaatg acctggaggt atcaaaaatc caagaggctg ccgtgcagag tgatcgagat  2820
cggagtggct acatcttctt ttatatgcac aaggagatct ttgatgagct gctggaaaca  2880
gaaaagaact ctcagtcact tagcacggaa gtggggaaga ctacccgtca ggccttgtga  2940

SEQ ID NO: 54          moltype = AA  length = 978
FEATURE                Location/Qualifiers
source                 1..978
                       mol_type = protein
                       organism = Homo sapiens
SEQUENCE: 54
MSPLKIHGPI RIRSMQTGIT KWKEGSFEIV EKENKVSLVV HYNTGGIPRI FQLSHNIKNV  60
VLRPSGAKQS RLMLTLQDNS FLSIDKVPSK DAEEMRLFLD AVHQNRLPAA MKPSQGSGSF  120
GAILGSRTSQ KETSRQLSYS DNQASAKRGS LETKDDIPFR KVLGNPGRGS IKTVAGSGIA  180
RTIPSLTSTS TPLRSGLLEN RTEKRKRMIS TGSELNEDYP KENDSSSNNK AMTDPSRKYL  240
TSSREKQLSL KQSEENRTSG LLPLQSSSFY GSRAGSKEHS SGGTNLDRTN VSSQTPSAKR  300
SLGFLPQPVP LSVKKLRCNQ DYTGWNKPRV PLSSHQQQQL QGFSNLGNTC YMNAILQSLF  360
SLQSFANDLL KQGIPWKKIP LNALIRRFAH LLVKKDICNS ETKKDLLKKV KNAISATAER  420
```

-continued

```
FSGYMQNDAH EFLSQCLDQL KEDMEKLNKT WKTEPVSGEE NSPDISATRA YTCPVITNLE  480
FEVQHSIICK ACGEIIPKRE QFNDLSIDLP RRKKPLPPRS IQDSLDLFFR AEELEYSCEK  540
CGGKCALVRH KFNRLPRVLI LHLKRYSFNV ALSLNNKIGQ QVIIPRYLTL SSHCTENTKP  600
PFTLGWSAHM AISRPLKASQ MVNSCITSPS TPSKKFTFKS KSSLALCLDS DSEDELKRSV  660
ALSQRLCEML GNEQQQEDLE KDSKLCPIEP DKSELENSGF DRMSEEELLA AVLEISKRDA  720
SPSLSHEDDD KPTSSPDTGF AEDDIQEMPE NPDTMETEKP KTITELDPAS FTEITKDCDE  780
NKENKTPEGS QGEVDWLQQY DMEREREEQE LQQALAQSLQ EQEAWEQKED DDLKRATELS  840
LQEFNNSFVD ALGSDEDSGN EDVFDMEYTE AEAEELKRNA ETGNLPHSYR LISVVSHIGS  900
TSSSGHYISD VYDIKKQAWF TYNDLEVSKI QEAAVQSDRD RSGYIFFYMH KEIFDELLET  960
EKNSQSLSTE VGKTTRQA                                                978

SEQ ID NO: 55          moltype = DNA  length = 3015
FEATURE                Location/Qualifiers
misc_feature           1..3015
                       note = Other DNA
source                 1..3015
                       mol_type = other DNA
                       organism = Homo sapiens
SEQUENCE: 55
atggacaaga tcctggaggg ccttgtgagt tcctcgcatc ccctgcccct caagcgggtg  60
attgtgcgga aggtggtgga atcggcggag cactggctag acgaggcgca gtgcgaggcc  120
atgtttgacc tgacgacccg gctcatcctg gagggccagg accctttcca gcggcaggtg  180
gggcaccagg tgctggaggc ctacgcacga taccaccggc cagagttcga gtccttcttc  240
aacaagacct tcgtgttggg cctccttcat cagggctacc actctctgga caggaaggat  300
gtagccatcc tggactacat tcacaacggc ctgaagctga ttatgagctg tccgtcggtg  360
ctggatctct ttagcctcct gcaggtagag gtgttacgga tggtgtgtga gaggccggag  420
ccgcagctct gtgcccgact gagcgacctt ctgaccgact ttgtgcaatg catccccaag  480
gggaaattgt ccatcacgtt ctgtcaacag ctggttcgaa cgataggcca tttccagtgc  540
gtgtccaccc aggaaagaga gctgcgggaa tatgtctccc aggtgacaaa agtgagtaac  600
ttgctgcaga acatctggaa ggccgagcct gccacactac tgccttccct gcaagaagtt  660
tttgcaagca tctcttccac agatgcatca tttgaacctt ctgtagcatt ggcaagcctt  720
gtgcagcata ttcctcttca gatgattaca gttctcatca ggagccttac tacggatcca  780
aatgtaaaag atgcaagtat gacccaagcc ctttgcagaa tgattgactg gctatcctgg  840
ccattggctc agcatgtgga tacatgggta attgcactcc tgaaaggact ggcagctgtc  900
cagaagttta ctattttgat agatgttact ttgctgaaaa tagaactggt ttttaatcga  960
ctttggtttc ctcttgtgag acctggtgct cttgcagttc tttctcacat gctgcttagc  1020
tttcagcatt ctccagaggc gttccatttg attgttcctc atgtggttaa tttggttcat  1080
tctttcaaaa atgatggtct gccttcaagt acagccttct tagtacaatt aacagaattg  1140
atacactgta tgatgtatca ttattctgga tttccagatc tctatgaacc tattctggag  1200
gcaataaagg attttcctaa gcccagtgaa gagaagatta agttaattct caatcaaagt  1260
gcctggactt ctcaatccaa ttctttggcg tcttgcttgt ctagactttc tggaaaatct  1320
gaaactggga aaactggtct tattaaccta ggaaatacat gttatatgaa cagtgttata  1380
caagccttgt ttatggccac agatttcagg agacaagtat tatctttaaa tctaaatggg  1440
tgcaattcat taatgaaaaa attacagcat ctttttgcct ttctggccca tacacagagg  1500
gaagcatacg cacctcggat attctttgag gcttccagac ctccatggtt tactcccaga  1560
tcacagcaag actgttctga atacctcaga tttctccttg acaggctcca tgaagaagaa  1620
aagatcttga aagttcaggc ctcacacaag ccttctgaaa ttctggaatg cagtgaaact  1680
tctttacagg aagtagctag taaagcagca gtactaacag agacccctcg tacaagtgac  1740
ggtgagaaga ctttaataga aaaaatgttt ggaggaaaac tacgaactca catacgttgt  1800
ttgaactgca ggagtacctc acaaaaagtg gaagccttta cagatctttc gcttgccttt  1860
tgtccttcct cttctttgga aaacatgtct gtccaagatc cagcatcatc acccagtata  1920
caagatggtg gtctaatgca agcctctgta cccggtcctt cagaagaacc agtagtttat  1980
aatccaacaa cagctgcctt catctgtgac tcacttgtga atgaaaaaac cataggcagt  2040
cctcctaatg agttttactg ttctgaaaac acttctgtcc ctaacgaatc taacaagatt  2100
cttgttaata aagatgtacc tcagaaacca ggaggtgaaa ccacaccttc agtaactgac  2160
ttactaaatt atttttggc tccagagatt cttactggtg ataaccaata ttattgtgaa  2220
aactgtgcct ctctgcaaaa tgctgagaaa actatgcaaa tcacggagga acctgaatac  2280
cttattctta ctctcctgag attttcatat gatcagaagt atcatgtgag aaggaaaatt  2340
ttagacaatg tatcactgcc actggttttg gagttgccag ttaaaagaat tacttctttc  2400
tcttcattgt cagaaagttg gtctgtagat gttgacttca ctgatcttag tgagaacctt  2460
gctaaaaaat taaagccttc agggactgat gaagcttcct gcacaaaatt ggtgccctat  2520
ctattaagtt ccgttgtggt tcactctggt atatcctctg aaagtgggca ttactattct  2580
tatgccagaa atatcacaag tacagactct tcatatcaga tgtaccacca gtctgaggct  2640
ctggcattag catcctccca gagtcattta ctagggagag atagtcccag tgcagttttt  2700
gaacaggatt tggaaaataa ggaaatgtca aaagaatggt tttatttaa tgacagtaga  2760
gtgacattta cttcatttca gtcagtccag aaaattacga gcaggtttcc aaaggacaca  2820
gcttatgtgc ttttgtataa aaaacagcat agtactaatg gtttaagtgg taataaccca  2880
accagtggac tctggataaa tggagaccca cctctacaga aagaacttat ggatgctata  2940
acaaaagaca ataaactata tttacaggta agttggaaat acaagcttta tttgttgaaa  3000
atattaaaca attga                                                   3015

SEQ ID NO: 56          moltype = AA  length = 1004
FEATURE                Location/Qualifiers
source                 1..1004
                       mol_type = protein
                       organism = Homo sapiens
SEQUENCE: 56
MDKILEGLVS SSHPLPLKRV IVRKVVESAE HWLDEAQCEA MFDLTTRLIL EGQDPFQRQV  60
GHQVLEAYAR YHRPEFESFF NKTFVLGLLH QGYHSLDRKD VAILDYIHNG LKLIMSCPSV  120
```

```
LDLFSLLQVE VLRMVCERPE PQLCARLSDL LTDFVQCIPK GKLSITFCQQ LVRTIGHFQC  180
VSTQERELRE YVSQVTKVSN LLQNIWKAEP ATLLPSLQEV FASISSTDAS FEPSVALASL  240
VQHIPLQMIT VLIRSLTTDP NVKDASMTQA LCRMIDWLSW PLAQHVDTWV IALLKGLAAV  300
QKFTILIDVT LLKIELVFNR LWFPLVRPGA LAVLSHMLLS FQHSPEAFHL IVPHVVNLVH  360
SFKNDGLPSS TAFLVQLTEL IHCMMYHYSG FPDLYEPILE AIKDFPKPSE EKIKLILNQS  420
AWTSQSNSLA SCLSRLSGKS ETGKTGLINL GNTCYMNSVI QALFMATDFR RQVLSLNLNG  480
CNSLMKKLQH LFAFLAHTQR EAYAPRIFFE ASRPPWFTPR SQQDCSEYLR FLLDRLHEEE  540
KILKVQASHK PSEILECSET SLQEVASKAA VLTETPRTSD GEKTLIEKMF GGKLRTHIRC  600
LNCRSTSQKV EAFTDLSLAF CPSSSLENMS VQDPASSPSI QDGGLMQASV PGPSEEPVVY  660
NPTTAAFICD SLVNEKTIGS PPNEFYCSEN TSVPNESNKI LVNKDVPQKP GGETTPSVTD  720
LLNYFLAPEI LTGDNQYYCE NCASLQNAEK TMQITEEPEY LILTLLRFSY DQKYHVRRKI  780
LDNVSLPLVL ELPVKRITSF SSLSESWSVD VDFTDLSENL AKKLKPSGTD EASCTKLVPY  840
LLSSVVVHSG ISSESGHYYS YARNITSTDS SYQMYHQSEA LALASSQSHL LGRDSPSAVF  900
EQDLENKEMS KEWFLFNDSR VTFTSFQSVQ KITSRFPKDT AYVLLYKKQH STNGLSGNNP  960
TSGLWINGDP PLQKELMDAI TKDNKLYLQV SWKYKLYLLK ILNN                  1004

SEQ ID NO: 57          moltype = DNA  length = 1698
FEATURE                Location/Qualifiers
misc_feature           1..1698
                       note = Other DNA
source                 1..1698
                       mol_type = other DNA
                       organism = Homo sapiens
SEQUENCE: 57
atgtccggcc ggtctaagcg ggagtctcgc ggttccactc gcgggaagcg agagtctgag  60
tcgcggggca gctccggtcg cgtcaagcgg gagcgagatc gggagcggga gcctgaggcg  120
gcgagctccc ggggcagccc tgtgcgcgtg aagcgggagt tcgagccggc gagcgcgcgc  180
gaggccccgg cttctgttgt cccgtttgtg cgggtgaagc gggagcgcga ggtcgatgag  240
gactcggagc ctgagcggga ggtgcgagca aagaatggcc gagtggattc tgaggaccgg  300
aggagccgcc actgcccgta cctggacacc attaacagga gtgtgctgga ctttgacttt  360
gagaaactgt gttctatctc cctctcacac atcaatgctt atgcctgtct ggtgtgtggc  420
aagtactttc aaggccgggg tttgaagtct cacgcctaca ttcacagtgt ccagtttagc  480
caccatgttt tcctcaacct ccacaccctc aagttttact gccttccaga caactatgag  540
atcatcgatt cctcattgga ggatatcacg tatgtgttga agcccacttt cacaaagcag  600
caaattgcaa acttggacaa gcaagccaaa ttgtcccggg catatgatgg taccacttac  660
ctgccgggta ttgtgggact gaataacata aaggccaatg attatgccaa cgctgtcctt  720
caggctctat ctaatgttcc tcctctccgg aactactttc tggaagaaga caattataag  780
aacatcaaac gtcctccagg ggatatcatg ttcttgttgg tccagcgttt tggagagctg  840
atgagaaagc tctggaaccc tcgaaatttc aaggcacatg tgtctcccca tgagatgctt  900
caggcagttg tactttgcag taagaagact tttcagatca ccaaacaagg agatggcgtt  960
gactttctgt cttggtttct gaatgctctg cactcagctc tgggggggcac aaagaagaaa  1020
aagaagacta ttgtgactga tgttttccag gggtccatga ggatcttcac taaaaagctt  1080
ccccatcctg atctgccagc agaagaaaaa gagcagttgc tccataatga cgagtaccag  1140
gagacaatgg tggagtccac ttttatgtac ctgacgctgg accttcctac tgcccccctc  1200
tacaaggacg agaaggagca gctcatcatt ccccaagtgc cactcttcaa catcctggct  1260
aagttcaatg gcatcactga gaaggaatat aagacttaca aggagaactt tctgaagcgc  1320
ttccagctta ccaagttgcc tccatatcta atcttttgta tcaagagatt cactaagaac  1380
aacttctttg ttgagaagaa tccaactatt gtcaatttcc ctattacaaa tgtggatctg  1440
agagaatact tgtctgaaga agtacaagca gtacacaaga ataccaccta tgacctcatt  1500
gccaacatcg tgcatgacgg caagccctcc gagggctcct accggatcca cgtgcttcat  1560
catgggacag gcaaatggta tgaattacaa gacctccagg tgactgacat ccttccccag  1620
atgatcacac tgtcagaggc ttacattcag atttggaaga ggcgagataa tgatgaaacc  1680
aaccagcagg ggcttga                                                1698

SEQ ID NO: 58          moltype = AA  length = 565
FEATURE                Location/Qualifiers
source                 1..565
                       mol_type = protein
                       organism = Homo sapiens
SEQUENCE: 58
MSGRSKRESR GSTRGKRESE SRGSSGRVKR ERDREREPEA ASSRGSPVRV KREFEPASAR  60
EAPASVVPFV RVKREREVDE DSEPEREVRA KNGRVDSEDR RSRHCPYLDT INRSVLDFDF  120
EKLCSISLSH INAYACLVCG KYFQGRGLKS HAYIHSVQFS HHVFLNLHTL KFYCLPDNYE  180
IIDSSLEDIT YVLKPTFTKQ QIANLDKQAK LSRAYDGTTY LPGIVGLNNI KANDYANAVL  240
QALSNVPPLR NYFLEEDNYK NIKRPPGDIM FLLVQRFGEL MRKLWNPRNF KAHVSPHEML  300
QAVVLCSKKT FQITKQGDGV DFLSWFLNAL HSALGGTKKK KTIVTDVFQ GSMRIFTKKL  360
PHPDLPAEEK EQLLHNDEYQ ETMVESTFMY LTLDLPTAPL YKDEKEQLII PQVPLFNILA  420
KFNGITEKEY KTYKENFLKR FQLTKLPPYL IFCIKRFTKN NFFVEKNPTI VNFPITNVDL  480
REYLSEEVQA VHKNTTYDLI ANIVHDGKPS EGSYRIHVLH HGTGKWYELQ DLQVTDILPQ  540
MITLSEAYIQ IWKRRDNDET NQQGA                                       565

SEQ ID NO: 59          moltype = DNA  length = 2139
FEATURE                Location/Qualifiers
misc_feature           1..2139
                       note = Other DNA
source                 1..2139
                       mol_type = other DNA
                       organism = Homo sapiens
SEQUENCE: 59
```

```
atgctagcaa tggatacgtg caaacatgtt gggcagctgc agcttgctca agaccattcc  60
agcctcaacc ctcagaaatg gcactgtgtg gactgcaaca cgaccgagtc catttgggct  120
tgccttagct gctcccatgt tgcctgtgga agatatattg aagagcatgc actcaagcac  180
tttcaagaaa gcagtcatcc tgttgcattg gaggtgaatg agatgtacgt tttttgttac  240
ctttgtgatg attatgttct gaatgataac gcaactggag acctgaagtt actacgacgt  300
acattaagtg ccatcaaaag tcaaaattat cactgcacaa ctcgtagtgg gaggttttta  360
cggtccatgg gtacaggtga tgattcttat ttcttacatg acggtgccca atctctgctt  420
caaagtgaag atcaactgta tactgctctt tggcacagga gaaggatact aatgggtaaa  480
atctttcgaa catggtttga acaatcaccc attggaagaa aaaagcaaga agaaccattt  540
caggaaaaaa tagtagtaaa aagagaagta aagaaaagac ggcaggaatt ggagtatcaa  600
gttaaagcag aattggaaag tatgcctcca agaaagagtt tacgtttaca agggctcgct  660
cagtcgacca taatagaaat agtttctgtt caggtgccag cacaaacgcc agcatcacca  720
gcaaaagata aagtactctc tacctcagaa aatgaaatat ctcaaaaagt cagtgactcc  780
tcagttaaac gaaggccaat agtaactcct ggtgtaacag gattgagaaa tttgggaaat  840
acttgctata tgaattctgt tcttcaggtg ttgagtcatt tacttatttt tcgacaatgt  900
tttttaaagc ttgatctgaa ccaatggctg gctatgactg ctagcgagaa gacaagatct  960
tgtaagcatc caccagtcac agatacagta gtatatcaaa tgaatgaatg tcaggaaaaa  1020
gatacaggtt ttgtttgctc cagacaatca agtctgtcat caggactaag tggtggagca  1080
tcaaaaggta gaaagatgga acttattcag ccaaaggagc caacttcaca gtacatttct  1140
ctttgtcatg aattgcatac tttgttccaa gtcatgtggt ctggaaagtg ggcgttggtc  1200
tcaccatttg ctatgctaca ctcagtgtgg agactcattc ctgcctttcg tggttacgcc  1260
caacaagacg ctcaggaatt tctttgtgaa cttttagata aaatacaacg tgaattagag  1320
acaactggta ccagtttacc agctcttatc cccacttctc aaaggaaact catcaaacaa  1380
gttctgaatg ttgtaaataa cattttttcat ggacaacttc ttagtcaggt tacatgtctt  1440
gcatgtgaca acaaatcaaa taccatagaa cctttctggg acttgtcatt ggagtttcca  1500
gaaaggtatc aatgcagtgg aaaagatatt gcttcccagc catgtctggt tactgaaatg  1560
ttggccaaat ttacagaaac tgaagcttta gaaggaaaaa tctacgtatg tgaccagtgt  1620
aactcaaagc gtagaaggtt ttcctccaaa ccagttgtac tcacagaagc ccagaaacaa  1680
cttatgatat gccacctacc tcaggttctc agactgcacc tcaaacgatt caggtggtca  1740
ggacgtaata accgagagaa gattggtgtt catgttggct ttgaggaaat cttaaacatg  1800
gagccctatt gctgcaggga gaccctgaaa tccctcagac cagaatgctt tatctatgac  1860
ttgtccgcgg tggtgatgca ccatgggaaa ggatttggct cagggcacta cactgcctac  1920
tgctataatt ctgaaggagg gttctgggta cactgcaatg attccaaact aagcatgtgc  1980
actatggatg aagtatgcaa ggctcaagct tatatcttgt tttataccca acgagttact  2040
gagaatggac attctaaact tttgcctcca gagctcctgt tggggagcca acatcccaat  2100
gaagacgctg atacctcgtc taatgaaatc cttagctga                        2139

SEQ ID NO: 60          moltype = AA  length = 712
FEATURE                Location/Qualifiers
source                 1..712
                       mol_type = protein
                       organism = Homo sapiens
SEQUENCE: 60
MLAMDTCKHV GQLQLAQDHS SLNPQKWHCV DCNTTESIWA CLSCSHVACG RYIEEHALKH  60
FQESSHPVAL EVNEMYVFCY LCDDYVLNDN ATGDLKLLRR TLSAIKSQNY HCTTRSGRFL  120
RSMGTGDDSY FLHDGAQSLL QSEDQLYTAL WHRRRILMGK IFRTWFEQSP IGRKKQEEPF  180
QEKIVVKREV KKRRQELEYQ VKAELESMPP RKSLRLQGLA QSTIIEIVSV QVPAQTPASP  240
AKDKVLSTSE NEISQKVSDS SVKRRPIVTP GVTGLRNLGN TCYMNSVLQV LSHLLIFRQC  300
FLKLDLNQWL AMTASEKTRS CKHPPVTDTV VYQMNECQEK DTGFVCSRQS SLSSGLSGGA  360
SKGRKMELIQ PKEPTSQYIS LCHELHTLFQ VMWSGKWALV SPFAMLHSVW RLIPAFRGYA  420
QQDAQEFLCE LLDKIQRELE TTGTSLPALI PTSQRKLIKQ VLNVVNNIFH GQLLSQVTCL  480
ACDNKSNTIE PFWDLSLEFP ERYQCSGKDI ASQPCLVTEM LAKFTETEAL EGKIYVCDQC  540
NSKRRRFSSK PVVLTEAQKQ LMICHLPQVL RLHLKRFRWS GRNNREKIGV HVGFEEILNM  600
EPYCCRETLK SLRPECFIYD LSAVVMHHGK GFGSGHYTAY CYNSEGGFWV HCNDSKLSMC  660
TMDEVCKAQA YILFYTQRVT ENGHSKLLPP ELLLGSQHPN EDADTSSNEI LS         712

SEQ ID NO: 61          moltype = DNA  length = 1101
FEATURE                Location/Qualifiers
misc_feature           1..1101
                       note = Other DNA
source                 1..1101
                       mol_type = other DNA
                       organism = Homo sapiens
SEQUENCE: 61
atgactgtcc gaaacatcgc ctccatctgt aatatgggca ccaatgcctc tgctctggaa  60
aaagacattg gtccagagca gtttccaatc aatgaacact atttcggatt ggtcaatttt  120
ggaaacacat gctactgtaa ctccgtgctt caggcattgt acttctgccg tccattccgg  180
gagaatgtgt tggcatacaa ggcccagcaa aagaagaagg aaaacttgct gacgtgcctg  240
gcggaccttt tccacagcat tgccacacag aagaagaagg ttggcgtcat ccccaccaag  300
aagttcattt caaggctgag aaaagagaat gatctctttg ataactacat gcagcaggat  360
gctcatgaat ttttaaatta tttgctaaac actattgcgg acatccttca ggaggagaag  420
aaacaggaaa aacaaaatgg aaaattaaaa aatggcaaca tgaacgaacc tgcggaaaat  480
aataaaccag aactcacctg ggtccatgag atttttcagg gaacgcttac caatgaaact  540
cgatgcttga actgtgaaac tgttagtagc aaagatgaag attttcttga cctttctgtt  600
gatgtggagc agaatacatc cattacccac tgtctaagag acttcagcaa cacagaaaca  660
ctgtgtagtg aacaaaaata ttattgtgaa acatgctgca gcaaacaaga agcccagaaa  720
aggatgaggg taaaaaagct gcccatgatc ttggccctgc acctaaagcg gttcaagtac  780
atggagcagc tgcacagata caccaagctg tcttaccgtg tggtcttccc tctggaactc  840
cggctcttca acacctccag tgatgcagtg aacctggacc gcatgtatga cttggttgcg  900
```

```
gtggtcgttc actgtggcag tggtcctaat cgtgggcatt atatcactat tgtgaaaagt  960
cacggcttct ggcttttgtt tgatgatgac attgtagaga aaatagatgc tcaagctatt  1020
gaagaattct atggcctgac gtcagatata tcaaaaaatt cagaatctgg atatatttta  1080
ttctatcagt caagagagta a                                            1101

SEQ ID NO: 62          moltype = AA  length = 366
FEATURE                Location/Qualifiers
source                 1..366
                       mol_type = protein
                       organism = Homo sapiens
SEQUENCE: 62
MTVRNIASIC NMGTNASALE KDIGPEQFPI NEHYFGLVNF GNTCYCNSVL QALYFCRPFR  60
ENVLAYKAQQ KKKENLLTCL ADLFHSIATQ KKKVGVIPPK KFISRLRKEN DLFDNYMQQD  120
AHEFLNYLLN TIADILQEEK KQEKQNGKLK NGNMNEPAEN NKPELTWVHE IFQGTLTNET  180
RCLNCETVSS KDEDFLDLSV DVEQNTSITH CLRDFSNTET LCSEQKYYCE TCCSKQEAQK  240
RMRVKKLPMI LALHLKRFKY MEQLHRYTKL SYRVVFPLEL RLFNTSSDAV NLDRMYDLVA  300
VVVHCGSGPN RGHYITIVKS HGFWLLFDDD IVEKIDAQAI EEFYGLTSDI SKNSESGYIL  360
FYQSRE                                                             366

SEQ ID NO: 63          moltype = DNA  length = 1923
FEATURE                Location/Qualifiers
misc_feature           1..1923
                       note = Other DNA
source                 1..1923
                       mol_type = other DNA
                       organism = Homo sapiens
SEQUENCE: 63
atggatagat gcaaacatgt agggcggtta cggctcgccc aggaccactc catcctgaac  60
cctcagaagt ggtgctgctt agagtgtgcc accaccgagt ccgtgtgggc ctgcctcaag  120
tgctcccacg tggcctgcgg ccgctatatt gaggaccacg ccctgaaaca ctttgaggag  180
acgggacacc cgctagccat ggaagtccgg gatctctacg tgttctgtta cctgtgcaag  240
gactacgtgc tcaatgataa cccagagggg gacctgaagc tgctaagaag ctccctcctg  300
gcggtccggg gccagaaaca ggacacgccg gtgagacgtg ggcggacgct gcggtccatg  360
gcttcgggtg aggacgtggt cctgccgcag cgcgctcctc agggacagcc gcagatgctc  420
acggctctgt ggtaccggcg tcagcgcctg ctggccagga cgctgcggct gtggttcgag  480
aagagctccc ggggccaggc gaagctggag cagcggcggc aggaggaggc cctggagcgc  540
aagaaggagg aggcgcggag gcggcggcgc gaggtgaaac ggcggctgct ggaggagctg  600
gccagcaccc ctccgcgcaa gagtgcacgg ctgctcctgc acacgccccg cgacgcgggc  660
ccggctgcct cgcgccccgc cgccctccct acctcacgca gagtgcccgc cgccacactc  720
aagctgcgtc gccagccggc catggcccca ggcgtcacgg gcctgcgcaa cctgggcaac  780
acctgctaca tgaactccat cctccaggtg ctcagccacc tccagaagtt ccgagaatgt  840
ttcctcaacc ttgacccttc caaaacggaa catctgtttc ccaaagccac caacgggaag  900
actcagcttt ctggcaagcc aaccaacagc tcggccacgg agctgtcctt gagaaatgac  960
agggccgagg catgcgagcg ggagggcttc tgctggaacg gcagggcctc cattagtcgg  1020
agtctggagc tcatccagaa caaggagccg agttcaaagc acatttccct ctgccgtgaa  1080
ctgcacaccc tcttccgagt catgtggtcc gggaagtggg ccctagtgtc gcccttcgcc  1140
atgctgcact cagtgtggag cctgatccct gccttccgcg gctacgacca acaggacgcg  1200
caggaatttc tctgcgagct gctgcacaag gtgcagcagg aactcgagtc tgagggcacc  1260
acacgccgga tcctcatccc cttctcccag aggaagctca ccaaacaggt cttaaaggtg  1320
gtgaatacca tatttcatgg gcagctgctc agtcaggtca catgtatatc atgcaattac  1380
aaatccaata ccattgagcc cttttgggac ctatccctgg aattccctga acgctatcac  1440
tgcatagaaa aggggtttgt ccctttgaat caaacagagt gcttgctcac tgagatgctg  1500
gccaaattca cagagacaga ggccctggaa gggagaatct acgcttgtga ccagtgtaac  1560
agcaaacgac gaaaatccaa tcccaaaccc cttgttctga gtgaagctag aaagcagtta  1620
atgatctaca gactacctca ggttctccgg ctgcacctta aaagattcag gtggtctggc  1680
cgtaatcatc gagagaagat tggggtccat gtcgtctttg accaggtatt aaccatggaa  1740
ccttactgct gcagggacat gctctcctct cttgacaaag agacctttgc ctatgatctc  1800
tccgcagtgg tcatgcatca cgggaaaggg tttggctcag gacactacac agcctattgc  1860
tacaacacag agggaggtgc gtgcgcttta ctctgtgggg tgggggacac ggaaaggggt  1920
tga                                                                1923

SEQ ID NO: 64          moltype = AA  length = 640
FEATURE                Location/Qualifiers
source                 1..640
                       mol_type = protein
                       organism = Homo sapiens
SEQUENCE: 64
MDRCKHVGRL RLAQDHSILN PQKWCCLECA TTESVWACLK CSHVACGRYI EDHALKHFEE  60
TGHPLAMEVR DLYVFCYLCK DYVLNDNPEG DLKLLRSSLL AVRGQKQDTP VRRGRTLRSM  120
ASGEDVVLPQ RAPQGQPQML TALWYRRQRL LARTLRLWFE KSSRGQAKLE QRRQEEALER  180
KKEEARRRRR EVKRRLLEEL ASTPPRKSAR LLLHTPRDAG PAASRPAALP TSRRVPAATL  240
KLRRQPAMAP GVTGLRNLGN TCYMNSILQV LSHLQKFREC FLNLDPSKTE HLFPKATNGK  300
TQLSGKPTNS SATELSLRND RAEACEREGF CWNGRASISR SLELIQNKEP SSKHISLCRE  360
LHTLFRVMWS GKWALVSPFA MLHSVWSLIP AFRGYDQQDA QEFLCELLHK VQQELESEGT  420
TRRILIPFSQ RKLTKQVLKV VNTIFHGQLL SQVTCISCNY KSNTIEPFWD LSLEFPERYH  480
CIEKGFVPLN QTECLLTEML AKFTETEALE GRIYACDQCN SKRRKSNPKP LVLSEARKQL  540
MIYRLPQVLR LHLKRFRWSG RNHREKIGVH VVFDQVLTME PYCCRDMLSS LDKETFAYDL  600
SAVVMHHGKG FGSGHYTAYC YNTEGGACAL LCGVGDTERG                        640
```

-continued

```
SEQ ID NO: 65          moltype = DNA  length = 657
FEATURE                Location/Qualifiers
misc_feature           1..657
                       note = Other DNA
source                 1..657
                       mol_type = other DNA
                       organism = Homo sapiens
SEQUENCE: 65
atggacgggt ccggggagca gcccagaggc ggggggccca ccagctctga gcagatcatg  60
aagacagggg ccctttttgct tcagggtttc atccaggatc gagcagggcg aatggggggg  120
gaggcacccg agctggccct ggacccggtg cctcaggatg cgtccaccaa gaagctgagc  180
gagtgtctca agcgcatcgg ggacgaactg gacagtaaca tggagctgca gaggatgatt  240
gccgccgtgg acacagactc cccccgagag gtctttttcc gagtggcagc tgacatgttt  300
tctgacggca acttcaactg gggccgggtt gtcgcccttt tctactttgc cagcaaactg  360
gtgctcaagg ccctgtgcac caaggtgccg gaactgatca gaaccatcat gggctggaca  420
ttggacttcc tccgggagcg gctgttgggc tggatccaag accagggtgg ttgggtgaga  480
ctcctcaagc ctcctcaccc ccaccaccgc gccctcacca ccgcccctgc ccccaccgtcc  540
ctgcccccccg ccactcctct gggaccctgg gccttctgga gcaggtcaca gtggtgccct  600
ctccccatct tcagatcatc agatgtggtc tataatgcgt tttccttacg tgtctga     657

SEQ ID NO: 66          moltype = AA  length = 218
FEATURE                Location/Qualifiers
source                 1..218
                       mol_type = protein
                       organism = Homo sapiens
SEQUENCE: 66
MDGSGEQPRG GGPTSSEQIM KTGALLLQGF IQDRAGRMGG EAPELALDPV PQDASTKKLS  60
ECLKRIGDEL DSNMELQRMI AAVDTDSPRE VFFRVAADMF SDGNFNWGRV VALFYFASKL  120
VLKALCTKVP ELIRTIMGWT LDFLRERLLG WIQDQGGWVR LLKPPHPHHR ALTTAPAPPS  180
LPPATPLGPW AFWSRSQWCP LPIFRSSDVV YNAFSLRV                          218

SEQ ID NO: 67          moltype = DNA  length = 918
FEATURE                Location/Qualifiers
misc_feature           1..918
                       note = Other DNA
source                 1..918
                       mol_type = other DNA
                       organism = Homo sapiens
SEQUENCE: 67
atgagtgtgg atccagcttg tccccaaagc ttgccttgct ttgaagcatc cgactgtaaa  60
gaatcttcac ctatgcctgt gatttgtggg cctgaagaaa actatccatc cttgcaaatg  120
tcttctgctg agatgcctca cacggagact gtctctcctc ttccctcctc catggatctg  180
cttattcagg acagccctga ttcttccacc agtcccaaag gcaaacaacc cacttctgca  240
gagaatagtg tcgcaaaaaa ggaagacaag gtcccagtca agaaacagaa gaccagaact  300
gtgttctctt ccacccagct gtgtgtactc aatgatagat ttcagagaca gaaatacctc  360
agcctccagc agatgcaaga actctccaac atcctgaacc tcagctacaa acaggtgaag  420
acctggttcc agaaccagag aatgaaatct aagaggtggc agaaaaacaa ctggccgaag  480
aatagcaatg gtgtgacgca gaaggcctca gcacctacct accccagcct ctactcttcc  540
taccaccagg gatgcctggt gaacccgact gggaaccttc caatgtggag caaccagacc  600
tggaacaatt caacctggag caaccagacc cagaacatcc agtcctggag caaccactcc  660
tggaacactc agacctggtg cacccaatcc tggaacaatc aggcctggaa cagtcccttc  720
tataactgtg gagaggaatc tctgcagtcc tgcatgcagt tccagccaaa ttctcctgcc  780
agtgacttgg aggctgcttt ggaagctgct ggggaaggcc ttaatgtaat acagcagacc  840
actaggtatt ttagtactcc acaaaccatg gatttattcc taaactactc catgaacatg  900
caacctgaag acgtgtga                                                918

SEQ ID NO: 68          moltype = AA  length = 305
FEATURE                Location/Qualifiers
source                 1..305
                       mol_type = protein
                       organism = Homo sapiens
SEQUENCE: 68
MSVDPACPQS LPCFEASDCK ESSPMPVICG PEENYPSLQM SSAEMPHTET VSPLPSSMDL  60
LIQDSPDSST SPKGKQPTSA ENSVAKKEDK VPVKKQKTRT VFSSTQLCVL NDRFQRQKYL  120
SLQQMQELSN ILNLSYKQVK TWFQNQRMKS KRWQKNNWPK NSNGVTQKAS APTYPSLYSS  180
YHQGCLVNPT GNLPMWSNQT WNNSTWSNQT QNIQSWSNHS WNTQTWCTQS WNNQAWNSPF  240
YNCGEESLQS CMQFQPNSPA SDLEAALEAA GEGLNVIQQT TRYFSTPQTM DLFLNYSMNM  300
QPEDV                                                              305

SEQ ID NO: 69          moltype = DNA  length = 18
FEATURE                Location/Qualifiers
misc_feature           1..18
                       note = Forward primer for generating deletion mutants of
                        Bax (1-219)
source                 1..18
                       mol_type = other DNA
                       organism = synthetic construct
SEQUENCE: 69
gaattcgcat ggacgggt                                                18
```

```
SEQ ID NO: 70           moltype = DNA  length = 19
FEATURE                 Location/Qualifiers
misc_feature            1..19
                        note = Forward primer for generating deletion mutants of
                         Bax (220-334)
source                  1..19
                        mol_type = other DNA
                        organism = synthetic construct
SEQUENCE: 70
gaattccgat ggagctgca                                               19

SEQ ID NO: 71           moltype = DNA  length = 20
FEATURE                 Location/Qualifiers
misc_feature            1..20
                        note = Forward primer for generating deletion mutants of
                         Bax (335-579)
source                  1..20
                        mol_type = other DNA
                        organism = synthetic construct
SEQUENCE: 71
gaattcgcaa actggtgctc                                              20

SEQ ID NO: 72           moltype = DNA  length = 20
FEATURE                 Location/Qualifiers
misc_feature            1..20
                        note = Reverse primer for generating deletion mutants of
                         Bax (1-219)
source                  1..20
                        mol_type = other DNA
                        organism = synthetic construct
SEQUENCE: 72
ctcgagcggt tactgtccag                                              20

SEQ ID NO: 73           moltype = DNA  length = 18
FEATURE                 Location/Qualifiers
misc_feature            1..18
                        note = Reverse primer for generating deletion mutants of
                         Bax (220-334)
source                  1..18
                        mol_type = other DNA
                        organism = synthetic construct
SEQUENCE: 73
ctcgagccgc tggcaaag                                                18

SEQ ID NO: 74           moltype = DNA  length = 18
FEATURE                 Location/Qualifiers
misc_feature            1..18
                        note = Reverse primer for generating deletion mutants of
                         Bax (335-579)
source                  1..18
                        mol_type = other DNA
                        organism = synthetic construct
SEQUENCE: 74
ctcgagcgtc agcccatc                                                18

SEQ ID NO: 75           moltype = DNA  length = 21
FEATURE                 Location/Qualifiers
misc_feature            1..21
                        note = Forward primer for point mutation of USP49 (C262S)
source                  1..21
                        mol_type = other DNA
                        organism = synthetic construct
SEQUENCE: 75
ctgggcaaca ccagctacat g                                            21

SEQ ID NO: 76           moltype = DNA  length = 21
FEATURE                 Location/Qualifiers
misc_feature            1..21
                        note = Reverse primer for point mutation of USP49 (C262S)
source                  1..21
                        mol_type = other DNA
                        organism = synthetic construct
SEQUENCE: 76
tggagttcat gtagctggtg t                                            21

SEQ ID NO: 77           moltype = DNA  length = 19
FEATURE                 Location/Qualifiers
misc_feature            1..19
```

```
                        note = Forward primer for generating deletion mutants of
                         USP49 (1-762)
source                  1..19
                        mol_type = other DNA
                        organism = synthetic construct
SEQUENCE: 77
gaattcgatg gatagatgc                                                    19

SEQ ID NO: 78           moltype = DNA  length = 19
FEATURE                 Location/Qualifiers
misc_feature            1..19
                        note = Forward primer for generating deletion mutants of
                         USP49 (763-1131)
source                  1..19
                        mol_type = other DNA
                        organism = synthetic construct
SEQUENCE: 78
gaattctctg cgcaacctg                                                    19

SEQ ID NO: 79           moltype = DNA  length = 20
FEATURE                 Location/Qualifiers
misc_feature            1..20
                        note = Forward primer for generating deletion mutants of
                         USP49 (1132-2067)
source                  1..20
                        mol_type = other DNA
                        organism = synthetic construct
SEQUENCE: 79
tctagaaccc ttcgccatgc                                                   20

SEQ ID NO: 80           moltype = DNA  length = 18
FEATURE                 Location/Qualifiers
misc_feature            1..18
                        note = Reverse primer for generating deletion mutants of
                         USP49 (1-762)
source                  1..18
                        mol_type = other DNA
                        organism = synthetic construct
SEQUENCE: 80
ctcgaggccc gtgacgcc                                                     18

SEQ ID NO: 81           moltype = DNA  length = 18
FEATURE                 Location/Qualifiers
misc_feature            1..18
                        note = Reverse primer for generating deletion mutants of
                         USP49 (763-1131)
source                  1..18
                        mol_type = other DNA
                        organism = synthetic construct
SEQUENCE: 81
ctcgagcgac actagggc                                                     18

SEQ ID NO: 82           moltype = DNA  length = 19
FEATURE                 Location/Qualifiers
misc_feature            1..19
                        note = Reverse primer for generating deletion mutants of
                         USP49 (1132-2067)
source                  1..19
                        mol_type = other DNA
                        organism = synthetic construct
SEQUENCE: 82
tacgtatcaa cccctttcc                                                    19

SEQ ID NO: 83           moltype = DNA  length = 19
FEATURE                 Location/Qualifiers
misc_feature            1..19
                        note = Target sequence #1 of shUSP49s
source                  1..19
                        mol_type = other DNA
                        organism = synthetic construct
SEQUENCE: 83
gtcttcactg tagctcaag                                                    19

SEQ ID NO: 84           moltype = DNA  length = 19
FEATURE                 Location/Qualifiers
misc_feature            1..19
                        note = Target sequence #2 of shUSP49s
source                  1..19
                        mol_type = other DNA
```

-continued

```
                        organism = synthetic construct
SEQUENCE: 84
ggactacgtg ctcaatgat                                            19

SEQ ID NO: 85           moltype = DNA  length = 19
FEATURE                 Location/Qualifiers
misc_feature            1..19
                        note = Target sequence #3 of shUSP49s
source                  1..19
                        mol_type = other DNA
                        organism = synthetic construct
SEQUENCE: 85
ggactacgtg ctcaatgat                                            19

SEQ ID NO: 86           moltype = DNA  length = 24
FEATURE                 Location/Qualifiers
misc_feature            1..24
                        note = Forward primer for targeting USP49
source                  1..24
                        mol_type = other DNA
                        organism = synthetic construct
SEQUENCE: 86
aggactacgt gctcaatgat aacc                                      24

SEQ ID NO: 87           moltype = DNA  length = 21
FEATURE                 Location/Qualifiers
misc_feature            1..21
                        note = Reverse primer for targeting USP49
source                  1..21
                        mol_type = other DNA
                        organism = synthetic construct
SEQUENCE: 87
gcaggagcag ccgtgcactc t                                         21

SEQ ID NO: 88           moltype = DNA  length = 18
FEATURE                 Location/Qualifiers
misc_feature            1..18
                        note = Forward primer for targeting GAPDH
source                  1..18
                        mol_type = other DNA
                        organism = synthetic construct
SEQUENCE: 88
atcccatcac catcttcc                                             18

SEQ ID NO: 89           moltype = DNA  length = 18
FEATURE                 Location/Qualifiers
misc_feature            1..18
                        note = Reverse primer for targeting GAPDH
source                  1..18
                        mol_type = other DNA
                        organism = synthetic construct
SEQUENCE: 89
ccatcacgcc acagtttc                                             18
```